US010292910B2

(12) United States Patent
Feng et al.

(10) Patent No.: US 10,292,910 B2
(45) Date of Patent: May 21, 2019

(54) CONTROLLED RELEASE DUAL WALLED MICROCAPSULES

(71) Applicant: ENCAPSYS, LLC, Appleton, WI (US)

(72) Inventors: Linsheng Feng, Appleton, WI (US); Robert Stanley Bobnock, Menasha, WI (US)

(73) Assignee: ENCAPSYS, LLC, Appleton, WI (US)

( * ) Notice: Subject to any disclaimer, the term of this patent is extended or adjusted under 35 U.S.C. 154(b) by 14 days.

(21) Appl. No.: 15/629,066

(22) Filed: Jun. 21, 2017

(65) Prior Publication Data
US 2017/0283735 A1 Oct. 5, 2017

Related U.S. Application Data

(62) Division of application No. 14/884,684, filed on Oct. 15, 2015, now Pat. No. 9,714,396.

(60) Provisional application No. 62/199,340, filed on Jul. 31, 2015, provisional application No. 62/117,604, filed on Feb. 18, 2015, provisional application No. 62/064,906, filed on Oct. 16, 2014.

(51) Int. Cl.
A61K 8/84 (2006.01)
C11B 9/00 (2006.01)
A61Q 15/00 (2006.01)
A61K 8/11 (2006.01)
A61Q 5/02 (2006.01)
A61K 8/81 (2006.01)
C11D 3/37 (2006.01)
C11D 17/00 (2006.01)
A61L 15/46 (2006.01)
A61Q 19/10 (2006.01)

(52) U.S. Cl.
CPC .............. A61K 8/11 (2013.01); A61K 8/8147 (2013.01); A61K 8/8152 (2013.01); A61K 8/8158 (2013.01); A61K 8/84 (2013.01); A61L 15/46 (2013.01); A61Q 5/02 (2013.01); A61Q 15/00 (2013.01); A61Q 19/10 (2013.01); C11B 9/00 (2013.01); C11D 3/3723 (2013.01); C11D 3/3761 (2013.01); C11D 17/0039 (2013.01); A61K 2800/412 (2013.01); A61K 2800/594 (2013.01)

(58) Field of Classification Search
CPC ...... A61K 8/11; A61K 8/8147; A61K 8/8152; A61K 8/8158; A61K 8/84; A61K 2800/412; A61K 2800/594; A61Q 15/00; A61Q 19/10; A61Q 5/02; C11B 9/00; C11D 17/0039; C11D 3/3723; C11D 3/3761; A61L 15/46
See application file for complete search history.

(56) References Cited

U.S. PATENT DOCUMENTS

| 3,772,215 A | 11/1973 | Gould |
| 4,100,103 A | 7/1978 | Foris et al. |
| 4,396,670 A | 8/1983 | Sinclair |
| 4,406,816 A | 9/1983 | Sliwka |
| 4,552,811 A | 11/1985 | Brown et al. |
| 4,675,249 A | 6/1987 | Bowman |
| 4,753,968 A | 6/1988 | Shioi et al. |
| 4,760,108 A | 7/1988 | Asano et al. |
| 4,908,271 A | 3/1990 | Kasai et al. |
| 4,977,060 A | 12/1990 | Liang et al. |
| 5,061,410 A | 10/1991 | Sakamoto et al. |
| 5,071,706 A | 12/1991 | Soper |
| 5,110,883 A | 5/1992 | Gartner |
| 5,114,824 A | 5/1992 | Tan et al. |
| 5,292,835 A | 3/1994 | Jahns et al. |
| 5,456,852 A | 10/1995 | Isiguro |
| 5,596,051 A | 1/1997 | Jahns et al. |
| 5,990,202 A | 11/1999 | Nguyen et al. |
| 6,057,384 A | 5/2000 | Nguyen et al. |
| 6,200,681 B1 | 3/2001 | Jahns et al. |
| 6,261,483 B1 | 7/2001 | Frank et al. |
| 6,544,926 B1 | 4/2003 | Bodmer et al. |
| 6,716,526 B2 | 4/2004 | Weston et al. |
| 6,869,923 B1 | 3/2005 | Cunningham et al. |
| 7,550,200 B2 | 6/2009 | Hart et al. |
| 7,736,695 B2 | 6/2010 | Schwantes et al. |
| 7,803,422 B2 | 9/2010 | Schwantes et al. |
| 7,932,191 B2 | 4/2011 | Dungworth et al. |
| 7,938,897 B2 | 5/2011 | Hart et al. |
| 7,947,370 B2 | 5/2011 | Jobmann et al. |
| 8,067,089 B2 | 11/2011 | Schwantes |
| 8,071,214 B2 | 12/2011 | Schwantes |
| 8,455,098 B2 | 6/2013 | Schwantes et al. |
| 8,551,935 B2 | 10/2013 | Smets et al. |
| 8,715,544 B2 | 5/2014 | Schwantes |

(Continued)

FOREIGN PATENT DOCUMENTS

| CA | 2714639 A1 | 8/2009 |
| CN | 102899168 B | 10/2013 |

(Continued)

OTHER PUBLICATIONS

International Search Report and Written Opinion for PCT/US2015/055903 (equiv. to claimed priority document U.S. Appl. No. 62/117,604).

Primary Examiner — Irina S Zemel

(74) Attorney, Agent, or Firm — IP&L Solutions; Edward K Welch II

(57) ABSTRACT

A method of forming dual melamine/acrylic walled microcapsules having improved physical properties and release control as well as the microcapsules formed by the process wherein the capsule wall is formed by the use of select (meth)acrylate monomers and/or oligomers and/or select self-condensing melamine resins.

18 Claims, No Drawings

(56) References Cited

U.S. PATENT DOCUMENTS

| | | |
|---|---|---|
| 8,759,275 B2 | 6/2014 | Smets et al. |
| 8,784,984 B2 | 7/2014 | Grey |
| 8,796,381 B2 | 8/2014 | Schwantes et al. |
| 9,714,396 B2 | 7/2017 | Feng et al. |
| 9,714,397 B2 | 7/2017 | Feng et al. |
| 9,993,401 B2 | 6/2018 | Barnett et al. |
| 9,999,579 B2 | 6/2018 | Feng et al. |
| 2003/0118822 A1 | 6/2003 | Jahns et al. |
| 2004/0071746 A1 | 4/2004 | Popplewell et al. |
| 2004/0265589 A1 | 12/2004 | Yamada et al. |
| 2005/0003980 A1 | 1/2005 | Baker et al. |
| 2006/0039934 A1 | 2/2006 | Ness et al. |
| 2006/0102656 A1 | 5/2006 | Troost et al. |
| 2006/0276356 A1 | 12/2006 | Panandiker et al. |
| 2006/0281834 A1 | 12/2006 | Lee et al. |
| 2007/0138673 A1 | 6/2007 | Lee et al. |
| 2007/0275866 A1 | 11/2007 | Dykstra |
| 2008/0227888 A1 | 9/2008 | Jobmann et al. |
| 2009/0274905 A1 | 11/2009 | Schwantes |
| 2010/0286018 A1 | 11/2010 | Hentze et al. |
| 2010/0286601 A1 | 11/2010 | Hentze et al. |
| 2011/0169900 A1 | 7/2011 | Annable et al. |
| 2011/0268778 A1 | 11/2011 | Dihora et al. |
| 2011/0269657 A1 | 11/2011 | Dihora et al. |
| 2011/0269658 A1 | 11/2011 | Dihora et al. |
| 2011/0294715 A1 | 12/2011 | Smets et al. |
| 2013/0137626 A1 | 5/2013 | Last |
| 2013/0157863 A1 | 6/2013 | Hahn et al. |
| 2013/0313734 A1 | 11/2013 | Yao et al. |
| 2014/0037703 A1 | 2/2014 | Dihora et al. |
| 2016/0106635 A1 | 4/2016 | Yan et al. |
| 2017/0165627 A1 | 6/2017 | Duan et al. |
| 2017/0216161 A1 | 8/2017 | Yan et al. |
| 2017/0281985 A1 | 10/2017 | Feng et al. |
| 2017/0281986 A1 | 10/2017 | Feng et al. |
| 2017/0283736 A1 | 10/2017 | Feng et al. |

FOREIGN PATENT DOCUMENTS

| | | |
|---|---|---|
| EP | 1719554 A2 | 11/2006 |
| EP | 2257440 B1 | 8/2015 |
| EP | 2257440 BI | 8/2015 |
| JP | 48-084086 | 11/1973 |
| JP | 2004113840 A | 4/2004 |
| JP | 2007-534855 A | 11/2007 |
| JP | 2013-525565 A | 6/2013 |
| JP | 2013-531694 A | 8/2013 |
| JP | 2013-538882 A | 10/2013 |
| JP | 2014-051670 A | 3/2014 |
| RU | 2095836 C1 | 10/1997 |
| RU | 2095836 C1 | 11/1997 |
| WO | 2009121831 A1 | 10/2009 |
| WO | 20100387071 A1 | 4/2010 |
| WO | 2012075293 A2 | 6/2012 |
| WO | 2015016367 A1 | 2/2015 |
| WO | 2015016368 A1 | 2/2015 |
| WO | 2015016369 A1 | 2/2015 |

CONTROLLED RELEASE DUAL WALLED MICROCAPSULES

RELATED APPLICATIONS

The present application is a divisional application of U.S. patent application Ser. No. 14/884,684 filed Oct. 15, 2015 which claims the benefit of prior filed U.S. Provisional Application No. 62/064,906 filed Oct. 16, 2014 entitled "Controlled Release Microcapsules"; U.S. Provisional Application No. 62/117,604 filed Feb. 18, 2015 entitled "Controlled Release Dual Walled Microcapsules"; and U.S. Provisional Application No. 62/199,340 filed Jul. 31, 2015 entitled "High Strength Microcapsules", the contents of all of which are hereby incorporated herein in their entirety by reference.

FIELD OF THE INVENTION

The present disclosure relates to improved dual melamine resin/-(meth)acrylate polymer walled microcapsules wherein the improvement comprises the use of select combinations of (meth)acrylate esters as the building blocks of the (meth)acrylate polymer. The present disclosure also relates to an improved method for the production of dual melamine resin/-(meth)acrylate polymer walled microcapsules wherein the improvement comprises the use of select combinations of (meth)acrylate esters in the production of the microcapsules. The present disclosure also relates to an improved method for the production of dual melamine resin/(meth)acrylate polymer walled microcapsules and the microcapsules so formed wherein the improvement comprises the use of select combinations of (meth)acrylate esters in the production of the microcapsules together with the concurrent, as opposed to sequential, polymerization of the (meth)acrylate ester and melamine resin in the formation of the microcapsule wall. Finally, in yet another aspect, the present invention relates to an improved method for the production of dual melamine resin/(meth)acrylate polymer walled microcapsules and the microcapsules so formed wherein the improvement comprises the use of select melamine resin prepolymers and/or polymers and/or their precursors, which are capable of self-condensation.

In addition, the present teachings are related to and an extension of those disclosed in U.S. Provisional Patent Application No. 62/064,906 filed on Oct. 16, 2014, the contents of which are hereby incorporated by reference. Specifically, the oil phase (meth)acrylate monomers, oligomers and/or prepolymers and the water phase (meth)acrylate monomers, oligomers and prepolymers disclosed and employed herein are also disclosed and employed in the prior filed provisional application. Accordingly, their relative constituents and make-up (e.g., ratio of monomers/oligomers) as well as the general amounts by which each is used in forming their respective component, all as described herein and therein, are equally applicable to the teachings of this application as well as the aforementioned Provisional Application.

BACKGROUND

Microcapsules and microencapsulation technology are old and well known and their commercial applications varied. Microcapsules have played a significant role in various print technologies where a paper or other like substrate is coated with microcapsules containing ink or an ink-forming or inducing ingredient which microcapsules release the ingredient, generating an image, when fractured by pressure, as by a printing press or a stylus. Microcapsules have also played a significant role in various adhesive and sealant technologies including the encapsulation of solvents for solvent swellable/tackified preapplied adhesives whereby fracture of the microcapsules releases the solvent which softens or tackifies the adhesive to enable bonding and which re-hardened upon evaporation of the solvent. In other adhesive and sealant applications, the microcapsules contain one or more components of a curable or polymerizable adhesive or sealant composition which, upon release, leads to the cure or polymerization of the adhesive or sealant. In all of these early applications, functionality and efficacy, especially for long term storage and utility, is dependent upon the integrity of the microcapsule walls where the sought after integrity pertains to both strength, so as to avoid premature fracture, as well as impermeability, so as to prevent leakage and/or passage of the contents of the microcapsule through the microcapsule walls. In the former situation, parts having a preapplied microencapsulated adhesive have a tendency to bond together if they hit one another or are stacked upon one another where the pressure of the stack is sufficiently high. Even if not bonded, the fracture of the microcapsules results in less adhesive to effect the bond when the bond is intended. Similarly, if the microcapsule walls allow permeation of the active components through the cell wall, even a slow permeation, the product is short lived as cure will be effected when not intended.

As with most any technology, evolution of microencapsulation technology has led to many new applications, including applications that require changes in the physical properties of the microcapsules, especially their walls. New applications require microcapsules that fracture more readily, with less pressure, but not prematurely. Other applications require microcapsules that specifically allow for a controlled, slow release or permeation of the contents from within the microcapsules without the need to actually fracture the same. For example, perfume containing microcapsules are oftentimes applied to advertising inserts in magazines so that the reader can sample the smell of the perfume. Here strength is needed to avoid premature fracturing of the microcapsules due to the weight and handling of the magazine; yet, the microcapsules need ease of fracture so that the reader can simply scratch the treated area to release the contents of the microcapsule. At the same time, it is desirable to allow for some release of the contents, even without fracturing, to induce the reader to want to scratch the sample to get a more accurate sense of the smell.

Another application for microcapsules is in laundering and fabric treatments. A number of products exist wherein microcapsules of various ingredients, including perfumes, are applied to strips of a fabric material and added to the dryer wherein the tumbling action and/or heat of the dryer causes the microcapsules to fracture, releasing the ingredients which, in a volatilized state, permeate and deposit upon the contents of the dryer. This methodology applies that "fresh out of the dryer" smell, but is short lived as the perfume continues to volatilize from the treated fabric. Other products exist whereby microcapsules containing perfumes and other ingredients are applied directly or indirectly to the fabric, especially apparel, to provide a longer lived freshness to the same. Here, the performance or efficacy of these products is oftentimes short lived as the content of the microcapsules escapes too readily from the microcapsules and/or the walls of the microcapsules are too weak and/or have too little give such that normal wearing of the fabric causes the microcapsules to break too readily. Opportunities abound for new microcapsules that address the specific requirements of a given application as well as microcapsules that offer better performance and properties than are attainable with current state of the art microcapsule technology.

Whether applications have driven the evolution of microcapsule technology or the evolution of microcapsule technology has driven their expanded applications, or perhaps a little of both, there has been and continues to be constant development in microencapsulation technology, both in terms of their production/process methodology and their chemistry. Early melamine formaldehyde microcapsules continue to evolve; yet concurrently, they have, to some extent, given way to acrylic and other microcapsule chemistries and technologies. In turn, both have continued to evolve further to dual walled microcapsules of each chemistry as well as both chemistries. While the basic building blocks of the capsule walls have largely remained the same, the specific selection of building blocks and methodology has led to newer and improved microcapsules enabling the microencapsulation of a broader array of ingredients, compounds and elements.

Despite all the advances and improvements, there is still a need for improved specialty microcapsules that provide a suitable mix of release/permeability characteristics and physical properties for today's demanding applications. This is especially so in the area of perfumes and other odiferous ingredients, particularly in relation to fabric, textile and garment treatment, where controlled release and longevity as well as capsule strength and integrity are necessary.

SUMMARY OF THE INVENTION

According to the present teachings there are provided novel, improved microcapsules and methods of forming the same, which exhibit marked improvement in release characteristics and/or excellent physical properties and attributes, preferably attributes of both.

According to a first embodiment of the present teachings there is provided improved dual melamine resin/(meth)acrylate polymer walled microcapsules wherein the improvement comprises the use of a combination of (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer in forming the (meth)acrylate ester-based portion of the microcapsule wall.

According to a second embodiment there is provided an improved method of making dual melamine resin/(meth)acrylate polymer walled microcapsules wherein the improvement comprises the use of a combination of (a) at least one oil soluble or dispersible acidic (meth)acrylate, (b) at least one oil soluble or dispersible simple base, and (c) at least one oil soluble or dispersible multifunctional (meth)acrylate monomer or oligomer in forming the (meth)acrylate ester-based portion of the microcapsule wall.

According to a third embodiment there is provided an improved oil/water phase method of making dual melamine resin/(meth)acrylate polymer walled microcapsules and the microcapsules so formed wherein the improvement comprises (i) the use of either (A) (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer or (B) a combination of (a) at least one oil soluble or dispersible acidic (meth)acrylate, (b) at least one oil soluble or dispersible simple base, and (c) at least one oil soluble or dispersible multifunctional (meth)acrylate monomer or oligomer in forming the (meth)acrylate ester-based portion of the microcapsule wall and (ii) the concurrent or near concurrent deposition and polymerization of the (meth)acrylate polymer and melamine resin at the oil/water phase interface.

According to a fourth embodiment there is provided an improved method of making dual melamine resin/(meth)acrylate polymer walled microcapsules and the microcapsules so formed wherein the improvement comprises the use of (a) at least one water soluble or dispersible multifunctional (meth)acrylate monomer or oligomer alone or in combination with (b) at least one water soluble or dispersible mono- and/or di-functional (meth)acrylate and/or (c) at least one water soluble or dispersible simple base in the production of the (meth)acrylate ester-based portion of the microcapsule wall.

Finally, according to a fifth embodiment there is provided an improved method of making dual melamine resin/(meth)acrylate polymer walled microcapsules and the microcapsules so formed wherein the improvement comprises the select use of water soluble or dispersible melamine resin prepolymers and/or polymers and/or the precursors therefore which are able to polymerize/copolymerize through self-condensation. This fifth embodiment is especially applicable when applied to each of the foregoing four embodiments.

While the recitation of the first through fourth embodiments above teaches the use of the combination of the therein mentioned (meth)acrylate ester monomers and/or oligomers, it is also to be appreciated that one may also or in substitution therefor employ a preformed oligomer/prepolymer of the select (meth)acrylate ester monomers and/or oligomers. Specifically, e.g., one may employ an oligomer/prepolymer comprising the reaction product of (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer, with or without isolation and/or purification thereof as the wall forming component. Alternatively, one may form oligomers of two or all three of the (meth)acrylate esters and/or oligomers (a), (b) and (c) and add the third or additional monomer and/or oligomer, respectively, during the wall forming stage.

The "dual walled" microcapsules produced according to the present teaching are such that one of the innermost shell portion and the outermost shell portion of the microcapsule wall is essentially homopolymers or, as appropriate copolymers of the wall forming materials of the respective wall forming composition, e.g., a melamine polymer in the case of the melamine based wall forming composition or a (meth)acrylic polymer in the case of the (meth)acrylate based wall forming composition: which is which will depend upon the specific steps and sequence of steps employed. In contrast, the intermediate region of the shell wall, i.e., that region where the shell wall forming materials of each come in contact with the other, may present itself in a number of different states depending upon the specific steps and sequence of steps employed and, equally important, the selection of the monomers, oligomers and/or prepolymers of each shell wall forming material used. Specifically, the intermediate region may show a distinct transition of one composition to the other, as if one layer is built upon the other, or it may manifest in the form of a transition region of varying thickness where the transition region comprises (a) an interpenetrating network of the two polymers which physically lock the two wall materials together, (b) a copolymer of the monomers, oligomers and/or prepolymers of each, or (c) both.

A distinct transition will typically be found where, e.g., one sequentially forms the microcapsule wall, encapsulating the core, with one material and, once that wall is fully formed, depositing and building or polymerizing the second wall forming material upon the already formed wall. Alternatively, the core composition itself may comprise the second wall forming material and the outer wall could be formed first on the droplet of the core and inner wall forming material and then the overall composition subjected to conditions which then polymerize the wall forming materials contained within the droplet to build the second portion of the wall from within.

Despite the clear sequential build noted in the preceding paragraph, it is also be understood that a transition region may still manifest itself at the interface of the two polymers, particularly in those circumstances where the polymer of the first formed wall has groups that are reactive with one or more of the monomers or components of the second wall forming material and/or where the first formed wall has polymer chains that extend from the surface thereof and/or voids or a loose network of polymer chains that allow the monomers and oligomers of the second wall forming material to penetrate prior to and/or during the polymerization of the second wall forming material. In the first, where reactive groups are present, there is a copolymerization creating a chemical bond. In the second, where the polymer chains extend from the surface and/or voids or a loose polymer network is formed, an interpenetrating network is formed physically locking one wall forming material to the other.

On the other hand, a transition region which may be in the form of an interpenetrating network of one polymer or wall forming material with the other and/or a copolymer region is typically, though not necessarily, formed if one elects to form the shell wall from both shell wall forming materials concurrently or with only a brief delay or stagger in the initiation of polymerization of one and then the other. Most preferably, the polymerization of one shell wall forming material is initiated and allowed to progress to a point where the core is partially encapsulated, perhaps twenty-five percent or more, preferably fifty percent or more, but not fully, encapsulated or, at best, has a monolayer or so of wall formed across the surface of the core material before initiating polymerization of the second wall forming material. Alternatively, one may initiate polymerization of one wall forming material to form a seed microcapsule which has the essential structure of a shell, but is still permeable to monomer and/or initiator or radicals prior to initiation of polymerization of the second wall forming material.

Regardless of which of the foregoing embodiments is followed, once the intermediate or transition region of the shell wall is formed and the wall forming materials of each composition is fully isolated from the other, the polymerization of the shell wall forming materials continues, but is now limited to those components of that shell wall forming composition. Where the wall is formed sequentially, only the second wall forming material will continue to polymerize, either on the exterior surface or on the interior surface of the shell wall as appropriate. Where the wall forming is concurrent or slightly staggered, both wall forming materials will continue to polymerize, the inner or core wall building material building from within upon the inner surface of the shell wall and the continuous phase or exterior wall forming material continuing to build from without upon the exterior surface of the microcapsule wall.

The microcapsules and the microencapsulation processes of the present teachings are applicable to most any application where microcapsules can be used and are especially suitable for use in those instances where controlled release of the microencapsulated material is desired while integrity of the microcapsule wall is maintained. In particular, the present microcapsules are especially suited for use where an aromatic ingredient is to be encapsulated which ingredient is intended to allow for the gradual release of the aromatic ingredient or, at least, its aroma or smell, while withstanding moderate physical forces to the microcapsules so as to avoid premature and/or undesired rupture of the so formed microcapsules. In particular, the microcapsules of the present teachings have significant use in scratch-n-sniff applications, in laundry applications, in odor control applications, etc.

DETAILED DESCRIPTION

As used in the specification and claims, the term (meth) acrylate refers to the acrylate as well as the methacrylate: when just the acrylate is intended to be exemplified, it will be so presented, e.g., isobornyl acrylate, and when just the methacrylate is intended to be exemplified, it will be so presented, e.g., isobornyl methacrylate. Hence, isobornyl (meth)acrylate refers to both isobornyl acrylate and isobornyl methacrylate. The use of the phrase "(meth)acrylate oligomer/prepolymer" means that the (meth)acrylate material may exist as an oligomer, as a prepolymer or as a combination of both oligomers and prepolymers, with or without some monomer. Similarly, the phrase "melamine prepolymer" means oligomer, prepolymer or both oligomer and prepolymer of the melamine material, with or without some monomer/precursor materials. Finally, the word "initiator" as used herein is intended to mean true initiators, such as the free radical initiators, for inducing polymerization of the acrylate esters as well as those catalysts and/or accelerators, including alkaline inducing agents, which promote and/or accelerate the polymerization of the monomers, oligomers and/or prepolymers, especially the melamine prepolymers and/or precursors therefore.

Additionally, the descriptors "water soluble or dispersible", "water soluble", and "water dispersible" when referencing certain (meth)acrylate monomers and/or oligomers or initiators means that the specified component is soluble or dispersible in the given matrix solution on their own or in the presence of a suitable solubilizer or emulsifier or upon attainment of certain temperatures and/or adjustment of pH. Furthermore, as presented herein, the microcapsules and their methods of production are oftentimes characterized as being "improved." With respect to the microcapsules themselves, the improvement is with respect to similar microcapsules formed from some, but not all, of the specified components. For example, an improved microcapsule formed of one of the select combinations of (meth)acrylic esters will typically show improved physical characteristics as compared to a single walled microcapsule formed from some, but not all, of those (meth)acrylic esters or to a dual walled MF/Acrylic microcapsule formed of melamine resin and, again, some, but not all, of those (meth)acrylic esters. With respect to the method, the improvement may be with respect to the physical characteristics of the so formed microcapsules or with respect to the ease, simplicity, and/or efficacy of the method itself, or both.

According to a first embodiment of the present teachings there is provided improved dual melamine resin/(meth)

acrylate polymer walled microcapsules wherein the improvement comprises the use of a combination of (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer in forming the (meth)acrylate ester-based portion of the microcapsule wall.

According to a second embodiment there is provided an improved method of making dual melamine resin/(meth)acrylate polymer walled microcapsules wherein the improvement comprises the use of a combination of (a) at least one oil soluble or dispersible acidic (meth)acrylate, (b) at least one oil soluble or dispersible simple base, and (c) at least one oil soluble or dispersible multifunctional (meth)acrylate monomer or oligomer in forming the (meth)acrylate ester-based portion of the microcapsule wall.

According to a third embodiment there is provided an improved oil/water phase method of making dual melamine resin/(meth)acrylate polymer walled microcapsules and the microcapsules so formed wherein the improvement comprises (i) the use of either (A) (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer or (B) a combination of (a) at least one oil soluble or dispersible acidic (meth)acrylate, (b) at least one oil soluble or dispersible simple base, and (c) at least one oil soluble or dispersible multifunctional (meth)acrylate monomer or oligomer in forming the (meth)acrylate ester-based portion of the microcapsule wall and (ii) the concurrent or near concurrent deposition and polymerization of the (meth)acrylate polymer and melamine resin at the oil/water phase interface.

According to a fourth embodiment there is provided an improved method of making dual melamine resin/(meth)acrylate polymer walled microcapsules and the microcapsules so formed wherein the improvement comprises the use of (a) at least one water soluble or dispersible multifunctional (meth)acrylate monomer or oligomer alone or in combination with (b) at least one water soluble or dispersible mono- and/or di-functional (meth)acrylate and/or (c) at least one water soluble or dispersible simple base in the production of the (meth)acrylate ester-based portion of the microcapsule wall.

Finally, according to a fifth embodiment there is provided an improved method of making dual melamine resin/(meth)acrylate polymer walled microcapsules and the microcapsules so formed wherein the improvement comprises the select use of water soluble or dispersible melamine resin prepolymers and/or polymers and/or the precursors therefore which are able to copolymerize through self-condensation. This fifth embodiment is especially applicable when applied to each of the foregoing four embodiments.

As noted in the background section, microcapsules and microencapsulation processes are well known and have been practiced for decades. Exemplary microcapsules include those whose microcapsule walls are formed of melamine resin, (meth)acrylic polymer, and dual melamine resin/(meth)acrylic polymer. These are described in, among others: Schwantes—U.S. Pat. Nos. 7,736,695; 8,071,214 and 8,455,098; Bodmer et. al.—U.S. Pat. No. 6,544,926; Lee et. al.—US 2007/0138673; Sakamoto et. al.—U.S. Pat. No. 5,061,410; Liang et. al.—U.S. Pat. No. 4,977,060 and Bowman—U.S. Pat. No. 4,675,249; all of which are incorporated herein by reference in their entirety. Those skilled in the art, having the benefit of the present teachings, will readily be able to employ said processes and modify said processes to practice the present invention.

The microencapsulation processes of the present teachings are of two general types: a dual oil/aqueous phase system and process and a dual aqueous based system and process. The wall formation from each phase may be performed concurrently, with a stagger or delay sequentially. The latter is more typical of the dual water phase process while the other two are more typical of the dual oil/water phase process.

The first microencapsulation process involves the use of a dual oil/water phase system comprising a melamine containing aqueous phase and a (meth)acrylate ester containing oil phase. While the dual oil/water phase process may be used to form microcapsules having either an (meth)acrylic/melamine or melamine/(meth)acrylic core/shell construction, it is especially suited, particularly from a convenience standpoint, for those processes where the core is an oil phase core and the inner wall of the microcapsule is a (meth)acrylic polymer wall. The latter process generally involves an emulsion or dispersion of the oil phase dispersed in a continuous aqueous phase. In these systems, the discontinuous phase will typically comprise or contain the core material to be encapsulated as well as the inner wall forming materials. These dual phase systems are especially suited for allowing for a concurrent or staggered/delayed wall formation whereby formation of the shell wall from the wall forming material of one phase is initiated and, shortly thereafter, preferably before full encapsulation is attained, polymerization of the second wall forming material is initiated so that there is some dual polymerization at the interface of the two phases. Of course, one may opt to employ a sequential process where microcapsules are formed of one wall forming material and then subjected to a second wall formation process using the second wall forming material.

The second microencapsulation process generally employs two water phase wall forming compositions; though here, unlike in the dual oil/water phase process, the shell wall formation from the first water phase composition is more typically completed or substantially completed before the second water phase composition is added to form the second shell layer. In this instance, the first of the two water phase compositions will contain the core material to be encapsulated as well as the initial wall forming materials.

Having addressed the phases of the encapsulation process attention is now directed to the processes by which the microcapsules are made. For convenience, the discussion of the dual phase system is presented on the basis of an oil phase core and inner wall forming composition and an aqueous phase material as the continuous phase and the outer wall forming composition.

A first step of the dual phase process is the formation of the oil phase composition. Generally speaking, the oil phase composition will comprise either (A) (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer; (B) a combination of (a) at least one oil soluble or dispersible acidic (meth)acrylate, (b) at least one oil soluble or dispersible simple base, and (c) at least one oil soluble or dispersible multifunctional (meth)acrylate monomer or oligomer or (C) a (meth)acrylate oligomer/prepolymer of (A) or (B) and the core material itself, i.e., the material, ingredient, etc. that is intended to be encapsulated.

Most preferably, the oil phase wall forming material is in the form of the (meth)acrylate oligomer/prepolymer which is pre-formed or formed in-situ as a first pre-step or sub-step to the formation of the oil phase.

In the case of the pre-formed (meth)acrylate oligomer/prepolymer, the same may be purchased or formed and stored for later use as a separate ingredient in the microencapsulation processes. However, it is preferred that the (meth)acrylate oligomer/prepolymer be formed in-situ as a first step or pre-step in microencapsulation process, with or without isolation. This allows for one to make adjustments in the relative ratio of the (a), (b) and (c) components to optimize the (meth)acrylate oligomer/prepolymer for the specific end-use of the microcapsules. Of course, it is also to be understood that while it is preferred that the (meth)acrylate oligomer/prepolymer be formed of all three constituents, (a), (b) and (c), an oligomer/prepolymer may also be formed of any two of said constituents or from less than the full amount of said constituents with the remaining constituent and/or the balance of the remaining constituents added to the oil phase composition as a second oil phase composition prior to or concurrent with the wall formation step.

Furthermore, in the case of the in-situ formed (meth)acrylate oligomer/prepolymer, the components therefore are combined together with a suitable carrier or oil phase material, which may be the core material (or in addition to the core material), and subjected to suitable conditions, preferably in the presence of a suitable initiator, and for a sufficient period of time to generate the desired oligomer/prepolymer. The so formed (meth)acrylate oligomer/prepolymer, with or without isolation, is then combined with a second oil phase composition which, preferably, contains an initiator and, most likely and preferably, the core material (or the remaining portion thereof, as appropriate) to be encapsulated and, optionally, an acid or other ingredient that will facilitate or drive the oligomer/prepolymer to the interface of the oil phase and the water phase. Though the foregoing teaches the formation of the (meth)acrylate oligomer/-prepolymer prior to adding the remaining oil phase composition components, it is also to be appreciated that all or most all of the components of the oil phase composition can be combined prior to effecting the oligomerization/pre-polymerization of the monomers/oligomers to produce the (meth)acrylate oligomer/prepolymer.

In any event, once the oil phase composition is formed and, preferably, the (meth)acrylate oligomer/prepolymer formed as well, the resultant oil phase composition is then combined with an excess, by volume, of a first water phase composition which preferably comprises a non-ionic emulsifier and/or an initiator, which may be the same or a different initiator than is present in the oil phase composition, or a combination of initiators, one of which may be the same as the initiator in the oil phase composition, or a second initiator suitable for effecting polymerization of the oil phase wall forming material. Optionally, the first water phase may also contain water phase wall forming material, monomer and/or initiator for the water phase wall forming material, as well. The combination of the oil phase and the water phase composition is then subjected to emulsification/high shear mixing to create a dispersion/emulsion of the oil phase in the water phase. Emulsification is continued until the desired size of the droplets is attained. Although this may vary from application to application, for many applications it is desirable that the target droplet size is from 0.1 to 80 microns, preferably from 0.5 to 50 microns, more preferably from 1 to 30 microns. Larger sizes for particular applications are also feasible.

Following completion of the formation of the emulsion, a second water phase composition comprising the melamine resin or resin precursors and, as appropriate, suitable initiators and the like is added to the aqueous continuous phase with continued mixing. Generally, and preferably, at this point the high speed shear mixing or milling is stopped and a slower mixing, with or without the switching of the blade element, is maintained. For example, one may opt to replace the emulsification/milling blade with a mixer blade to maintain a less shear force mixing of the emulsion.

Notwithstanding the foregoing, it is also be appreciated that one can employ a single aqueous phase composition which includes all of the necessary components or ingredients instead of multiple aqueous phase compositions or the second aqueous phase composition may be added to the mixture prior to completion of the emulsification process. However, in each of these instances, one is merely adding additional volume to the water phase and the overall composition which reduces the efficiency of the emulsification process. Hence, it is preferred that a second water phase composition be employed and added after completion of the emulsification process.

Concurrent with or following the emulsification of the combined phases, preferably, at a point near or following achievement of the desired droplet size, the overall reaction mix is subjected to such conditions as will initiate polymerization of the oil phase wall forming materials or components in the emulsified droplets so as to commence wall formation at the oil phase/water phase interface. Again, this may be the polymerization of the initial monomers/oligomers or, most preferably, of the (meth)acrylate oligomer/prepolymer. At this point, it may be desirable to add, if not already present in one or both of the oil and water phases, an acid or other component that drives or causes the polymerizable or wall forming materials of each phase to migrate to the oil phase/water phase interface.

Regardless once or shortly after the second water phase compositions is added to the mix, the composition is then subjected to such conditions as will activate the initiator and/or initiate or promote the polymerization of the wall forming material in the continuous phase, i.e., the melamine, while maintaining if not enhancing the polymerization of the wall forming material in the core. Owing to the nature of the monomers/oligomers, those in the continuous phase will preferably have a tendency to migrate through the continuous phase to the oil phase/water phase interface where they deposit and polymerize on the capsule wall material that is polymerizing out of the oil phase or core materials. Here, as with the oil phase material, it is contemplated that the continuous phase composition includes or has added thereto an ingredient or is subjected to conditions which drive the wall forming materials therein to the interface.

Once the oil phase droplet is completely encapsulated, capsule wall formation continues until the desired end-point with the oil phase wall forming material continuing to build from the inner surface of the capsule wall inwards and the continuous phase wall forming material, i.e., the melamine resin, continuing to build and add to the exterior surface of the capsule wall. In this way, regardless of what polymers, copolymers, and/or interpolymers (e.g., interpenetrating networks) exist in the midsection of the capsule wall, i.e., at the original oil/water interface, the inner wall surface and the exterior wall surface of the final microcapsules are generally comprised of polymers formed of only the oil phase wall forming materials and the aqueous phase wall forming materials, respectively.

Further, while the foregoing teaches the initiation of the oil phase wall concurrent with or staggered relative to the polymerization of the aqueous phase melamine resin wall forming material, it is also contemplated that the oil phase materials could be fully polymerized before the addition of the second water phase and/or before activation or initiation of the polymerization of the water phase polymerizable material. Alternatively, one may also initiate polymerization of the aqueous phase materials before initiation of the oil phase material so that the oil phase droplet is partially or fully encapsulated with the melamine resin before the oil phase wall forming material begins to build upon the inner surface of the melamine resin wall. Most preferably, as noted above, the process involves the polymerization of the oil phase wall forming material and partial encapsulation of the oil phase droplet therewith prior to initiation of the polymerization of the aqueous phase wall forming material. Alternatively, as noted above, the oil phase may be fully encapsulated in a seed microcapsule, one whose wall completely surrounds the oil droplet but is not integral, rather it has voids and gaps whereby the liquid/liquid interface between the two phases still exists. In any event, depending upon the selection of the water phase wall forming materials and the oil phase wall forming materials and the timing of their combination, it is contemplated that the wall forming component(s) of one may copolymerize with one or more of the wall forming component(s) of the other and/or form an interpenetrating network therewith.

The conditions and duration of the curing or polymerization process will vary depending upon the ingredients, most especially the initiators, activators and/or catalysts used, and the desired outcome relative to the capsule size and, more pertinently, the wall thickness. In the case of heat activated initiators, it is especially desirable to employ activators that have different activation temperatures and/or have varied half-lives so that one can better control the extent or degree of polymerization. In this regard, the nature of the activation energy employed, the extent of the exposure to the activation energy, and the duration thereof all have a significant impact on the extent or degree of cure. In the case of heat activated free radical initiators, generally the higher the temperature to which the activator is exposed above the activation temperature the more and/or faster free radicals are generated. Similarly, in the case of actinic radiation activated free radical initiators, the higher the intensity of the radiation of the requisite wavelength, the greater the effect. Thus, those skilled in the art having the benefit of the present teachings combined with some experience with the present process will be able to determine the operating conditions for best effecting the present encapsulation process. Nevertheless, it is also to be appreciated that when combining two or more of the same phase compositions to the other, e.g., the combination of two water phase compositions or two oil phase compositions, it is desirable to provide proper mixing to ensure a homogeneous or near homogeneous mixture before initiating polymerization. Similarly, when combining one phase type to the other, it is desirable to ensure that the proper droplet size is attained before initiating polymerization.

From the foregoing, it is apparent that the oil/water phase system and process provides for a number of variables. For the sake of providing additional clarity, one may consider, for example, that in endeavoring to produce about 600 grams of microcapsules one would employ an overall system having 10 to 70 weight percent, preferably 35 to 65 weight percent, oil phase solvent and oil or other core material to be encapsulated; 10 to 70 weight percent, preferably 35 to 65 weight percent water; and 1 to 40 weight percent, usually 3 to 35 weight percent, preferably 5 to 30 weight percent of wall forming material. As to the wall forming materials themselves, the oil phase monomers/oligomers are generally used in an amount of 10-90, preferably 30-80, more preferably, 40-70, most preferably, 55-65 weight percent and the water phase monomers/resins are employed in an amount of 10-90, preferably, 20-70, more preferably, 30-60, most preferably 35-45 weight percent, the weight percent based upon the combined weight of the oil phase and water phase wall forming materials.

Though the foregoing amounts are typical, it is also to be understood that the use of higher water content levels are possible, but not necessary and merely creates a dilute solution and/or requires the presence of higher amounts of the necessary ingredients to provide for an efficacious process. Similarly, higher concentrations of the oil phase materials may be used, but then the concentration of the droplets becomes too dense and may result in an unstable emulsion and/or coalescence of the droplets, or worse, an inversion whereby the oil phase becomes the continuous phase. Regardless, the amount of wall forming material is, in part, a function of the size of the microcapsules and the properties, especially the physical properties, of the resultant microcapsules. Generally, though, the capsule wall comprises from 1 to 40 weight percent, preferably from 5 to 30 weight percent, most preferably from 8 to 20 weight percent of the microcapsule.

The foregoing presents a general overview of the process and alternate steps that may be used in forming the presently claimed microcapsules in an oil and water system. As noted above, those skilled in the art, having the advantage of the teachings herein, will readily recognize various methodologies and process steps, sequences and conditions that may be employed or altered to form the microcapsules intended by the present teachings. As further exemplification and for the sake of added clarity, the following paragraphs will present one specific method of forming a (meth)acrylic/melamine dual walled microcapsule having an oil core with an acrylic inner shell layer employing a first and second oil phase, the first comprising the wall forming materials and the second the core material, and a first and second water phase, the first comprising emulsifier and/or initiator and the second the melamine resin. Ranges of the reaction parameters are set forth in parenthesis.

An oil/water phase acrylic/melamine dual walled microcapsule is produced as follows:

(I) the components of a first oil phase composition comprising a scented oil to be encapsulated as the core material and one or more free radical initiators are placed in a reactor vessel and mixed at 35° C. under a $N_2$ blanket at a low mixer speed (120 rpm). The mixture is heated over a period of about 45 minutes to 70° C. and held at that temperature for an additional 45 minutes. Thereafter, the mixture is cooled to 50° C. (50° C.-60° C.) over a period of 30 minutes (30-75 minutes) and held at that temperature.

(II) independently, a second oil phase composition comprising the oil phase wall forming materials is prepared in a separate mixing vessel and heated to 50° C. (50° C.-60° C.) and mixed.

(III) independently a first water phase composition comprising water, a plurality of initiators, one for effecting polymerization of the oil phase wall forming materials and the other for effecting polymerization of the melamine resin water phase wall forming materials, an emulsifier and a pH adjuster is likewise combined in a separate mixing vessel and heated to 50° C. (50° C.-60° C.) and mixed.

(IV) the second oil phase composition is then added to the reactor vessel containing the first oil phase and the mixture mixed at slow speed for 10 minutes.

(V) promptly thereafter, the first water phase composition is then gradually added to the reactor vessel containing the combined oil phase materials under high shear mixing at about 1200 rpm and milling continued until the desired droplet size is attained, approximately 60 minutes or so. During the milling process, samples of the emulsion are periodically taken from the reactor vessel to check droplet size. Once the desired droplet size is attained, the mixing is stopped and the milling blade replaced with a mixing blade.

(VI) a second water phase composition comprising the water phase melamine resin wall forming materials, which had been previously mixed and heated to 50° C. (50° C.-60° C.), is then added to the reaction vessel containing the emulsion and the whole of the mixture mixed at low speed, ~120 rpm while elevating the temperature of the mixture to 75° C. over a period of 60 minutes (60-180) with mixing and held for 4 hours.

(VIII) the mixture is then further elevated to 95° C. over a period of 60 minutes and held for an additional 6 hours to form the final microcapsules.

It is believed that the initial heating of the first oil phase composition in Step (I) initiates the free radical initiator, thereby generating free radicals which, when the second oil phase composition is added will enable oligomerization/prepolymerization of the oil phase wall forming materials to form the (meth)acrylate oligomer/prepolymer. Similarly, it is believed that the period of heating and mixing following the addition of the water phase material for formation of the emulsion initiates wall formation from the oil phase at the interface of the oil phase and water phase. Adding the second water phase composition shortly thereafter ensures the concurrent polymerization of the two wall forming materials at the interface so as to produce the aforementioned interpenetrating network and/or copolymerization.

Of course a multitude of variations in the steps, their sequence, etc., as well as the introduction of other constituents for aiding and/or facilitating cell wall formation are also contemplated and can be employed without diverging from the inventive aspects of the present teachings. For example, as noted previously, instead of forming the (meth)acrylate oligomer/prepolymer as a step in the process, one may also use a preformed (meth)acrylate oligomer/prepolymer. The same also holds true for the melamine prepolymer where the prepolymer may be formed as part of the overall process steps or it may be preformed and used in the process, again with or without separation, purification and/or isolation.

Additionally, the claimed processes may include various additives and other constituents to enable and/or facilitate the formation of the microcapsules. For example, it is desirable and, at times, necessary, to employ emulsifiers to aid in the formation and/or stability of the oil in water and/or water in oil dispersions, as appropriate, as well as emulsifiers and/or solubilizers to assist in dispersing and/or solubilizing the components in their respective phases, i.e., aqueous phase components in the water or aqueous phase matrix material and the oil phase components in the oil phase matrix material. Suitable emulsifiers may be in either or both phases and/or in each, some, or all of the respective premix components of each, e.g., the first water phase composition, the second water phase composition, the first oil phase composition, the second oil phase composition, etc. Most especially, the matrix phase composition will have an emulsifier for creating an emulsion or droplets of the dispersed phase composition in the matrix phase composition.

Sequencing of the process steps and/or the timing of the same is also able to be changed. In each of the foregoing embodiments the core phase is added to and dispersed in a first matrix phase composition containing one or more initiators for effecting polymerization of one or both wall forming materials. As an alternative, the core phase can be dispersed in a first matrix phase composition which includes the melamine resin wall forming material, or the precursors therefore, but not the initiator therefore. Similarly, the oil phase, while described above as comprising the combination of two separate oil phase compositions, could be made as a single composition or could be the combination of more than two pre-mix compositions. For example, if solubility and/or dispensability of the constituents of the oil phase composition is an issue, each can be separately dissolved/dispersed and then these premixes combined. The same also holds true for the water phase which may be formed as a single composition or can be formed in the course of the microencapsulation process through the sequential addition of multiple water phase premixes of the components therefore.

Additionally, while the foregoing contemplates a brief delay in the initiation/polymerization of the wall forming materials of each phase, each may be initiated concurrently or sequentially where a shell or, as noted above, a seed microcapsule is formed of one of the wall forming materials and, once that formation is completed or nearly so, the other is initiated to build upon the first formed shell wall or at any point in between. Preferably the initiation of the polymerization of the two wall forming materials is staggered, though just briefly. Most preferably, polymerization of the core phase wall forming material is initiated prior to initiation of the polymerization of the matrix phase wall forming. In any event, where there is a stagger, it is preferred that it be brief such that the dispersed droplet is not fully encapsulated by one wall forming material prior to initiation of polymerization of the other wall forming material, or if fully encapsulated, is very thin so as to allow some physical integration of the polymer chains of one with the polymer chains of the other as opposed to simply one polymer overlaying or coating the other. Staggering of the initiation/polymerization of the wall forming materials may be achieved by, e.g., not adding the matrix phase wall forming materials until after initiating polymerization of the core phase wall forming material; not adding the initiator for the polymerization of the matrix phase wall forming material until after initiating polymerization of the core phase wall forming material, subjecting the reaction mix to conditions which will effect polymerization of either the core or the matrix wall forming material but not the other, etc. Again, a highly desirable objective is to ensure that the wall forming materials, at least during the initial stages of capsule wall formation, engage in some copolymerization and/or form an interpenetrating network and/or involves a physical entrapment of the polymer chains of one in the other.

In any event, once the core phase droplet is completely encapsulated, capsule wall formation continues until the desired end-point with the core phase wall forming material continuing to build from the inner surface of the capsule wall inwards and the matrix phase wall forming material continuing to build and add to the exterior surface of the capsule wall. In this way, regardless of what polymers, copolymers, and/or interpolymers (e.g., interpenetrating networks) exist in the midsection or body of the capsule wall, the inner wall surface and the exterior wall surface are generally comprised of wholly polymerized core and matrix phase wall forming materials, respectively.

As noted, oligomerization/prepolymerization and polymerization are initiated by suitable initiators, most especially, in the case of the (meth)acrylate monomers, oligomers and prepolymers, free radical initiators. The specific selection of the initiators is dependent, in part, upon the monomers, oligomers and/or prepolymers to be polymerized or further oligomerized as well as the method by which the initiator is activated: in the case of free radical initiators, the method by which the free radical is to be generated, e.g., heat, actinic radiation, etc. Latent initiators are also contemplated where a first action, particularly a chemical reaction, is needed to transform the latent initiator into an active initiator which subsequently initiates polymerization upon exposure to polymerizing conditions. Where multiple initiators are present, it is contemplated, and preferred, that each initiator be initiated or suitably initiated by a different condition. For example, each initiator may be initiated by a different temperature or one may be induced by heat and the other by actinic radiation. The use of different initiators with different activation triggers allows for more control in the capsule wall formation. Depending upon the method of activation, control of oligomerization/prepolymerization and/or wall formation may also be exercised by limiting the time and/or extent of activation, e.g., by exposing the specific reaction mix to sufficient temperatures or to actinic radiation for a limited period of time and/or by increasing the intensity of the activation energy, i.e. increasing the temperature and/or the intensity of the light.

Furthermore, it is to be appreciated that the initiators may be present in different phases in different amounts. For example, an initiator for effecting polymerization of the monomers/oligomers of the first oil phase may be present in either the first or second oil phase composition or both, but is preferably in the first so that the initiator may be activated prior to combining with the second oil phase, which contains the wall forming (meth)acrylate monomers, so as to enhance and/or speed up the polymerization/oligomerization. Additionally, as noted above, an initiator for the wall forming materials of one phase may be in the other phase whereby said initiator helps ensure polymerization at the oil/water interface. This is especially effective where the initiator has a greater affinity for the other phase and tends to concentrate at the interface. Of course such additional initiator is not necessary, especially where there is sufficient initiator in the phase of the wall forming material that it initiates.

Dual Water Phase Microencapsulation

As noted, the dual acrylic/melamine walled microcapsules of the present teaching may also be formed in a wholly aqueous based microcapsule wall forming system employing at least two aqueous phase compositions: one of which comprises a curable, water soluble or water dispersible (meth)acrylate ester composition and the other the water soluble or water dispersible melamine resin composition. As with the oil/water phase dual walled system, it is also possible to form an acrylic core/melamine outer shell microcapsule as well as a melamine core/acrylic outer shell microcapsule. For the sake of convenience and simplicity, the following discussion will focus on the latter; though those skilled in the art will readily recognize and be able to apply the teachings presented herein to form the former.

The dual water phase dual walled microcapsules are typically formed by a sequential microencapsulation process wherein a first shell wall is formed of one of the two wall forming compositions on the dispersed droplets of the core material before that single walled microcapsule is combined with the second water phase wall forming material to form an over-shell or over-layer of the second wall forming material on the previously formed microcapsule: in essence the second wall forming material will encapsulate the microcapsule formed from the first wall forming material. Alternatively, the second water phase wall forming material may be added, in whole or in part, preferably in part, before or concurrent with/during the polymerization of the first wall forming material and polymerized concurrent with the polymerization of the first wall forming material. Here, it is most typical that polymerization of the first water phase wall forming material is initiated prior to initiation of the second water phase wall forming material: though both polymerizations will proceed concurrently until completed.

Generally speaking, in the dual water phase microencapsulation process the water phase (meth)acrylate monomers/oligomers comprise from 5-90, preferably from 10-70, more preferably from 20-50, most preferably from 30-40 weight percent and the melamine resin wall forming materials comprise from 10-95, preferably from 30-90, more preferably from 50-80, most preferably from 60-70 weight percent, based on the total weight of the wall forming materials.

Typically the first step of this process is the preparation of an aqueous medium or matrix in a reactor vessel which will serve as the medium in which the microencapsulation process will take place. Initially the aqueous medium comprising water and select emulsifiers for the microencapsulation process at hand is prepared under moderate mixing at room temperature. Optionally, the aqueous medium may also contain a portion or all of the wall forming materials, including monomer, oligomer and/or prepolymer and initiator. As appropriate, it may be necessary to adjust the pH of the medium to optimize the microencapsulation process. Preferably, the pH is adjusted to 5.8 or thereabouts, typically through the addition of a sodium hydroxide solution.

The second step is the formation of the emulsion of the core material that is to be encapsulated. Here the core material, which comprises or contains the ingredient or other material that is to be encapsulated, is added to the aqueous medium and subjected to high shear mixing or milling, typically ~1200 rpm milling. In many instances the core material itself is an oil, e.g., a scented oil. Additionally, it is also contemplated that one or more of the monomers and/or oligomers of the initial wall forming materials or a portion thereof is added to the aqueous medium just prior to, concurrent with or subsequent to the addition of the core material. The contents of the reactor vessel are subjected to the milling process until the desired particle size is attained, typically 20-30 minutes. Generally, at this point a sample of the emulsion in the making is taken periodically and the particle size determined so as to avoid over-emulsification.

Once the desired emulsion is established and stable, the degree of the mixing is reduced, typically the milling blade is replaced with a conventional mixer blade or other mixer element, and a slower mixing ensued. Thereafter the remaining constituents or ingredients necessary for the formation of the initial shell wall is added to and intimately mixed with the contents of the reactor vessel: these include the wall forming materials or, as appropriate, the balance of the same and may also include additional emulsifiers, etc.

The contents of the reactor vessel are then subjected to conditions which effect polymerization of the wall forming material and the polymerization allowed to continue for several hours until completed or nearly so.

The microcapsules formed in the previous step are then subjected to a second encapsulation process employing another water phase composition comprising the ingredients or constituents of the second wall forming material to be used. Other ingredients, including additional emulsifiers, chain transfer agents, etc. may also be added at this point. In any event, once the second water phase wall forming composition is combined with the reaction mix containing the preformed microcapsules, the mixture is subjected to such conditions as will effect deposition and polymerization of the second wall forming composition on the outer wall of the previously formed microcapsule. This processing is continued until the polymerization is completed and/or the desired wall thickness or microcapsule size is attained.

In yet another embodiment, one may add the second water phase composition comprising the ingredients or constituents of the second wall forming material to the aforementioned emulsion concurrent with or immediately or subsequently following the initiation of the polymerization of the first wall forming materials rather than waiting for several hours or until after completion of the polymerization of the first wall forming materials. In this instance, wall formation occurs simultaneously with the development of an interpenetrating network and/or copolymerization at the interface of the two materials.

As with the dual water/oil microencapsulation process described previously, the all water phase microencapsulation process generalized in the preceding paragraphs may be altered in a variety of ways, changing and/or adding additional ingredients, altering the sequence of steps, etc. Attention is directed to the preceding discussion in relation to the oil/water phase microcapsules as those variations are equally applicable to the water phase only microencapsulation process as well and is not repeated in the interest of expediency.

Having spoken in generalities, the following describes more specifically the preparation of a water phase acrylic/melamine dual walled microcapsule which is produced as follows:

(I) a first water phase composition comprising water, one or more emulsifiers for emulsifying an oil in water is prepared in a reactor vessel at room temperature at a low mixer speed (350 rpm). As necessary, the pH of the first water phase composition is adjusted to a pH of ~5 (5-6) with a suitable material such as sodium hydroxide.

(II) once the first water phase material is formed and essentially stable or homogenous, a portion, ~38% by weight (30-40%), of the melamine wall forming material is slowly added to the reactor vessel with continued mixing. This material is allowed to mix for approximately 20 minutes (15-25 minutes) with constant stirring and the temperature elevated to 53° C. (50° C.-60° C.) and held.

(III) an oil phase core material, i.e., the material to be encapsulated, typically an aromatic oil, is slowly added to the reactor vessel under milling conditions, i.e., high shear mixing, ~1200 rpm until the desired droplet size is attained, approximately 20 (20-60) minutes or so. During this phase, samples are periodically taken from the milling vessel to check droplet size. Once the desired droplet size is attained, the mixing is stopped and the milling blade replaced with a mixing blade.

(VI) a second water phase composition comprising water, the remainder of the water phase melamine resin wall forming materials and an initiator for initiating, accelerating and/or catalyzing the condensation of the melamine resin, which had been previously mixed and heated to 50° C. (50° C.-60° C.) and whose pH has been adjusted to 5.8 (pH 5-6), is then slowly added to the reaction vessel over a period of several minutes and the mixture allowed to mix for several more minutes.

(VIII) a salt, e.g., disodium sulfate, is added to the mixture over a period of a minute or two and the mixture then subjected to higher speed mixing, ~600 rpm.

(IX) the temperature of the reactor vessel in increased to 85° C. and the contents of the reactor vessel allowed to "cook" for a period of 8 hours with continued mixing.

(X) towards the end of the "cooking", a third water phase composition is prepared comprising water and a free radical initiator in a mixing vessel and the contents mixed. As necessary, the pH of the mixture is adjusted to 4.6 (pH 4.5-6) with, e.g., sodium hydroxide, and the mixture heated to a temperature of 60° C. (50-75° C.) and the temperature held for a period of 30 minutes (25-45). Generally, pH is adjusted to aid in solubility of the initiator and/or other component.

(XI) concurrently, a fourth water phase composition is prepared comprising water and the free radical polymerizable (meth)acrylate wall forming monomers/-oligomers.

(XII) the third and fourth water phase compositions are then mixed together at room temperature (20-30° C.) and mixed for a period of 10 minutes after which time they are added to the reaction mixture and the temperature of the mixture is further elevated to 95° C. over a period of 60 minutes and held at that temperature for an additional 6 hours to form the final microcapsules.

The microcapsules formed in accordance with the present teachings may be recovered by conventional methods and employed in conventional applications as well as applications demanding of the specific properties and characteristics of the microcapsules so formed. These microcapsules are especially suitable for use in applications where the microcapsules are subject to erosion or wear and thus require good physical properties to resist premature fracture combined with adequate leakage or release of the contents, especially perfumes, to provide a detectable, to the nose, level of release, without too much release, the latter resulting in poor life to the treatment of the treated products. These microcapsules are especially suited for use in fabric treatments.

Having described the general dual walled microcapsules and their method of manufacture, attention is now given to the critical as well as typical and optional ingredients that may be used and are suitable for use in the practice of the present teachings.

Acrylic Wall Forming Compositions

As noted above, there are two different types of acrylic wall forming compositions that may be used in the practice of the present teachings depending upon the desired microcapsules and methodology for their production: one comprising oil soluble or dispersible (meth)acrylate monomers, oligomers and/or prepolymers and the other water soluble or dispersible (meth)acrylate monomers, oligomer and/or prepolymers. In both instances, the (meth)acrylate may be pre-polymerized to form oligomers/prepolymers of the precursors of each.

Oil Soluble or Dispersible (Meth)acrylates

The (meth)acrylate wall forming components of the oil phase, in the case of a two phase, oil/water, system, comprise either (A)(i) at least one oil soluble or dispersible amine (meth)acrylate, (ii) at least one oil soluble or dispersible acidic (meth)acrylate or at least one oil soluble or dispersible simple acid or both, and (iii) at least one oil soluble or dispersible multifunctional (meth)acrylate monomer or oligomer or (B) (i) at least one oil soluble or dispersible acidic (meth)acrylate, (ii) at least one oil soluble or dispersible simple base, and (iii) at least one oil soluble or dispersible multifunctional (meth)acrylate monomer or oligomer. Although the processes of the present teaching may employ a single composition containing all three of the aforementioned required components or two or more precursor compositions each containing one or more of the aforementioned required components, it is preferred that the process employ a preformed oligomer or prepolymer of said components or that said oligomer or prepolymer be formed in-situ in the course, preferably immediately prior to, the initiation of the actual formation of the shell wall at the interface of the oil and water phases. Where the (meth)acrylate oligomer/prepolymer is formed in-situ as part of the overall microencapsulation process, the oil phase composition will typically comprise at least a first oil phase composition and a second oil phase composition, one of which comprises the combination of (A)(i) at least one oil soluble or dispersible amine (meth)acrylate, (ii) at least one oil soluble or dispersible acidic (meth)acrylate or at least one oil soluble or dispersible simple acid or both, and (iii) at least one oil soluble or dispersible multifunctional (meth)acrylate monomer or oligomer or (B) (i) at least one oil soluble or dispersible acidic (meth)acrylate, (ii) at least one oil soluble or dispersible simple base, and (iii) at least one oil soluble or dispersible multifunctional (meth)acrylate monomer or oligomer and the other an initiator for forming the (meth)acrylate oligomer/prepolymer and, optionally, an initiator, which may be the same or a similar initiator, for effecting polymerization of the so formed (meth)acrylate oligomer/prepolymer to form the microcapsule wall.

Suitable oil-soluble or dispersible amine (meth)acrylates for use in the practice of the present method include, by way of illustration and not limitation, amine modified (meth)acrylate monomers such as mono or diacrylate amines, mono or dimethacrylate amines, amine modified polyetheracrylates, amine modified polyethermethacrylates, aminoalkyl acrylates, aminoalkyl methacrylates and the like. The amines can include primary, secondary or tertiary amines.

Preferably, the amine (meth)acrylate is an aminoalkyl acrylate or aminoalkyl methacrylate including, for example, but not by way of limitation, ethylaminoethyl acrylate, ethylaminoethyl methacrylate, aminoethyl acrylate, aminoethyl methacrylate, tertiarybutyl ethylamino acrylate, tertiarybutyl ethylamino methacrylate, tertiarybutyl aminoethyl acrylate, tertiarybutyl aminoethyl methacrylate diethylamino acrylate, diethylamino methacrylate, diethylaminoethyl acrylate, diethylaminoethyl methacrylate, dimethylaminoethyl acrylate and dimethylaminoethyl methacrylate. More preferably, the amine (meth)acrylate is an aminoethylacrylate or aminoethylmethacrylate, most especially tertiarybutyl aminoethyl methacrylate, because these are readily available and give good results Most preferably, the oil-soluble or dispersible amine acrylate or amine methacrylate corresponds to the formula:

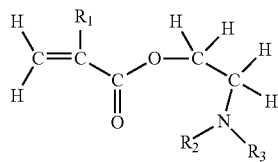

wherein $R_1$ is hydrogen or methyl and each $R_2$ and $R_3$ is independently selected from hydrogen and $C_1$-$C_{12}$ hydrocarbon.

In those instances where an oil soluble or dispersible simple base is to be employed in place of or in addition to the amine (meth)acrylate, the simple base is typically a primary, secondary or tertiary amine or amino compound including, for example, aliphatic amines, cycloaliphatic amines, amidoamines and polyamides. Specific exemplary amines include diethylene triamine, triethylenetetraamine and tetraethylenepentaamine, Lewis bases such as o-(diethylaminoethyl)phenol, tris-(dimethylaminomethyl)phenol and 2-ethyl-4-methyl imidiazole base; and Schiff bases such as methyl anthranilate/citronellal Schiff base, isononylaldehyde/methylanthranilate Schiff base, methyl N-(3,7-dimethyl-7-hydroxyoctylidene)-anthranilate Schiff-base.

Suitable oil-soluble or dispersible (meth)acrylate acids generally correspond to the formula:

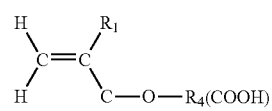

wherein $R_1$ is hydrogen or methyl and $R_4$ is a straight chain or branched $C_1$-$C_{10}$ hydrocarbyl group and the carboxyl moiety, —COOH, is bonded to any of the carbon atoms of the hydrocarbyl group; preferably, the terminal carbon atom. Exemplary acid (meth)acrylates include 2-carboxyethyl acrylate and 2-carboxyethyl methacrylate.

In those instances where an oil soluble or dispersible simple acid is to be employed in place of or in addition to the acid (meth)acrylate, the oil soluble acid is preferably an organic acid. The organic acid can be selected from various acids such as carboxy acids, with monoalkyl maleates such as monomethyl-, monoethyl- or monobutyl-maleate being preferred, with monobutyl maleate being most preferred. Other preferred organic acids include beta-carboxyethyl acrylate. Yet other organic acids that can be usefully employed in the invention include, organic sulfonic acids such as alkyl benzene sulfonic acid, more particularly linear alkyl benzene sulfonic acid, tridecylbenzene sulfonic acid, more particularly linear trialkylbenzene sulfonic acid such as linear tridecylbenzene sulfonic acid, alkyldiphenyloxide sulfonic acid, preferably dodecyl diphenyloxide disulfonic acid, more particularly branched $C_{12}$ diphenyloxide disulfonic acid, alkylbenzene sulfonic acid, more particularly, dodecyl benzene sulfonic acid, dialkylnaphthalene disulfonic acid, more particularly dinonylnaphthalene disulfonic acid, 4-hydrozino benzene sulfonic acid, acrylic acid, methacrylic acid, and the like. Desirably the organic acid is selected to be dispersible in the oil phase and sparingly soluble in the water phase.

Finally, the oil-soluble or dispersible multifunctional (meth)acrylate monomers and oligomers contain two or more double bonds, preferably two or more acrylate or methacrylate functional groups. Suitable monomers and oligomers include, by way of illustration and not limitation, allyl methacrylate; triethylene glycol dimethacrylate; ethylene glycol dimethacrylate; diethylene glycol dimethacrylate; aliphatic or aromatic urethane acrylates, such as hexafunctional aromatic urethane acrylates; ethoxylated aliphatic difunctional urethane methacrylates; aliphatic or aromatic urethane methacrylates, such as tetra-functional aromatic methacrylates; epoxy acrylates; epoxymethacrylates; tetraethylene glycol dimethacrylate; polyethylene glycol dimethacrylate; 1,3 butanediol diacrylate; 1,4-butanediol dimethacrylate; 1,4-butanediol diacrylate; diethylene glycol diacrylate; 1,6 hexanediol diacrylate; 1,6 hexanediol dimethacrylate; neopentyl glycol diacrylate; polyethylene glycol diacrylate; tetraethylene glycol diacrylate; triethylene glycol diacrylate; 1,3 butylene glycol dimethacrylate; tripropylene glycol diacrylate; ethoxylated bisphenol A diacrylate; ethoxylated bisphenol A dimethylacrylate; dipropylene glycol diacrylate; alkoxylated hexanediol diacrylate; alkoxylated cyclohexane dimethanol diacrylate; propoxylated neopentyl glycol diacrylate; trimethylolpropane trimethacrylate; trimethylolpropane triacrylate; pentaerythritol triacrylate; pentaerythritol tetramethacrylate; ethoxylated trimethylolpropane triacrylate; propoxylated trimethylolpropane triacrylate; propoxylated glyceryl triacrylate; ditrimethylolpropane tetraacrylate; dipentaerythritol pentaacrylate; ethoxylated pentaerythritol tetraacrylate; bisphenol A diacrylate; bis-phenol A dimethacrylate, hexafunctional aromatic urethane acrylate; hexa-functional aromatic urethane methacrylate; and the like.

Generally speaking, the make-up of the oligomer/prepolymer of first oil phase composition or, if formed in-situ in the process of the present invention, the combination of reactants in the first oil phase is as follows:

0.1 to 15%, preferably 0.2 to 10%, more preferably 0.4 to 5% by weight of the amine (meth)acrylate and/or simple base;

0.1 to 15%, preferably 0.2 to 10%, more preferably 0.4 to 5% by weight of the acid (meth)acrylate and/or simple acid; and 99.8 to 70%, preferably 99.6 to 80%, more preferably 99.2 to 90% of the multifunctional (meth)acrylate:

provided that when the simple base or the simple acid is present it is also employed in a mole ratio of from 5:1 to 1:5, preferably 3:1 to 1:3, of the acid to amine (meth)acrylate or of the base to acid (meth)acrylate.

When the (meth)acrylate oligomer/prepolymer is formed in-situ as a part of the overall microencapsulation process, the oil phase composition, will comprise a mixture of the specified monomers and, if present, oligomers which are then subjected to such conditions as will effect polymerization thereof. If necessary, though preferably, an initiator is added to the mixture, typically as part of another oil phase composition or component, which initiator is then activated to initiate polymerization of the monomers and, if present, oligomers. For example, in the case of a free radical initiator, the mixture is subjected to such conditions as will generate sufficient free radicals to effect the desired oligomerization/pre-polymerization. Once initiated, polymerization is allowed to proceed for only a set period of time to form the (meth)acrylate oligomer/prepolymer, but not long enough to (a) complete polymerization or (b) form high molecular weight polymers which are incapable of moving within oil phase in which they are solubilized or dispersed and/or fail to stay in solution. Generally speaking, the molecular weight of the preformed or in-situ formed meth(acrylate) oligomer/prepolymer is less than 1,000,000, preferably less than 500,000. Most preferably, these oligomers/prepolymers have a molecular weight of from 5,000 to 200,000, more preferably 10,000 to 100,000. Polymerization may be stopped by removing the conditions that induce or activate the initiator. If present, the amount of the initiator will be from 0.1 to 10%, preferably 0.1 to 6%, more preferably 0.5 to 2.5% by weight based on the weight of the oil phase.

Water Soluble or Dispersible (Meth)acrylates

Alternatively, as noted, the shell wall may comprise an acrylic polymer derived from water soluble or dispersible (meth)acrylate monomer, oligomers and/or prepolymers. Those skilled in the art will readily recognize and appreciate that many of the acrylate monomers and oligomers disclosed above for use in the oil phase will have some water solubility or water dispersability, particularly in the presence of a suitable emulsifier and/or other solubilizer or by suitable elevated temperature and/or pH adjustment, and may be used in forming suitable aqueous based (meth)acrylic ester wall forming compositions. Similarly, they will recognize and appreciate other (meth)acrylic esters that possess water solubility, even low water solubility, and/or water dispersibility so as to be suitable for use in the practice of the present teachings.

Generally speaking, suitable water soluble and/or dispersible (meth)acrylate monomers and low molecular weight oligomers contain at a least one acrylate or methacrylate group and comprise a hydrocarbon portion that is small relative to the whole of the monomer or oligomer such that the ester functional group is enough to impart sufficient hydrophilicity to the monomer, as is the case with, for example, 1,3-butanediol diacrylate. In the case of higher molecular weight monomers, oligomers and/or prepolymers these monomers, oligomers and/or prepolymers will have a sufficient number of acrylate and/or methacrylate groups and/or, again, comprise a relatively small hydrocarbon portion relative to the whole of the monomer, oligomer and/or prepolymer to impart sufficient hydrophilicity thereto. Otherwise, the hydrophobicity of the larger hydrocarbon portion of larger acrylate ester monomers, oligomers and/or prepolymers may be overcome by the presence of additional functional groups such as amines, urethanes, alcohols or ethers or combinations thereof which enhance the hydrophilicity. Exemplary water soluble or dispersible acrylates or methacrylates include amine modified polyether (meth)acrylate oligomers, hexafunctional aromatic urethane (meth)acrylate oligomers, hydroxyethyl (meth)acrylate, hydroxypropyl (meth)acrylate, methyl methacrylate, butanediol di(meth)acrylate, hexanediol di(meth)acrylate, ethoxylated bisphenol-A diacrylate, ethoxylated bisphenol-A dimethacrylate, isobornyl (meth)acrylate, pentaerythritol tri(meth)acrylate, pentaerythritol tetra(meth)acrylate, penta(meth)acrylate ester, diethylene glycol di(meth)acrylate, dipropylene glycol di(meth)acrylate, triethylene glycol di(meth)acrylate, tripropylene glycol di(meth)acrylate, neopentyl glycol di(meth)acrylate, trimethylolpropane tri(meth)acrylate, methoxy polyethylene glycol mono(meth)acrylate, ethoxylated trimethylolpropane tri(meth)acrylate, and ethoxylated pentaerythritol tetra(meth)acrylate, difunctional aliphatic epoxy (meth)acrylates, polyethylene glycol di(meth)acrylate, polypropylene glycol di(meth)acrylate, alkoxylated mono- or multi-functional (meth)acrylate ester, polyester (meth)acrylate oligomers, amine modified polyether (meth)acrylate oligomers and the like. Especially preferred water soluble or water dispersible (meth)acrylates are the polyethylene glycol di(meth)acrylates, ethoxylated mono- or multi-functional (meth)acrylates, and (meth)acrylate monomers and/or oligomers that are capable of being dispersed in water with a small amount of a suitable emulsifier and/or solubilizer.

Though the foregoing discussion mostly describes various acrylic monomers and oligomers, acrylic prepolymers and low molecular weight polymers, including co-polymers, are also suitable. For example, the acrylic component may be a polyacrylic acid or a copolymer of acrylic acid and an alkyl acrylate. The alkyl acrylate can be selected such that the alkyl moiety is from about one to twelve and preferably from one to eight carbons. Examples of such alkyl acrylates include methyl acrylate, ethyl acrylate, propyl acrylate, butyl acrylate, pentyl acrylate, hexylacrylate, cyclohexyl acrylate, 2-ethylhexyl acrylate and the like. A preferable copolymer was 90% polyacrylic acid and 10% butyl acrylate. Exemplary acrylic polymers include Colloid 121 and Colloid 351 from Rhone Poulenc.

Although 100% of the water phase (meth)acrylate may be one or more multi-functional (meth)acrylate monomers/oligomer or one or more mono- and/or di-functional (meth) acrylate monomers/oligomers, generally speaking the water phase (meth)acrylate wall forming composition comprises from 10-95, preferably 20-85, more preferably, 35-70, most preferably 50-65 weight percent of the one or more multi-functional (meth)acrylate monomers and/or oligomers and from 5-90, preferably 15-85, more preferably 30-65, most preferably 35-50 weight percent of a the one or more mono- and/or di-functional, preferably or predominately di-functional, (meth)acrylate monomer and/or oligomer, based on the total weight of the water phase (meth)acrylate wall forming material. These water phase (meth)acrylate wall forming materials, both in terms of chemical make-up and formulation (i.e., relative weight percent) are also disclosed in U.S. Provisional Patent Application No. 62/064,906 filed on Oct. 16, 2014, the contents of which are hereby incorporated by reference.

Melamine Resin

The second critical wall forming material is the melamine resin prepolymer or the precursors therefore. Microcapsule wall forming melamine prepolymers and precursors therefore are well known and widely available. These include, for example, melamine-based polyureas, melamine-formaldehyde resins, melamine-aldehyde resins, dimethylol melamine urea, methylated dimethylol melamine urea, methylated melamine formaldehyde, methylated methylol melamine, and mixtures of melamine formaldehyde with urea formaldehyde. Encapsulations based on polymerization of melamine-urea and formaldehyde, monomeric or low molecular weight polymers of dimethylol urea or methylated dimethylol urea, melamine and formaldehyde, methylated melamine formaldehyde, monomeric or low molecular weight polymers of methylol melamine or methylated methylol melamine, as taught in U.S. Pat. No. 4,552,811 (which is hereby incorporated herein by reference) are preferable.

Though a wide variety of melamine prepolymers and precursors are suitable for use in the practice of the present teachings, especially preferred melamine prepolymers and precursors are those that are formaldehyde free and/or those of the methylated melamine resins that are wholly or partially soluble in water, most especially the partially methylated and high imino methylated melamine resins. These preferred melamine prepolymers are reactive with hydroxyl, carboxyl and amid functional groups of other monomers, oligomers, prepolymers and/or polymers. Most importantly, it is especially desirable in the preferred embodiments that the melamine prepolymers are capable of self-condensation to form their own polymers and more preferably have a moderate to high tendency to self-condensate. Though not required, polymerization of these melamine prepolymers is aided by acid catalysis. Of these preferred melamine prepolymers, their functionality is predominately methoxymethyl and methylol in the case of the partially methylated melamines and methoxymethyl and imino in the case of the methylated high imino melamines. These melamine resins are also well known and widely available. Exemplary resins include those available from Allnex USA, Stamford, Conn. including those sold under the tradename Cymel such as Cymel 328, Cymel 385 and Cymel 373.

Core Ingredient

The microcapsules of the present teaching include a core material which comprises one or more ingredients that are intended to be encapsulated. The core material are selected from a number of different materials such as chromogens and dyes, flavorants, perfumes, sweeteners, fragrances, oils, fats, pigments, cleaning oils, pharmaceuticals, pharmaceutical oils, perfume oils, mold inhibitors, antimicrobial agents, adhesives, phase change materials, scents, fertilizers, nutrients, and herbicides: by way of illustration and without limitation. The core material can be a liquid or a solid. With cores that are solid at ambient temperatures, the wall material can usefully enwrap less than the entire core for certain applications where availability of, for example, an agglomerate core is desired on application. Such uses can include scent release, cleaning compositions, emollients, cosmetic delivery and the like. Where the microcapsule core is phase change material, uses can include such encapsulated materials in mattresses, pillows, bedding, textiles, sporting equipment, medical devices, building products, construction products, HVAC, renewable energy, clothing, athletic surfaces, electronics, automotive, aviation, shoes, beauty care, laundry, and solar energy.

The core material can be a minor or major constituent of the material encapsulated by the microcapsules. Typically, particularly when the core material is a liquid material, the core material is combined with one or more of the compositions from which the internal wall of the microcapsule is formed. For example, if the microcapsule has a (meth) acrylic inner wall formed of two oil phase compositions, the core material will be combined with one or the other of such compositions or a portion of the core material may be present in each. If the core material can function as the oil solvent in the capsules, e.g. acts as the solvent or carrier for the wall forming materials, it is possible to make the core material the major or total material encapsulated. Usually however, the core material is from 0.01 to 99 weight percent of the capsule internal contents, preferably 0.01 to about 65 by weight of the capsule internal contents, and more preferably from 0.1 to about 45% by weight of the capsule internal contents. With certain applications, the core material can be effective even at just trace quantities.

Oil Phase Carriers and Solvents

Where the core material is not itself sufficient to serve as the oil phase or solvent, particularly for the wall forming materials, the oil phase will further include a suitable carrier and/or solvent. These carriers or solvents preferably have a boiling point greater than 100° C. and low volatility and are non-flammable. Though not limited thereto, they preferably comprise one or more esters, preferably with chain lengths of up to 18 carbon atoms or even up to 42 carbon atoms and/or triglycerides such as the esters of $C_6$ to $C_{12}$ fatty acids and glycerol. Exemplary carriers and solvents include, but are not limited to: ethyldiphenylmethane; butyl biphenyl ethane; benzylxylene; alkyl biphenyls such as propylbiphenyl and butylbiphenyl; dialkyl phthalates e.g. dibutyl phthalate, dioctylphthalate, dinonyl phthalate and ditridecylphthalate; 2,2,4-trimethyl-1,3-pentanediol diisobutyrate; alkyl benzenes such as dodecyl benzene; alkyl or aralkyl benzoates such as benzyl benzoate; diaryl ethers; di(aralkyl)ethers and aryl aralkyl ethers; ethers such as diphenyl ether, dibenzyl ether and phenyl benzyl ether; liquid higher alkyl ketones (having at least 9 carbon atoms); alkyl or aralkyl benzoates, e.g., benzyl benzoate; alkylated naphthalenes such as dipropylnaphthalene; partially hydrogenated terphenyls; high-boiling straight or branched chain hydrocarbons; alkaryl hydrocarbons such as toluene; vegetable and other crop oils such as canola oil, soybean oil, corn oil, sunflower oil, cottonseed oil, lemon oil, olive oil and pine oil; methyl esters of fatty acids derived from transesterification of vegetable and other crop oils, including those mentioned previously; methyl ester of oleic acid; esters of vegetable and other crop oils, e.g. soybean methyl ester; straight chain saturated paraffinic aliphatic hydrocarbons of from 10 to 13 carbons, and the like. Mixtures of the above can also be employed. Common diluents such as straight chain hydrocarbons can also be blended with the solvents, or blend of solvents. In those cases where the inner wall of the microcapsule is oil-based derived, the solvent is typically selected on the basis of their hydrophobicity and their ability to disperse or solvate the wall forming monomers and/or prepolymer of the oil phase.

Emulsifier

Optionally, though preferably, where microencapsulation process involves a water phase-oil phase system, the water phase composition or, in the case of microcapsules prepared from two or more water phase compositions, one or both of said water phase compositions will contain an emulsifier to aid in the creation of the dispersion of the oil phase in the continuous water phase or, as appropriate, the water phase in the continuous oil phase. Similarly, where dual water phase wall forming materials are employed an emulsifier is employed to disperse the core material, which is typically an oil or oil phase material, in that water phase. Less critical, but again, preferably, an emulsifier, preferably a non-ionic emulsifier, is added to one or both water phase compositions to aid in the dispersion and/or solubility of the water soluble or dispersible acrylate monomer or oligomer and/or the melamine resin, as appropriate.

Emulsifiers of all types are suitable for use in the practice of the present invention though it is to be appreciated, and those skilled in the art will readily recognize, that different systems, e.g., different first oil phase compositions and/or core material, will be better suited with one or more classes of emulsifiers than others. Specifically, while the present teachings are applicable to anionic, cationic, non-ionic and amphoteric emulsifiers generally, preferred emulsifiers are the cationic and non-ionic emulsifiers, particularly those having polyalkylether units, especially polyethylene oxide units, with degrees of polymerization of the alkylene ether unit of greater than about 6. Preferred emulsifiers are those which significantly reduce the interfacial tension between the aqueous phase and dispersed phase, and thereby reduce the tendency for droplet coalescence. In this regard, generally the emulsifiers for use in the first water phase for aiding in the oil in water emulsion or dispersion will have HLB values of from 11 to 17. While emulsifiers of the same HLB value may also be used in the second water phase, those emulsifiers that are used to enhance the solubility and/or dispersibility of the water phase (meth)acrylate in the second water phase will generally have HLB values of 16 to 20. Of course, emulsifiers/surfactants of lower and higher HLB values that achieve the same objective as noted are also included.

Exemplary anionic surfactants and classes of anionic surfactants suitable for use in the practice of the present invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of $C_{12}$ to $C_{15}$ alkanols or polyalkoxylated $C_{12}$ to $C_{15}$ alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sulfoalkylamides and salts thereof such as N-methyl-N-oleoyltaurate Na salt; polyoxyalkylene alkylphenol carboxylates; polyoxyalkylene alcohol carboxylates alkyl polyglycoside/alkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyaryiphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester; calcium alkylbenzene sulfonate; ethoxylated tridecylalcohol phosphate ester; dialkyl sulfosuccinates; perfluoro ($C_8$-$C_{18}$)alkyl phosphonic acids; perfluoro($C_6$-$C_{18}$)alkylphosphinic acids; perfluoro($C_3$-$C_{20}$)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Exemplary amphoteric and cationic emulsifiers include alkylpolyglycosides; betaines; sulfobetaines; glycinates; alkanol amides of $C_8$ to $C_{18}$ fatty acids and $C_8$ to $C_{18}$ fatty amine polyalkoxylates; $C_{10}$ to $C_{18}$ alkyldimethylbenzylammonium chlorides; coconut alkyldimethylaminoacetic acids; phosphate esters of $C_8$ to $C_{18}$ fatty amine polyalkoxylates;

alkylpolyglycosides (APG) obtainable from an acid-catalyzed Fischer reaction of starch or glucose syrups with fatty alcohols, in particular $C_8$ to $C_{18}$ alcohols, especially the $C_8$ to $C_{10}$ and $C_{12}$ to $C_{14}$ alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable non-ionic emulsifiers are characterized as having at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; $C_8$ to $C_{22}$ alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; polyaryl phenols; sorbitol ester alkoxylates; and mono- and diesters of ethylene glycol and mixtures thereof; ethoxylated tristyrylphenol; ethoxylated fatty alcohol; ethoxylated lauryl alcohol; ethoxylated castor oil; and ethoxylated nonylphenol; alkoxylated alcohols, amines or acids; amides of fatty acids such as stearamide, lauramide diethanolamide, and lauramide monoethanolamide; long chain fatty alcohols such as cetyl alcohol and stearyl alcohol; glycerol esters such as glyceryl laurate; polyoxyalkylene glycols and alkyl and aryl ethers of polyoxyalkylene glycols such as polyoxyethylene glycol nonylphenyl ether and polypropylene glycol stearyl ether. Polyethylene glycol oligomers and alkyl or aryl ethers or esters of oligomeric polyethylene glycol are preferred. Also preferred as non-ionic emulsifiers are polyvinyl alcohol, polyvinyl acetate, copolymers of polyvinyl alcohol and polyvinylacetate, carboxylated or partially hydrolyzed polyvinyl alcohol, methyl cellulose, various latex materials, stearates, lecithins, and various surfactants. It is known that polyvinyl alcohol is typically prepared by the partial or complete hydrolysis of polyvinyl acetate. Accordingly, by reference to polyvinyl alcohol we intend to include both completely and partially hydrolyzed polyvinyl acetate. With respect to the latter, it is preferred that the polyvinyl acetate be at least 50 mole % hydrolyzed, more preferably, at least 75 mole % hydrolyzed.

Where the emulsifier is a polymeric emulsifier, especially one having or derived from an acrylic ester, e.g., a polyacrylate, the molecular weight is generally at least 10,000, preferably at least 20,000, most preferably 30,000 or more. Additionally, the amount of emulsifier is typically from about 0.1 to about 40% by weight, more preferably from about 0.2 to about 15 percent, most preferably from about 0.5 to about 10 percent by weight based on the total weight of the formulation. It is to be appreciated that certain acrylic polymers and copolymers may perform both as an emulsifier as well as a polymerizable and/or non-polymerizable component in forming the microcapsule wall. With respect to the latter, the polymeric emulsifier, particularly those in the nature of higher molecular weight polymers, are trapped and/or incorporated into the polymer wall as it is formed. This is especially likely where the nature of the water phase changes and the solubilized polymer comes out of solution.

Chain Transfer Agents

Optionally, though preferably, at least one of the water phase compositions, particularly the second water phase composition, i.e., that added to the first, as discussed more clearly below, further includes at least one chain transfer agent. Suitable chain transfer agents include, for example, lower alkyl alcohols having from 1 to 5 carbon atoms, mercaptoethanol, mercaptopropanol, thioglycolic acid, isooctylmercaptoproprionate, tert-nonylmercaptan, pentaerythritol tetrakis(3-mercapto-proprionate), dodecylmercaptan, formic acid, halogenated hydrocarbons, such as bromoethane, bromotrichloromethane, or carbon tetrachloride, and the sulfate, bisulfate, hydrosulfate, phosphate, monohydrogen phosphate, dihydrogen phosphate, toluene sulfonate, and benzoate salts of sodium and potassium, especially sodium hypophosphite and sodium bisulfate. If present, the chain transfer agents are preferably used in amounts ranging from 0.01 to 5%, preferably from 0.5 to 3%, by weight with respect to the monomers and/or oligomers employed.

Initiators

Suitable initiators for effecting polymerization of the various (meth)acrylate monomer, oligomers and/or prepolymers may be added to or present in both the oil phase and the water phase compositions. Preferably, an initiator is present in the second oil phase composition, which is free of the aforementioned oil phase (meth)acrylate monomers, oligomers and prepolymers. Similarly, at least one initiator is also present in the first water phase, which is free of the aforementioned water soluble or water dispersible (meth) acrylate monomers and/or oligomers. In both instances it is desirable to add the initiator to the (meth)acrylate-free compositions so as to avoid unwanted or unintended polymerization. By keeping the two separate, one has better control over when polymerization is to begin, particularly in processes, like the instant, where conditions may give rise to activation of the initiator before desired.

Selection of the initiator is dependent, in part, upon the monomers, oligomers and/or prepolymers to be polymerized or further oligomerized, the method by which the initiator is activated, and whether the initiator is to be present in the oil phase or the water phase. Generally speaking, the preferred initiators are energy activated free radical initiators meaning that they generate free radicals when subjected to heat or other energy input. Preferred free radical initiators include peroxy initiators, azo initiators, peroxides, and compounds such as 2,2'-azobismethylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis (isobutylnitrile), 2,2'-azobis(2,4-dimethylpentane-nitrile), 2,2'-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1'-azobis(cyano-cyclohexane), benzoyl peroxide, decanoyl peroxide; lauroyl peroxide; benzoyl peroxide, di(n-propyl) peroxydicarbonate, di(sec-butyl) peroxydicarbonate, di(2-ethylhexyl) peroxydicarbonate, 1,1-dimethyl-3-hydroxybutyl peroxyneodecanoate, .alpha.-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di-t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like.

Suitable water soluble initiators include the persulfate salts, such as ammonium persulfate, sodium persulfate and potassium persulfate; peroxides, such as hydrogen peroxide, oxalic acid peroxide, acetic acid peroxide and succinic acid peroxide; and various water soluble azo compounds such as those represented by the formulas:

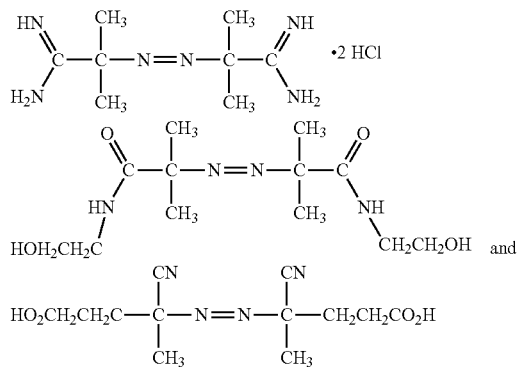

In the case of initiators to be used in the water phase, water soluble azo compounds are preferred because they have good decomposition temperatures.

As noted above, actinic radiation activated initiators are also contemplated and desirable. Suitable actinic radiation activated initiators include those activated by UV light, IR radiation, visible light, electron beam and the like. Actinic radiation activated initiators can be used in place of, in whole or in part, heat activated initiators. For example, it may be desirable to use heat initiators for one or more polymerization steps and an actinic radiation activated initiator for one or more other polymerization steps.

Preferred actinic radiation activated initiators are the UV initiators. Exemplary UV initiators include benzophenone; acetophenone; benzil; benzaldehyde; o-chlorobenzaldehyde; xanthone; thioxanthone; 9,10-anthraquinone; 1-hydroxycyclohexyl phenyl ketone; 2,2-diethoxyacetophenone; dimethoxyphenylacetophenone; methyl diethanolamine; di methylaminobenzoate; 2-hydroxy-2-methyl-1-phenylpropane-1-one; 2,2-di-sec-butoxyacetophenone; 2,2-dimethoxy-1,2-diphenylethan-1-one; dimethoxy-ketal; phenyl glyoxal 2,2'-diethoxyacetophenone; hydroxycyclohexyl phenyl ketone; alpha-hydroxyketones; alpha-amino-ketones; alpha and beta naphthyl carbonyl compounds; benzoin ethers such as benzoin methyl ether; benzil; benzil ketals such as benzil dimethyl ketal; acetophenone; fluorenone; 2-hydroxy-2-methyl-1-phenylpropan-1-one, and the like. UV initiators of this kind are available commercially, e.g., IRGACURE 184 or DEGACURE 1173 from Ciba. Thermal initiators are available from DuPont.

As noted above, actinic radiation activated initiators, preferably UV initiators, can be employed in addition to and/or as an alternative to heat activated initiators. The presence of both a heat activated initiator and actinic radiation activated and initiator results in a dual cure system or one that provides an optional thermal or optional light or optional UV initiated cure method. Given the selectivity of certain initiators for polymerizing certain monomers, oligomers and/or prepolymers, one can tailor their encapsulation process to effect polymerization in only one phase as opposed to multiple phases and/or polymerization of one or more monomers but not all free radically curable or polymerizable monomers. Furthermore, given the half-lives of certain of the free radical initiators, one is able to better control the extent or degree of polymerization so as to prevent too much cure too early in the encapsulation process. Similarly, one can employ different temperatures for different polymerization steps to regulate the rate of polymerization, again to better control the formation of the capsule wall and its constituents. For example, in preparing the oil phase oligomer/prepolymer one may use a heat activated initiator at one temperature and the same or a different initiator at a higher temperature to effect the further polymerization thereof in forming the capsule wall. Additionally, it is possible to employ three different polymerization temperatures in the encapsulation process where the first, preferably the lower temperature, is employed to prepare the oil phase (meth)acrylate oligomer/prepolymer. A second higher temperature is employed to initiate wall formation through polymerization of the oil phase (meth)acrylate oligomer/ prepolymer or of the water soluble or water dispersible (meth)acrylate monomers and/or oligomers, or both. And, a final, yet higher still, temperature to fully cure or polymerize the capsule wall material. Again, as noted, one may substitute a non-heat activated initiator for the heat activated initiator in any one or more of these polymerization steps and/or add a non-heat activated initiator which is specific for said one or more of the foregoing polymerization steps.

In a yet further embodiment, for specialized microencapsulation processes, the use of initiators, e.g., thioxanthones, phosphine oxides, metallocenes, tertiary aminobenzenes or tertiary aminobenzophenones, which break down into free radicals on exposure to visible light is effectively used. Such microencapsulation systems however typically require special handling of the system to prevent premature polymerization or oligomerization by appropriate control of lighting conditions.

In general, the initiator will be present in an amount of 0.01 to 10.0 weight percent, preferably 0.1 to 6 weight percent, more preferably 0.5 to 2.5 weight percent, in any of the water or oil phases, based on the total weight of all constituents. Preferably, though, somewhat lower levels of UV initiators may be used, e.g., from 0.1-2.5 weight percent, preferably 0.5-1.0 weight percent, UV initiator, based on total weight of the phase in which it is present.

Initiators are available commercially, such as Vazo initiators, which typically indicate a decomposition temperature for the initiator. Preferably the initiator is selected to have a decomposition point of about 50° C. or higher. Blends of initiators can also be employed and are desirable. Usefully, multiple initiators are employed, either as a blend in the oil phase, or in either of the oil or water phases or both. When a blend or combination of initiators is employed they are selected so as to stagger the decomposition temperatures to coincide with the various steps of the capsule wall formation: e.g., pre-polymerization, wall formation and hardening or polymerizing of the capsule wall material. For example, the oil phase can contain a first initiator that decomposes at 55° C. and is selected to promote the oil phase (meth) acrylate oligomer/prepolymer formation, the oil phase may also contain a second initiator, one that decomposes at 65° C. which aids in polymerization of the aforementioned oil phase (meth)acrylate oligomer/prepolymer to initiate forming the capsule wall material. Optionally, a third initiator may be contained in the oil phase or present in the water phase that decomposes at 85° C. and which facilitates polymerization or full cure of the capsule wall material. The amount of each initiator can be typically as low as 0.1 weight percent or as high as 10 weight percent.

By proper selection of the initiators and the amount by which they are used and/or the time for which they are exposed to the conditions which generate the free radicals, it is possible to effect control or more control over the wall formation process and, in turn, the thickness and properties of the capsule wall. For example, one may use little or less initiator in the second oil phase composition so as to avoid excess oligomerization or prepolymerization of the oil phase (meth)acrylate monomers and oligomers. Alternatively and/or in addition thereto, one may terminate and/or alter the conditions that decompose the initiator so as to stop or at least slow down the generation of free radicals to likewise stop the polymerization process.

Although the foregoing discussion is made with respect to heat activated initiators, it is to be appreciated that the same properties and capabilities apply if the initiators or at least one of a combination of initiators is actinic radiation activated. Here, initiators that are responsive to different wavelengths of actinic radiation can be used to provide the same effect as the use of initiators of different decomposition temperatures. Additionally, one may use a combination of heat activated and actinic radiation activated initiators. As noted above, one can control the speed of polymerization by controlling the rate of free radical generation. This can be attained by raising or lowering the temperature of the reaction mix above or below the 10 hour half-life temperature of the heat activated free radical initiator or increasing or decreasing the intensity of the actinic radiation in the case of actinic radiation activate free radical initiators. Furthermore, it is to be appreciated that if concern exists for the presence of excess initiator following wall formation, one may continue to subject the mix or the capsules to those conditions that decompose the excess initiator until such material is consumed.

While the foregoing has presented a brief outline and description of those critical components or ingredients as well as many of the various co-ingredients and optional ingredients that are typically employed, those skilled in the art will readily appreciate and recognize other components or ingredients that may be employed in addition to those mentioned above, either as an active, reactive or in-active component. For example, other ingredients may be added to help adjust or maintain pH, to prevent agglomeration of the dispersed droplets of the emulsions, to stabilize the emulsions, to inhibit premature polymerization, to accelerate polymerization, etc. Such ingredients are well known and conventional in the microencapsulation art.

Having described the present process in general and specific terms, attention is now directed to the following specific examples which demonstrate the marked benefit of the present process and of the microcapsules resulting therefrom.

EXAMPLES

A plurality of microencapsulation processes were performed, most embodying the process of the present disclosure and a few omitting one or more steps and/or compositions/critical ingredients. Additionally, many of the so formed microcapsules were subjected to a plurality of tests as follows.

Test Methods

Several test methodologies were performed on the microcapsules of the present invention pertinent to the utility thereof in various applications, most especially in fabric treatment applications. These test methods were for determining free oil, static smudge, leakage and fracture strength and deformation.

Free Oil

The amount of free perfume oil in the water phase was determined by GC analysis using as an internal standard solution 1 mg/ml dibutyl phthalate (DBP)/hexane. Samples were prepared by combining approximately 1.5-2 grams (40 drops) of the capsule slurry with 10 ml of the DBP/hexane solution in a 20 ml scintillation vial and capping tightly. The sample was then shaken vigorously several times over 30 minutes before being pipetted into an autosampler vial and analyzed by GC using an HP5890 GC connected to HP Chem Station Software: Column: 5 m×0.32 mm id with 1 μm DB-1 liquid phase, Temp: 50° C. for 1 minute then heat to 320° C. @15 deg/min, Injector: 275°, Detector: 325° C., 2 ul injection. The % free oil was calculated by dividing the mg of free perfume oil measured by the sample weight (mg) and multiplying by 100.

Static Smudge

Static smudge determines the strength of the perfume microcapsules as a function of percent capsule breakage. A series of standards were prepared using dibutylphthalate in either hexane or reagent alcohol as follows: Reference 1=0.5-1.0 mg; Reference 2=5.0-8.0 mg; Reference 3=10.0-15.0 mg. Test samples were prepared by diluting the capsule slurry to 0.1% solids and measure out 920 μL into a small plastic beaker. The sample is then filtered using Millipore express filters under vacuum (part number HPW02500) and the filter paper allowed to dry for 30 minutes. Thereafter a drop of distilled water is applied to the top of the filter apparatus and another clean filter placed on top. The sample is then placed between 2 bond circles which had been cut using a Fiskars Medium Squeeze Punch, model number 12-7436, and the sample inverted and placed on top of the diaphragm of a Mullen tester: the diaphragm being below the hole. On the Mullen Tester, the sample is subjected to 200 psi pressure for 30 seconds and removed. The sample is then placed in a clean 20 mL scintillation vial, pinched slightly in order for solvent to flow freely during extraction. 10 ml of the Hexane/DBP Internal standard solution is added to the vial and the vial capped and shaken well. The sample is allowed to sit for 10 minutes, shaking once at approx. 5 minutes, following which a portion is pipetted into a GC vial to which 10 mL of Reagent Alcohol/DBP solution is added and the contents shaken well. The vial is placed in a 70° C. water bath for 30 minutes and shaken once at approx. the 15 minute mark. After 30 minutes the vial is removed from the bath, shaken well, and allowed to cool to room temperature. When cooled, the solution is pipetted into a clean GC vial and analyzed by GC using an HP5890 GC connected to HP Chem Station Software: Column: 5 m×0.32 mm id with 1 μm DB-1 liquid phase, Temp: 50° C. for 1 minute then heat to 320° C. @15 deg/min, Injector: 275° C., Detector: 325° C., 2 ul injection. Static Smudge is calculated by dividing the mg of perfume oil in the hexane by the sum of the mg of perfume oil in hexane and in the reagent alcohol and multiplying by 100.

Hexane Leakage

The porosity/barrier integrity of the capsule walls was determined by measuring the total perfume oil that was extracted into a hexane phase over periods of 24 hours, 1 week, 2 weeks and 4 weeks. Samples were prepared by vigorously shaking the microcapsule slurry to ensure homogeneous mixing of the material and then extracting a predetermined amount which is then added to a 150 mL jar containing 47 mL of de-ionized water. 50 mL of a 1 mg/ml dibutylphthalate in hexane solution is gently added to the aqueous suspensions, without swirling or shaking, and the sample capped tightly. Aliquots were then taken from the upper hexane layer at t=24 hours, 1 week, 2 weeks and 4 weeks and analyzed by GC using an HP5890 GC connected to HP Chem Station Software: Column: 5 m×0.32 mm id with 1 μm DB-1 liquid phase, Temp: 50 deg for 1 minute then heat to 320 deg @15 deg/min, Injector: 275° C., Detector: 325° C., and 2 ul injection. Percent leakage was determined by dividing the mg of perfume oil detected in the hexane by the total theoretical weight of the perfume oil, multiplied by 100.

Fracture Strength and Deformation

Fracture strength and deformation of the microcapsules were determined using a Hysitron nanoindentation instrument. Samples were prepared by diluting a drop of the microcapsule slurry in 100 g DI water and then applying 2 drops of the diluted slurry to glass slides, spreading the slurry evenly on the slide. The slides were then placed into the Tappi room for at least four hours before testing to determine both fracture strength and fracture displacement. Fracture strength, the force needed to rupture the capsules, is determined as 1.27×Fracture force/(Capsule size)$^2$. Fracture displacement, the percent deformation at rupture, is determined as fracture displacement/capsule size×100.

Table 1 sets forth the ingredient list of key ingredients employed in the examples.

TABLE 1

| Code | Description |
| --- | --- |
| Captex 355 | Medium chain triglyceride based on caprylic and capric acids |
| CD9055 | 2-carboxyethylmethacrylate |
| Colloid 121 | polyacrylic acid emulsifier |
| Colloid 351 | copolymer of 92% acrylic acid and 8% butyl acrylate emulsifier |
| CN975 | Hexafunctional aromatic urethane acrylate oligomer |
| Cymel 385 | methylated high imino melamine resin with a low degree of alkylation |
| RO/DI | Reverse osmosis/deionized water |
| EH | Ethyl Heptanoate |
| IPM | Isopropyl myristate - perfume diluent |
| NaOH | Sodium hydroxide (21.5%) |
| NaS | sodium sulfate (5%) |
| NaHS | Sodium bisulfate (5%) |
| PO | Peppermint oil |

TABLE 1-continued

| Code | Description |
| --- | --- |
| SR9035 | 15 mol ethoxylated trimethylolpropane triacrylate |
| SR444 | Pentaerythritol triacrylate |
| SR601 | Ethoxylated (4) bisphenol A diacrylate |
| TBAEMA | Tertiary-butylaminoethyl methacrylate |
| V-67/Vazo-67 | 2,2'-azobis(2-methylbutyronitrile) - 10 hour ½ life at 67° C. |
| V-501/Vazo-501 | 4,4'-azobis(4-cyanovaleric acid) - 10 hour ½ life at 69° C. |
| V-50 | 2,2'-Azobis(2-methylpropionamidine)dihydrochloride - 10 hour ½ life at 56° C. |
| PFO | Perfume Oil |

Comparative Example 1—MF Single Wall

A first water phase was prepared by combining 17.5 g Colloid 351 (copolymer of 92% acrylic acid and 8% butyl acrylate available from Rhone-Poulenc, Cedex, France), 17.5 g Colloid 121 (polyacrylic acid available from Rhone-Poulenc, Cedex, France), and 200 g DI water in a reactor. The pH was adjusted to 5.9 with 7.4 g of 21.5% aqueous sodium hydroxide. The mixture was stirred and 7.5 g Cymel 385 (a methylated high imino melamine resin with a low degree of alkylation available from Allnex Co., Brussels, Belgium) was added dropwise over one minute. The core material, a mixture of 120 g peppermint oil and 80 g Captex 355 (a triglyceride manufactured by the esterification of glycerin and fatty acids (mainly caprylic and capric) from Abitec Corp., Columbus, Ohio) was added and the temperature increased to 53° C. and milling begun. Separately, a melamine-containing polymer precursor was prepared by combining 4 g Colloid 121, 120 g RO water, and 0.3 g 21.5% sodium hydroxide, the latter to adjust the pH to 5.0 in a glass beaker. 12 g Cymel 385 was then added to the mixture while stirring. This mixture was then added to the reactor over a period of two minutes after which sodium sulfate (4.8 g) was added and the temperature increased to 85° C. and the mixture stirred for 8 hours. The mixture was allowed to cool and samples removed for testing. The results are shown in Table 2.

Example 2—MF/AC Dual Wall

An aqueous solution of 0.6 g Vazo 501 (4,4'-azobis(4-cyanovaleric acid available from Dupont Co., Wilmington, Del.), 140 g water and 0.66 g 21.5% sodium hydroxide solution (to adjust the pH to 4.6) was added to a microcapsule slurry formed in accordance with the process of Comparative Example 1 and heated to 60° C. for thirty minutes. The mixture was then cooled to 50° C. and a mixture of 1.2 g t-butylaminoethyl methacrylate (TBAEMA), 0.7 g concentrated hydrochloric acid (to adjust pH to 2.8), 10 g SR 9035 (15 mole ethoxylated trimethylolpropane triacrylate from Sartomer Co.) and 50 g water was added and the temperature was gradually increased to 75° C. and the slurry stirred for three hours. The mixture was allowed to cool and samples removed for testing. The results are shown in Table 2.

TABLE 2

| | Leakage | | | | % | | Fracture | |
| | 24 hours | 1 week | 2 weeks | 4 weeks | Free Oil | % Static Smudge | Strength (Mpa) | % Deformation |
| Example | | | | | | | | |
| --- | --- | --- | --- | --- | --- | --- | --- | --- |
| CE1 | 0.14 | 0.79 | 1.19 | 1.91 | 0.03 | 56.90 | 4.40 | 55.44 |
| 2 | 0.26 | 0.88 | 1.24 | 1.83 | 0.08 | 58.1 | 6.40 | 61.07 |

Comparative Example 3—MF Single Wall

A first water phase was prepared by combining 17.5 g Colloid 351 (copolymer of 92% acrylic acid and 8% butyl acrylate available from Rhone-Poulenc, Cedex, France), 17.5 g Colloid 121 (polyacrylic acid available from Rhone-Poulenc, Cedex, France), and 200 g DI water in a reactor. The pH was adjusted to 5.9 with 8.26 g of 21.5% aqueous sodium hydroxide. The mixture was stirred and 7.5 g Cymel 385 (a methylated high imino melamine resin with a low degree of alkylation available from Allnex Co., Brussels, Belgium) was added dropwise over one minute. 200 g of a core material, a perfume oil composition, was added to the reactor and the mixture milled at 1200 rpm at 53° C. for 22 minutes.

Separately, a melamine-containing polymer precursor was prepared by combining 4 g Colloid 121, 120 g RO water, and 0.51 g 21.5% sodium hydroxide, the latter to adjust the pH to 5.0 in a class beaker. 12 g Cymel 385 was then added to the mixture while stirring. This mixture was then added to the reactor over a period of two minutes after which sodium sulfate (4.8 g) was added and the temperature increased to 85° C. and the mixture stirred for 8 hours. The mixture was allowed to cool and samples removed for testing. The results are shown in Table 3.

Example 4—MF/AC Dual Wall

An aqueous solution of 0.6 g Vazo 501 (4,4'-azobis(4-cyanovaleric acid available from Dupont Co., Wilmington, Del.), 140 g water and 0.62 g 21.5% sodium hydroxide solution (to adjust the pH to 4.8) was heated to 60° C. for thirty minutes after which and a mixture of 1.2 g t-butylaminoethyl methacrylate (TBAEMA), 0.7 g concentrated hydrochloric acid (to adjust pH to 2.8) was added and then 10 g SR 9035 (15 mole ethoxylated trimethylolpropane triacrylate from Sartomer Co.) in 50 g water was added and mixed for thirty minutes at 60° C. This composition was then added to a microcapsule slurry formed in accordance with the process of Comparative Example 3 and the slurry cooked at 50° C. for 3 hours. The mixture was allowed to cool and samples removed for testing. The results are shown in Table 3.

TABLE 3

| Example | % Free Oil | % Static Smudge | Fracture Strength (Mpa) | % Deformation |
|---|---|---|---|---|
| CE3 | 0.03 | 47.7 | 9.62 | 64.18 |
| 4 | 0.14 | 39.2 | 12.21 | 65.10 |

TABLE 4

| Ingredient | Comparative Example 5 | Example 6 | Example 7 | Example 8 | Example 9 |
|---|---|---|---|---|---|
| Internal Phase ||||||
| EH | 19.66 | 19.63 | 17.31 | 16.40 | 16.40 |
| Captex 355 | 13.10 | 13.09 | 11.54 | 10.94 | 10.94 |
| Water Phase I ||||||
| C-351 | 2.87 | 2.86 | 2.52 | 2.39 | 2.39 |
| C-121 | 2.87 | 2.86 | 2.52 | 2.39 | 2.39 |
| NaOH | 0.98 | 0.98 | 0.87 | 0.94 | 0.94 |
| DI H$_2$O | 32.76 | 32.72 | 36.07 | 27.34 | 27.34 |
| V-50 | | 0.16 | 0.14 | | |
| V-501 | | | | 0.14 | 0.14 |
| Cymel 385 | 1.23 | 1.23 | 2.81 | 1.03 | 1.03 |
| Water Phase II ||||||
| C-121 | 0.66 | 0.65 | | 0.55 | 0.55 |
| DI | 19.66 | 19.63 | | 16.4 | 16.4 |
| Cymel 385 | 1.97 | 1.96 | | 1.64 | 1.64 |
| 21.5% NaOH | 0.05 | 0.05 | | 0.04 | 0.04 |
| Na$_2$SO$_4$ | 0.79 | | | | |
| BKB | 3.42 | | | | |
| Water Phase III ||||||
| C-351 | | 0.65 | 5.91 | 1.09 | 1.09 |
| DI H$_2$O | | 19.63 | 17.31 | 16.4 | 16.4 |
| NaOH | | | | 0.22 | 0.22 |
| TBAEMA | | 0.33 | 0.29 | | |
| HEMA | | 0.33 | 0.29 | 0.27 | 0.27 |
| SR444 | | 0.98 | 0.87 | 0.82 | |
| SR601 | | | | | 0.82 |
| CD9055 | | | | 0.27 | 0.27 |
| 5% NaHSO$_4$ | | 0.33 | 0.29 | 0.27 | 0.27 |
| Na$_2$SO$_4$ | | 0.79 | 0.69 | 0.66 | 0.66 |
| Milling Time | 30 min | 25 min | 60 min | 60 min | 60 min |
| Particle Size (µ) | 17.43 | 16.06 | 14.8 | 18.27 | 18.7 |
| Free Oil | 0 | 0 | 0.01 | 0 | 0.02 |
| Static Smudge | 28.6 | 45.8 | 42.5 | 47.4 | 66.0 |
| 24 hour hexane leakage | 0.14 | 0.14 | 0.30 | 0.17 | 0.38 |
| 1 week hexane leakage | 0.85 | 0.82 | 1.62 | 0.97 | 1.53 |
| 2 weeks hexane leakage | 1.61 | 1.64 | 3.08 | 1.95 | 2.72 |
| 4 weeks hexane leakage | 2.17 | 2.98 | 5.63 | 3.72 | 4.85 |

Comparative Example 5, Examples 6-9

A series of dual water phase examples were prepared according to the following general procedure. Water Phase I (WPI) is prepared and held at 50° C. for 30 minutes. The Internal Phase (IP) core material was prepared and heated to 35° C. under nitrogen blanket and subsequently added to Water Phase I. This mixture was milled for various time periods to attain the targeted emulsion size and then the milling blade replaced with a mixer blade. A second water phase compositions was then added (WPII) with continuous mixing followed by the addition of a third water phase (WPIII). The mixture was heated to 75° C. over a period 180 minutes and then held at that temperature for a period of 4 hours. Thereafter the temperature of the mixture was elevated to 95° C. over a period of 60 minutes and held for 6 hours after which the mixture was allowed to cool to room temperature naturally. The specific compositions and make-up of these examples (presented as weight percent of the listed components) as well as the milling times and particle sizes are presented in Table 4. As noted in Table 4, not all examples employed all phase compositions. In those instances, the process was followed with the exception of the omission of the preparation and addition of those compositions.

About 45 minutes before combining the oil and water phases to begin milling, the first and second oil phase materials were combined and mixed for 10 minutes. Subsequently, the first water phase was added to the reactor containing the combined oil phases and the mixture milled at 50° C. with samples taken every 15 minutes until a targeted ~18 micron droplet emulsion of the water phase in the oil phase was obtained. The emulsion was then heated to 75° C. and cooked for 60 minutes after which the second water phase was added while maintaining temperature and mixing and the mixture allowed to continue cooking for an additional 160 minutes after which time the temperature was raised to 95° C. and the mix cooked for an additional 7 hours. Microcapsules prepared by this method were then sampled and tested and the results shown in Table 5.

TABLE 5

| Example | Leakage | | | | % Free Oil | % Static Smudge | Fracture Strength (Mpa) | % Deformation |
| --- | --- | --- | --- | --- | --- | --- | --- | --- |
| | 24 hours | 1 week | 2 weeks | 4 weeks | | | | |
| E10 | 2.16 | 6.66 | 9.76 | 16.31 | 0.13 | 69.5 | 2.27 | 38.52 |

Comparative Example 11—AC Single Wall

A first oil phase composition was prepared by combining 84.38 g of a perfume oil 75 g IPM, 1 g Vazo 67 and 0.8 g V-501 in a reactor vessel at 35° C. under nitrogen blanket with low speed mixing (120 rpm) after which it has heated to 70° C. and held for 45 minutes and then cooled and held at 50° C. A second oil phase composition was separately prepared by combining 28.13 g of a perfume, 0.22 g TBAEMA, and 0.22 g CD9055 in a second vessel. To this second oil phase composition was added 18 g of CN975 (about 45 minutes prior to forming the emulsion) and the mixture added to the reactor vessel containing the first oil phase composition and mixed for 10 minutes. Thereafter a water phase composition prepared by combining 22.5 g C351, 1.2 g V-501, 325 g RO/DI water and 1.1 g NaOH (21.5%)(added to bring the pH to 4.6) was added to the combined oil phase composition in the reactor vessel and the mixture milled, taking samples every 15 minutes until the targeted droplet size was attained (16.8 microns). The composition was then heated to 75° C. and held for 5 hours after which the temperature was raised again to 95° C. and held for an additional 7 hours. The mixture was allowed to cool and samples removed for testing. The results are shown in Table 6.

Example 12—AC/MF Dual Wall

A water phase composition was prepared by combining 17.45 g C351, 36 g Cymel 385 and 51.42 g RO/DI water and then 4.71 g NaOH (21.5%) to adjust the pH to 5. This water phase composition was then added to a microcapsule slurry formed in accordance with the process of Comparative Example 11 and the slurry cooked at 60° C. for 1 hour. The mixture was allowed to cool and samples removed for testing. The results are shown in Table 6.

TABLE 6

| Example | % Free Oil | % Static Smudge | Fracture Strength (Mpa) | % Deformation |
| --- | --- | --- | --- | --- |
| CE11 | 0.05 | 79.3 | 2.92 | 36.34 |
| 12 | 0.01 | 67.3 | 4.29 | 45.03 |

Comparative Example 13, Examples 14-17

A series of dual oil/water phase examples were prepared according to the following general procedure. The components of Oil Phase II (OP II) are added to a reactor vessel and mixed at low speed (~120 rpm) at 35° C. under a nitrogen blanket. Oil Phase Ii is then heated to 75° C. over a period of 45 minutes and held at that temperature for an additional 45 minutes. The components of Oil Phase I, less the multifunctional (meth)acrylate (CN975), is mixed at room temperature and set aside. About 45 minutes prior to milling, the multifunctional (meth)acrylate (CN975) is added and mixed and this mixture then added to the reactor containing Oil Phase II and mixed for 10 minutes. Concurrently, the Water Phase I and Water Phase II compositions are individually prepared and heated to 50° C. and held. Water Phase I is added to the oil phase mixture and the contents of the reactor milled for about one hour. After milling, the milling blade is replaced with a mixer blade and Water Phase II is added. With mixing, the contents of the reactor vessel is then heated to 75° C. over a period of 180 minutes and then held at that temperature for a period of 4 hours. Thereafter the temperature of the mixture was elevated to 95° C. over a period of 60 minutes and held for 6 hours after which the mixture was allowed to cool to room temperature naturally. The specific compositions and make-up (presented as weight percent of the listed components) of these examples are presented in Table 7. As noted in Table 7, not all examples employed all phase compositions. In those instances, the process was followed with the exception of the omission of the preparation and addition of those compositions.

TABLE 7

| Ingredient | Comparative Example 13 | Example 14 | Example 15 | Example 16 | Example 17 |
| --- | --- | --- | --- | --- | --- |
| Water Phase I | | | | | |
| C-351 | 4.01 | 3.52 | 3.52 | 3.52 | 3.52 |
| 21.5% NaOH | 0.86 | 0.75 | 0.75 | 0.75 | 0.75 |
| DI H$_2$O | 57.91 | 50.88 | 50.86 | 50.86 | 50.88 |
| V-501 | 0.21 | 0.19 | 0.19 | 0.19 | 0.19 |
| Cymel 385 | | | | | 0.63 |
| Water Phase II | | | | | |
| C-351 | | 1.25 | 1.25 | 1.25 | 1.25 |
| DI H$_2$O | | 8.05 | 8.05 | 8.05 | 8.05 |
| Cymel 385 | | 1.88 | 1.88 | 1.88 | 1.25 |
| 21.5% NaOH | | 0.21 | 0.21 | 0.21 | 0.21 |
| Na$_2$SO$_4$ | | 0.75 | 0.75 | 0.75 | 0.75 |

TABLE 7-continued

| Ingredient | Comparative Example 13 | Example 14 | Example 15 | Example 16 | Example 17 |
|---|---|---|---|---|---|
| Oil Phase I | | | | | |
| PO | 6.68 | 5.87 | 5.87 | 5.87 | 5.87 |
| TBAEMA | 0.04 | 0.03 | 0.03 | 0.07 | 0.03 |
| CD9055 | 0.04 | 0.03 | 0.07 | 0.03 | 0.03 |
| CN975 | 3.21 | 2.82 | 2.82 | 2.82 | 2.82 |
| Oil Phase II | | | | | |
| PO | 13.36 | 11.74 | 11.74 | 11.74 | 11.74 |
| Captex 355 | 13.36 | 11.74 | 11.74 | 11.74 | 11.74 |
| Vazo 67 | 0.18 | 0.16 | 0.16 | 0.16 | 0.16 |
| V-501 | 0.14 | 0.13 | 0.13 | 0.13 | 0.13 |
| Particle Size (μ) | 20.3 | 20.06 | 20.06 | 20.06 | 25.65 |
| Free Oil | 0.36 | 0.04 | 0.05 | 0.05 | 0.04 |
| Static Smudge | 63.8 | 60.0 | 59.3 | 60.8 | 87.1 |
| 24 hour Hexane Leakage | 6.62 | 1.34 | 2.41 | 2.14 | 0.99 |
| 1 week Hexane Leakage | 27.02 | 13.65 | 21.28 | 17.09 | 3.11 |
| 2 weeks Hexane Leakage | 32.70 | 18.64 | 26.15 | 22.84 | 4.48 |
| 4 weeks Hexane Leakage | 48.52 | 31.93 | 41.00 | 38.27 | 5.76 |

Of particular note, in the case of Example 17 a portion of the Cymel 385 melamine resin was added to both water phase compositions. It was found that the addition of the melamine resin to Water Phase I resulted in a significant reduction in the formation of extraneous particles of the melamine resin. In contrast, those compositions in which the melamine resin was only present in Water Phase II were found to have a significant amount of small particles (<1μ) of polymerized wall material. Though not intending to be bound by theory, it is also believed that the small amount of Cymel 385 melamine resin in Water Phase I initiates wall formation at the interface of the oil and water phases, thereby physically stabilizing the droplets of the oil phase in the water phase.

Commercial Applications

The microcapsules formed according to the present teachings have a number of commercial applications. For convenience, before addressing specific application, the following definitions are presented as they pertain to the discussion on commercial applications.

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrances (e.g. perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein "cleaning and/or treatment compositions" means products comprising fluid laundry detergents, fabric enhancers, laundry and/or rinse additives, fluid dishwashing detergents, fluid hard surface cleaning and/or treatment compositions, fluid toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the present invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "Sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks: in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to about 2% or less, about 1% or less, or about 0.1% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless specifically stated otherwise, the test methods disclosed in the Test Methods Section of the present application should be used to determine the respective values of the parameters of Applicants' inventions.

Unless otherwise noted, in discussing the commercial applications below, all component or composition levels are in reference to the active portion of that component or composition, and are exclusive of impurities, for example, residual solvents or by-products, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Consumer Products

A consumer product comprising a consumer product ingredient and an improved dual melamine resin/(meth) acrylate polymer walled microcapsules wherein the improvement comprises the use of a combination of (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer in forming the (meth) acrylate ester-based portion of the microcapsule wall, is disclosed. Preferably said consumer product comprises, based on total consumer product weight from 0.001% about to about 25%, more preferably from about 0.01% to about 10%, more preferably from about 0.05% to about 5%, most preferably from about 0.1% to about 0.5% of said microcapsules.

A method of making a consumer product comprising combining a consumer product ingredient and a microcapsule made by an improved method of making dual melamine resin/(meth)acrylate polymer walled microcapsules wherein the improvement comprises the use of a combination of (a) at least one oil soluble or dispersible acidic (meth)acrylate, (b) at least one oil soluble or dispersible simple base, and (c) at least one oil soluble or dispersible multifunctional (meth) acrylate monomer or oligomer in forming the (meth)acrylate ester-based portion of the microcapsule wall is disclosed.

A method of making a consumer product comprising combining a consumer product ingredient and a microcapsule made by an improved method of making dual melamine resin/(meth)acrylate polymer walled microcapsules wherein the improvement comprises (i) the use of either (A) (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer or (B) a combination of (a) at least one oil soluble or dispersible acidic (meth)

acrylate, (b) at least one oil soluble or dispersible simple base, and (c) at least one oil soluble or dispersible multi-functional (meth)acrylate monomer or oligomer in forming the (meth)acrylate ester-based portion of the microcapsule wall and (ii) the concurrent or near concurrent deposition and polymerization of the (meth)acrylate polymer and melamine resin at the oil/water phase interface, is disclosed.

A method of making a consumer product comprising combining a consumer product ingredient and a microcapsule made by an improved method of making dual melamine resin/(meth)acrylate polymer walled microcapsules wherein the improvement comprises the use of (a) at least one water soluble or dispersible multifunctional (meth)acrylate monomer or oligomer alone or in combination with (b) at least one water soluble or dispersible mono- and/or di-functional (meth)acrylate and/or (c) at least one water soluble or dispersible simple base in the production of the (meth) acrylate ester-based portion of the microcapsule wall, is disclosed.

A method of making a consumer product comprising combining a consumer product ingredient and a microcapsule made by an improved method of making dual melamine resin/(meth)acrylate polymer walled microcapsules wherein the improvement comprises the selected use of water soluble or dispersible melamine resin pre-polymers and/or polymers and/or the precursors therefore which are able to polymerize/copolymerize through self-condensation, is disclosed.

Benefit Agents that can Serve as Core Material for Microcapsules

Useful core materials include perfume raw materials, sensates, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers and anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, and natural actives such as aloe vera, vitamin E, shea butter, cocoa butter, and the like, brighteners, antibacterial actives, antiperspirant actives, cationic polymers, dyes and mixtures thereof. In one aspect, said perfume raw material is selected from the group consisting of alcohols, ketones, aldehydes, esters, ethers, nitriles alkenes. In one aspect the core material comprises a perfume. In one aspect, said perfume comprises perfume raw materials selected from the group consisting of alcohols, ketones, aldehydes, esters, ethers, nitriles alkenes and mixtures thereof. In one aspect, said perfume may comprise a perfume raw material selected from the group consisting of perfume raw materials having a boiling point (B.P.) lower than about 250° C. and a Clog P lower than about 3, perfume raw materials having a B.P. of greater than about 250° C. and a Clog P of greater than about 3, perfume raw materials having a B.P. of greater than about 250° C. and a Clog P lower than about 3, perfume raw materials having a B.P. lower than about 250° C. and a Clog P greater than about 3 and mixtures thereof. Perfume raw materials having a boiling point B.P. lower than about 250° C. and a Clog P lower than about 3 are known as Quadrant I perfume raw materials, perfume raw materials having a B.P. of greater than about 250° C. and a Clog P of greater than about 3 are known as Quadrant IV perfume raw materials, perfume raw materials having a B.P. of greater than about 250° C. and a Clog P lower than about 3 are known as Quadrant II perfume raw materials, perfume raw materials having a B.P. lower than about 250° C. and a Clog P greater than about 3 are known as a Quadrant III perfume raw materials. In one aspect, said perfume comprises a perfume raw material having B.P. of lower than about 250° C. In one aspect, said perfume comprises a perfume raw material selected from the group consisting of Quadrant I, II, III perfume raw materials and mixtures thereof. In one aspect, said perfume comprises a Quadrant III perfume raw material. Suitable Quadrant I, II, III and IV perfume raw materials are disclosed in U.S. Pat. No. 6,869,923 B1.

In one aspect, said perfume comprises a Quadrant IV perfume raw material. While not being bound by theory, it is believed that such Quadrant IV perfume raw materials can improve perfume odor "balance". Said perfume may comprise, based on total perfume weight, less than about 30%, less than about 20%, or even less than about 15% of said Quadrant IV perfume raw material.

Additional Consumer Product Specifics

Additional consumer product specifics are found below. Such disclosure is also intended to cover the process of making the disclosed consumer products wherein said process comprises combing the materials as disclosed to form the described consumer product.

Cleaning and/or Treatment Compositions and Methods of Use

Preferably, said consumer product is a cleaning and/or treatment composition having a viscosity of from about 10 mPa·s to about 50,000 mPa·s, preferably from about 50 mPa·s to about 2000 mPa·s, most preferably from about 75 mPa·s to about 400 mPa·s, a pH from about 3 to about 10, preferably from about 4 to about 8, most preferably from about 5 to about 8, said composition comprising, based on total cleaning and/or treatment composition weight with from 0.001% about to about 25%, preferably from about 0.01% to about 10%, more preferably from about 0.05% to about 5%, most preferably from about 0.1% to about 0.5% of the microcapsules disclosed here in.

As the viscosity range of the cleaning and/or treatment composition is tightened, it is easier to suspend certain materials such as polymers and waxes.

Preferably said cleaning and/or treatment composition comprises:
  (a) a surfactant selected from the group consisting of nonionic surfactants, anionic surfactants, cationic surfactants, ampholytic surfactants, zwitterionic surfactants, semi-polar nonionic surfactants and mixtures thereof;
  (b) a solvent wherein the solvent is preferably selected from the group consisting of hydrogenated castor oil, glycols, alcohols, and mixtures thereof;
  (c) a fabric softener active wherein the fabric softener active is preferably selected from the group consisting of a quaternary ammonium compound, an amine and mixtures thereof, preferably said quaternary ammonium compound is selected from the group consisting of bis-(2-hydroxypropyl)-dimethylammonium methylsulphate fatty acid ester, 1,2-di(acyloxy)-3-trimethylammoniopropane chloride, N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate, 1, 2 di-(stearoyl-oxy) 3 trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmethyl hydroxyethylammoinum methosulfate and mixtures thereof, and (d) mixtures of (a) through (c).

Preferably said cleaning and/or treatment composition, comprises an adjunct ingredient selected from the group consisting of builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents in addition to said solubilizing agent, a fabric softener active selected from the group consisting of a silicone polymer, a polysaccharide, a clay, a fatty ester, a dispersible polyolefin, a polymer latex and mixtures thereof, pigments, and mixtures thereof, preferably said composition comprises an organic acid, preferably citric acid and/or lactic acid, hydrogenated castor oil, ethoxylated polyethleneimines, preferably PEI 600 EO 20 and/or PEI 600, an enzyme, preferably a cold water amylase, cold water protease and/or xylogluconase.

In one aspect of Applicants' cleaning and/or treatment composition, said cleaning and/or treatment composition comprises a fabric softener active selected from the group consisting of a quaternary ammonium compound, a silicone polymer, a polysaccharide, a clay, an amine, a fatty ester, a dispersible polyolefin, a polymer latex and mixtures thereof, preferably (a) said quaternary ammonium compound comprises an alkyl quaternary ammonium compound, preferably said alkyl quaternary ammonium compound is selected from the group consisting of a monoalkyl quaternary ammonium compound, a dialkyl quaternary ammonium compound, a trialkyl quaternary ammonium compound and mixtures thereof;

(b) said silicone polymer is selected from the group consisting of cyclic silicones, polydimethylsiloxanes, aminosilicones, cationic silicones, silicone polyethers, silicone resins, silicone urethanes, and mixtures thereof;

(c) said polysaccharide comprises a cationic starch;

(d) said clay comprises a smectite clay;

(e) said dispersible polyolefin is selected from the group consisting of polyethylene, polypropylene and mixtures thereof; and (f) said fatty ester is selected from the group consisting of a polyglycerol ester, a sucrose ester, a glycerol ester and mixtures thereof.

In one aspect of Applicants' cleaning and/or treatment composition, said cleaning and/or treatment composition comprises a fabric softener active comprising a material selected from the group consisting of monoesterquats, diesterquats, triesterquats, and mixtures thereof, preferably, said monoesterquats and diesterquats are selected from the group consisting of bis-(2-hydroxypropyl)-dimethylammonium methylsulfate fatty acid ester and isomers of bis-(2-hydroxypropyl)-dimethylammonium methylsulfate fatty acid ester and/or mixtures thereof, 1,2-di(acyloxy)-3-trimethylammoniopropane chloride, N,N-bis(stearoyl-oxy-ethyl)-N,N-dimethyl ammonium chloride, N,N-bis(tallowoyl-oxy-ethyl)-N,N-dimethyl ammonium chloride, N,N-bis(stearoyl-oxy-ethyl)-N-(2-hydroxyethyl)-N-methyl ammonium methylsulfate, N,N-bis-(stearoyl-2-hydroxypropyl)-N,N-dimethylammonium methylsulfate, N,N-bis-(tallowoyl-2-hydroxypropyl)-N,N-dimethylammonium methylsulfate, N,N-bis-(palmitoyl-2-hydroxypropyl)-N,N-dimethylammonium methylsulfate, N,N-bis-(stearoyl-2-hydroxypropyl)-N,N-dimethylammonium chloride, 1,2-di-(stearoyl-oxy)-3-trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmylmethyl hydroxyethylammoinum methylsulfate and mixtures thereof.

In one aspect of Applicants' cleaning and/or treatment composition, said composition comprises a quaternary ammonium compound and a silicone polymer, preferably said composition comprises from 0.001% to 10%, from 0.1% to 8%, more preferably from 0.5% to 5%, of said silicone polymer.

In one aspect of Applicants' cleaning and/or treatment composition, said fabric softening active has an Iodine Value of between 0-140, preferably 5-100, more preferably 10-80, even more preferably, 15-70, most preferably 18-25 or when said fabric softening active comprises a partially hydrogenated fatty acid quaternary ammonium compound said fabric softening active most preferably has a Iodine Value of 25-60.

In one aspect of Applicants' cleaning and/or treatment composition, said cleaning and/or treatment composition is a soluble unit-dose product said soluble unit dose product comprising one or more cleaning and/or treatment compositions contained within one or more chambers said chambers being formed from one or more films, preferably said one or more films comprise PVA film.

The compositions of the present invention may be used in any conventional manner. In short, they may be used in the same manner as products that are designed and produced by conventional methods and processes. For example, compositions of the present invention can be used to treat a situs inter alia a surface or fabric. Typically at least a portion of the situs is contacted with an aspect of Applicants' composition, in neat form or diluted in a wash liquor, and then the situs is optionally washed and/or rinsed. For purposes of the present invention, washing includes but is not limited to, scrubbing, and mechanical agitation. The fabric may comprise any fabric capable of being laundered in normal consumer use conditions. When the wash solvent is water, the water temperature typically ranges from about 5° C. to about 90° C. and, when the situs comprises a fabric, the water to fabric mass ratio is typically from about 1:1 to about 100:1.

The cleaning and/or treatment compositions of the present invention may be used as liquid fabric enhancers wherein they are applied to a fabric and the fabric is then dried via line drying and/or drying the an automatic dryer.

In one aspect, a method of controlling malodors comprising: contacting a situs comprising a malodor and/or a situs that will become malodorous with a cleaning and/or treatment composition selected from the group consisting of Applicants' cleaning and/or treatment compositions and mixtures thereof, is disclosed.

In one aspect of Applicants' method, said situs comprises a fabric and said contacting step comprises contacting said fabric with a sufficient amount of Applicants' cleaning and/or treatment compositions to provide said fabric with at least 0.0025 mg of benefit agent, such as perfume, per kg of fabric, preferably from about 0.0025 mg of benefit agent/kg of fabric to about 50 mg of malodor reduction material/kg of fabric, more preferably from about 0.25 mg of benefit agent/kg of fabric to about 25 mg of benefit agent/kg of fabric, most preferably from about 0.5 of benefit agent/kg of fabric to about 10 mg of benefit agent/kg of fabric of said sum of malodor reduction materials.

Solid Consumer Products and Methods of Use

Preferably said consumer product is a powder, granule, flake, bar or bead, said consumer product comprising, based on total product weight:
 (a) with from 0.001% about to about 25%, preferably from about 0.01% to about 10%, more preferably from about 0.05% to about 5%, most preferably from about 0.1% to about 0.5% of the microcapsules disclosed here in;
 (b) a carrier that is a solid at 25° C., preferably said solid carrier is selected from the group consisting of clays, sugars, salts, silicates, zeolites, citric acid, maleic acid, succinic acid, benzoic acid, urea and polyethylene oxide and mixtures thereof; preferably said carriers is present at a level of:
   (i) from about 20% to about 95%, more preferably about 30% to about 90%, even more preferably about 45% to about 90%, and most preferably about 60% to about 88%; or
   (ii) from about 1% to about 60%, more preferably about 2% to about 50%, even more preferably about 3% to about 45% and most preferably, about 4% to about 40%; and
 (c) optionally, 0.5% to about 50% of an enzyme stable polymer, preferably said enzyme stable polymer is selected from the group consisting of polyacrylate polymers, polyamine polymer, acrylate/maleate copolymer, a polysaccharide, and mixtures thereof, preferably said polysaccharide is selected from the group consisting of carboxy methyl cellulose, cationic hydroxy ethyl cellulose and mixtures thereof.

In one aspect of said product, said product comprises a perfume.

In one aspect of said product, said product comprising an additional material that is an adjunct ingredient selected from the group consisting of surfactants, builders, chelating agents, dye transfer inhibiting agents, dispersants, enzymes, and enzyme stabilizers, catalytic materials, bleach activators, a fabric softener active, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents, pigments and mixtures thereof.

The compositions of the present invention may be used in any conventional manner. In short, they may be used in the same manner as products that are designed and produced by conventional methods and processes. For example, compositions of the present invention can be used to treat a situs inter alia a surface or fabric. Typically at least a portion of the situs is contacted with an aspect of Applicants' composition, in neat form or diluted in a wash liquor, and then the situs is optionally washed and/or rinsed. For purposes of the present invention, washing includes but is not limited to, scrubbing, and mechanical agitation. The fabric may comprise any fabric capable of being laundered in normal consumer use conditions. When the wash solvent is water, the water temperature typically ranges from about 5° C. to about 90° C. and, when the situs comprises a fabric, the water to fabric mass ratio is typically from about 1:1 to about 100:1.

The compositions of the present invention may be used as fabric enhancers wherein they are applied to a fabric and the fabric is then dried via line drying and/or drying the an automatic dryer.

A method of freshening comprising: contacting a situs comprising with a product selected from the group consisting of the products described herein and mixtures thereof, is disclosed.

Freshening Compositions, Methods of Use and Delivery Systems

Preferably, said consumer product is a freshening composition having a viscosity of from about 1 mPa·s to about 50,000 mPa·s, preferably from about 1 mPa·s to about 2000 mPa·s, most preferably from about 1 mPa·s to about 400 mPa·s, a pH from about 3 to about 10, preferably from about 4 to about 8, most preferably from about 5 to about 8, said freshening composition comprising, based on total freshening composition weight:
 (a) with from 0.001% about to about 25%, preferably from about 0.01% to about 10%, more preferably from about 0.05% to about 5%, most preferably from about 0.1% to about 0.5% of the microcapsules disclosed here in; and
 (b) from about 0.01% to about 3%, preferably from about 0.4% to about 1%, more preferably from about 0.1% to about 0.5%, most preferably from about 0.1% to about 0.3% of solublizing agent, preferably said solublizing agent is selected from the group consisting of a surfactant, a solvent and mixtures thereof,
   (i) preferably said surfactant comprises a non-ionic surfactant;
   (ii) preferably said solvent comprises an alcohol, a polyol and mixtures thereof;
 (c) optionally, an adjunct ingredient.

As the viscosity is lowered you obtain improved sprayability and improved penetration into fabric.

In one aspect of said freshening composition, said composition comprises an adjunct ingredient selected from the group consisting of isoalkanes comprising at least 12 carbon atoms, a compound comprising a quaternary amine moiety, lubricants, additional solvents, glycols, alcohols, silicones, preservatives, anti-microbial agents, pH modifiers, a carrier, insect repellants, metallic salts, cyclodextrins, functional polymers, anti-foaming agents, antioxidants, oxidizing agents, chelants and mixtures thereof; preferably lubricants wherein the lubricants preferably comprise hydrocarbons, more preferably hydrocarbons that comprise two or more branches or compounds comprising a quaternary amine moiety comprising at least 10 carbon atoms.

A device comprising Applicants' freshening compositions, said device being preferably selected from the group consisting of trigger sprayers, manual aerosol sprayers, automatic aerosol sprayers, wick containing devices, fan devices, and thermal drop-on-demand devices, is disclosed.

A method of freshening comprising: contacting a situs with a composition selected from the group consisting of the freshening compositions disclosed herein and mixtures thereof is disclosed.

In one aspect of said method, said contacting step comprises contacting said situs with a sufficient amount of the compositions disclosed herein to provide said situs with, from about 0.1 milligrams (mg) to about 10,000 mg, preferably from about 1 mg to about 5,000 mg most preferably from about 5 mg to about 1000 mg of a benefit agent, preferably a perfume, per square meter of projected surface area of said situs.

The composition of the present invention may be used with a hard surface cleaner, as is commonly used to clean countertops, tables and floors. A suitable floor cleaning liquid is sold by the instant assignee in a replaceable reservoir under the name WetJet. The cleaning solution may particularly be made according to the teachings of commonly assigned U.S. Pat. No. 6,814,088. The reservoir may be used with and dispensed from a floor cleaning implement, in conjunction with a disposable floor sheet. A suitable spray implement is also sold under the name WetJet. A suitable reservoir and fitment therefore may be made according to the teachings of commonly assigned U.S. Pat. No. 6,386,392 and/or 7,172,099. If desired the floor cleaning implement may dispense steam, according to the teachings of jointly assigned US 2013/0319463. Alternatively a refillable reservoir may be utilized.

If desired the composition of the present invention may be used with a pre-moistened sheet. If the cleaning sheet is pre-moistened, it is preferably pre-moistened with a liquid which provides for cleaning of the target surface, such as a floor, but yet does not require a post-cleaning rinsing operation. The cleaning sheet may be loaded with at least 1, 1.5 or 2 grams of cleaning solution per gram of dry substrate, but typically not more than 5 grams per gram. The cleaning solution may comprise a surfactant, such as APG surfactant which minimizes streaking since there is typically not a rinsing operation, according to the teachings of U.S. Pat. No. 6,716,805.

The composition of the present invention may be used for raised hard surfaces, as is sold under the names Mr. Clean and Mr. Proper. The composition may be dispensed from a trigger sprayer or aerosol sprayer, as are well known in the art. An aerosol sprayer dispenses the composition using propellant pressure, while a trigger sprayer dispenses the composition by pumping the composition under manual actuation. A suitable aerosol dispenser may have a dip tube or bag on valve, according to US 2015/0108163 and/or US 2011/0303766. A suitable trigger sprayer is found in U.S. Pat. No. 8,322,631.

The present freshening composition may be used in a device for the delivery of a volatile material to the atmosphere or on inanimate surfaces (e.g. fabric surfaces as a fabric refresher). Such device may be configured in a variety of ways. For example, the device may be configured for use as an energized air freshener (i.e. powered by electricity; or chemical reactions, such as catalyst fuel systems; or solar powered; or the like). Exemplary energized air freshening devices include a powered delivery assistance means which may include a heating element, fan assembly, or the like. More particularly, the device may be an electrical wall-plug air freshener as described in U.S. Pat. No. 7,223,361; a battery (including rechargeable battery) powered air freshener having a heating and/or fan element. In energized devices, the volatile material delivery engine may be placed next to the powered delivery assistance means to diffuse the volatile perfume material. The volatile perfume material may be formulated to optimally diffuse with the delivery assistance means.

Alternatively, the device may be configured for use as a non-energized air freshener. An exemplary non-energized air freshener includes a reservoir and, optionally, capillary or wicking means or an emanating surface, to help volatile materials passively diffuse into the air (i.e. without an energized means). A more specific example includes a delivery engine having a liquid reservoir for containing a volatile material and a microporous membrane enclosing the liquid reservoir as disclosed in U.S. Pat. Nos. 8,709,337 and 8,931,711.

The device may also be configured for use as an aerosol sprayer or a non-aerosol air sprayer including traditional trigger sprayers as well as trigger sprayer having a pre-compression and/or buffer system for fluid therein. In this embodiment, the delivery engine can deliver volatile materials upon user demand or programmed to automatically deliver volatile materials to the atmosphere.

The apparatus may also be configured for use with an air purifying system to deliver both purified air and volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

Article and Method of Use

Preferably said consumer product is an article comprising (a) a substrate, preferably a flexible substrate, more preferably a flexible substrate that is a sheet; preferably said substrate comprises a fabric softening active, preferably said fabric softening active coats all or a portion of said substrate; and (b) based on total article weight with from 0.001% about to about 25%, preferably from about 0.01% to about 10%, more preferably from about 0.05% to about 5%, most preferably from about 0.1% to about 0.5% of the microcapsules disclosed here in.

Preferably said article has a weight ratio of fabric softener active to dry substrate ranging from about 10:1 to about 0.5:1, preferably from about 5:1 to about 1:1, preferably said fabric softener active is selected from the group consisting of a quaternary ammonium compound, a silicone polymer, a polysaccharide, a clay, an amine, a fatty ester, a dispersible polyolefin, a polymer latex and mixtures thereof.

In one aspect, said article has a weight ratio of fabric softener active to dry substrate ranging from about 10:1 to about 0.5:1, preferably from about 5:1 to about 1:1, preferably said fabric softener active is selected from the group consisting of (a) a cationic fabric softener active, preferably a quaternary-ammonium fabric softener active, more preferably a di(long alkyl chain)dimethylammonium ($C_1$-$C_4$ alkyl) sulfate or chloride, preferably the methyl sulfate; an ester quaternary ammonium compound, an ester amine precursor of an ester quaternary ammonium compound, and mixtures thereof, preferably a diester quaternary ammonium salt;

(b) a carboxylic acid salt of a tertiary amine and/or ester amine;

(c) a nonionic fabric softener material, preferably fatty acid partial esters of polyhydric alcohols, or anhydrides thereof, wherein the alcohol or anhydride contains from about 2 to about 18 and preferably from about 2 to about 8 carbon atoms, and each fatty acid moiety contains from about 8 to about 30 and preferably from about 12 to about 20 carbon atoms;
(d) alkanolamides;
(e) fatty acids; and
(f) mixtures of the foregoing.

Preferably, said article comprises, based on total article weight, from 1% to 99% by weight, preferably from about 1% to about 80%, more preferably from about 20% to about 70%, most preferably from about 25% to about 60% of a fabric softening active.

Preferably said article comprises a quaternary ammonium compound selected from the group consisting of bis-(2-hydroxypropyl)-dimethylammonium methylsulphate fatty acid ester, 1,2-di(acyloxy)-3-trimethylammoniopropane chloride, N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate, 1, 2 di (stearoyl-oxy) 3 trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmethyl hydroxyethylammoinum methosulfate and mixtures thereof.

In one aspect of said article, said article comprises a fabric softening active having an Iodine Value of between 0-140, preferably 5-100, more preferably 10-80, even more preferably, 15-70, most preferably 18-25.

In one aspect of said article, said article comprises an adjunct ingredient selected from the group consisting of surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents, pigments anti-oxidants, colorants, preservatives, optical brighteners, opacifiers, stabilizers such as guar gum and polyethylene glycol, anti-shrinkage agents, anti-wrinkle agents, soil release agents, fabric crisping agents, reductive agents, spotting agents, germicides, fungicides, anti-corrosion agents, antifoam agents, Color Care Agents including Chlorine Scavengers, Dye Transfer Inhibitors, Dye Fixatives Chelants and Anti-Abrasion Agents Perfume, PMC's, Cyclodextrin Perfume Complexes, Free Cyclodextrin, Pro-Perfumes; Antioxidants and mixtures thereof.

A method of controlling softening and/or freshening comprising: contacting a situs comprising one or more of the articles Applicants' disclose herein, is disclosed.

In one aspect of said method, said situs comprises a fabric and said contacting step comprises contacting said fabric with a sufficient amount of Applicants' article containing to provide said fabric with a level of perfume of at least 0.0025 mg of perfume/kg of fabric, preferably from about 0.00025 mg of perfume/kg of fabric to about 25 mg of perfume/kg of fabric, more preferably from about 0.025 mg of perfume/kg of fabric to about 20 mg of perfume/kg of fabric, most preferably from about 0.25 of perfume/kg of fabric to about 10 mg of malodor reduction material/kg of fabric of said sum of malodor reduction materials.

One aspect of the present invention relates to fabric conditioning compositions which are delivered to fabric via dryer-added substrate that effectively releases the composition in an automatic laundry (clothes) dryer. Such dispensing means can be designed for single usage or for multiple uses. The dispensing means can also be a "carrier material" that releases the fabric conditioning composition and then is dispersed and/or exhausted from the dryer. When the dispensing means is a flexible substrate, e.g., in sheet configuration, the fabric conditioning composition is releasably affixed on the substrate to provide a weight ratio of conditioning composition to dry substrate ranging from about 10:1 to about 0.5:1, preferably from about 5:1 to about 1:1. To insure release, preferred flexible sheets withstand the dryer environment without decomposing or changing shape, e.g. combusting, creating off odors, or shrinking with heat or moisture. Substrates especially useful herein are rayon and/or polyester non-woven fabrics.

Non-limiting examples of the substrates useful herein are cellulosic rayon and/or polyester non-woven fabrics having basis weights of from about 0.4 oz./yd$^2$ to about 1 oz./yd$^2$, preferably from about 0.5 oz./yd$^2$ to about 0.8 oz./yd$^2$, more preferably from about 0.5 oz./yd$^2$ to about 0.6 oz./yd$^2$. These substrates are typically prepared using, e.g., rayon and/or polyester fibers having deniers of from about 1 to about 8, preferably from about 3 to about 6, and more preferably about 4 to 6 or mixtures of different deniers. Typically, the fiber is a continuous filament or a 3/16 inch to 2 inch fiber segment that is laid down, in a pattern that results in a multiplicity of layers and intersections between overlayed portions of the filament or fiber, on a belt, preferably foraminous, and then the fiber intersections are glued and/or fused into fiber-to-fiber bonds by a combination of an adhesive binder, and/or heat and/or pressure. As non-limiting examples, the substrate may be spun-bonded, melt-bonded, or point bonded or combinations of bonding processes may be chosen. The substrate breaking strength and elasticity in the machine and cross direction is sufficient to enable the substrate to be conveyed through a coating process. The porosity of the substrate article is sufficient to enable air flow through the substrate to promote conditioning active release and prevent dryer vent blinding. The substrate may also have a plurality of rectilinear slits extended along one dimension of the substrate.

The dispensing means will normally carry an effective amount of fabric conditioning composition. Such effective amount typically provides sufficient softness, antistatic effect and/or perfume deposition for at least one treatment of a minimum load in an automatic laundry dryer. Amounts of the fabric conditioning composition irrespective of load size for a single article can vary from about 0.1 g to about 100 g, preferably from about 0.1 g to about 20 g, most preferably from about 0.1 g to about 10 g. Amounts of fabric treatment composition for multiple uses, e.g., up to about 30, can be used.

Absorbent Article, Polybag or Paper Carton and Methods of Use

Preferably said consumer product is an article selected from an absorbent article, polybag or paper carton, said article comprising, based on total article weight, with from 0.001% about to about 25%, preferably from about 0.01% to about 10%, more preferably from about 0.05% to about 5%, most preferably from about 0.1% to about 0.5% of the microcapsules of the present invention.

Preferably said article is an absorbent article, preferably said absorbent article is a sanitary paper product, said sanitary paper product comprising one or more layers of conventional felt-pressed tissue paper, conventional wet-pressed tissue paper, pattern densified tissue paper, starch substrates, high bulk, un-compacted tissue paper and mixtures thereof.

Preferably said absorbent article comprises an absorbent core, and optionally a backsheet, topsheet, acquisition layer or outer wrapper, wherein said microcapsules are disposed on the absorbent core or between one or more of the optional layers.

In one aspect of said article, said absorbent article is contained in a polybag or paper carton.

In one aspect of said article, said microcapsules are disposed on said polybag or paper carton, and/or on said absorbent article.

Preferably said article is an absorbent article comprises a lotion.

Preferably, said absorbent article comprises one or more adjunct ingredients selected from the group consisting of surfactants, inks, dyes, mineral oils, petrolatum, polysiloxanes, cyclodextrins, clays, silicates, aluminates, vitamins, isoflavones, flavones, metal oxides, short chain organic acids ($C_1$-$C_8$), triglycerides ($C_8$-$C_{22}$), and antioxidants.

In one aspect, a method of providing a benefit agent, preferably perfume, comprising: incorporating said microcapsules in or on an article, preferably an absorbent article, polybag and/or paper carton, is disclosed.

A non-limiting list of suppliers of suitable absorbent articles, polybags, and cartons that can be used in the manufacture of Applicants' articles is as follows: Procter & Gamble of Cincinnati, Ohio, USA; International Paper Products of Memphis, Tenn. USA; and Kimberly Clark, of Irving, Tex., USA. Suitable equipment and processes for making absorbent articles can be obtained from Fameccanica Group of Pescara, Italy. Suitable equipment and processes for adding the malodor reduction materials to said articles can be obtained from Nordson of Duluth Ga., USA.

Personal Care Compositions and Methods of Use

Preferably said consumer product is a personal care composition comprising, based on total composition weight,
  (a) with from 0.001% about to about 10%, preferably from about 0.1% to about 5%, more preferably from about 0.5% to about 4%, most preferably from about 1% to about 3% of the microcapsules disclosed here in;
  (b) from about 0.1% to about 99%, preferably from about 1% to about 80%, more preferably from about 5% to about 70%, most preferably from about 10% to about 50% of a solvent, preferably said solvent is selected from, water, glycerin, and mixtures thereof; and
  (c) from about 0% to about 50%, preferably from about 0% to about 40%, more preferably from about 0.1% to about 30%, most preferably from about 0.1% to about 15% of a material selected from the group consisting of a structurant, a humectant, a surfactant, an antimicrobial, and mixtures thereof.

Preferably, said personal care composition comprises one or more neat perfume raw materials—the total of said neat perfume raw materials being the sum of such neat perfume raw materials based on weight of each neat perfume raw materials.

Preferably, said sum total of neat perfume raw materials has an average Log P, based on weight percent of each perfume raw material in said sum total of neat perfume raw materials, of from about 2.5 to about 8, preferably from about 3 to about 8, more preferably from about 3.5 to about 7, most preferably, each of said neat perfume raw materials in said sum total of neat perfume raw materials. This range of Log P will allow the perfume to deposit on the skin and not wash away in the water phase during use Preferably said personal care composition, comprises less than 10%, preferably less than 5%, more preferably less than 1% of said one or more perfume raw materials, based on total combined weight of said one or more perfume raw materials comprise an ionone moiety.

Preferably said personal care composition comprises a total of, based on total personal care composition weight, of from about 3% to 30% of a surfactant, and, optionally, a miscellar phase and/or lamellar phase.

Preferably said personal care composition, said composition comprises a total, based on total personal care composition weight, of from about 0.1% to about 50% of a material selected from structurants, humectants, fatty acids, inorganic salts, antimicrobial agents, antimicrobial agents actives and mixtures thereof.

Preferably said personal care composition comprises an adjunct ingredient selected from the group consisting of clay mineral powders, pearl pigments, organic powders, emulsifiers, distributing agents, pharmaceutical active, topical active, preservatives, surfactants and mixtures thereof.

A method of freshening comprising: contacting a situs with a personal care composition selected from the group consisting of the personal care compositions disclosed herein is disclosed.

In one aspect of said method, said situs comprises the body or head of hair and said contacting step comprises contacting said body or hair containing a malodor with a sufficient amount of Applicants' personal care composition to provide said body or hair with a level of encapsulated benefit agent, preferably perfume, of at least 0.0001 mg of encapsulated benefit agent per body or head of hair, preferably from about 0.0001 mg of encapsulated benefit agent per body or head of hair to about 1 mg of encapsulated benefit agent per body or head of hair, more preferably from about 0.001 mg of encapsulated benefit agent per body or head of hair about 0.5 mg of encapsulated benefit agent per body or head of hair, most preferably from about 0.01 of encapsulated benefit agent per body or head of hair to about 0.2 mg of encapsulated benefit agent per body or head of hair.

Antiperspirant and/or Deodorant Compositions and Methods of Use

Preferably said consumer product is an antiperspirant and/or deodorant composition comprising, based on total composition weight,
  (a) with from 0.001% about to about 10%, preferably from about 0.1% to about 5%, more preferably from about 0.5% to about 4%, most preferably from about 1% to about 3% of the microcapsules disclosed here in;
  (b) from about 0.1% to about 99%, preferably from about 1% to about 80%, more preferably from about 5% to about 55%, most preferably from about 10% to about 50% of a solvent, preferably said solvent is selected from cyclopentasiloxane, ethanol, water, propylene glycol, dipropylene glycol, and mixtures thereof;
  (c) from about 0% to about 30%, preferably from about 0% to about 20%, more preferably from about 0.1% to about 4%, most preferably from about 0.1% to about 4% of a material selected from the group consisting of a structurant, a residue masker, an antimicrobial, and mixtures thereof is disclosed. The aforementioned solvent levels help disperse perfume into the APDO base to give even coverage when used Preferably said antiperspirant and/or deodorant composition, comprises one or more perfume raw materials.

Preferably each of said one or more perfume raw materials has a boiling point of from about 160° C. to about 400° C., preferably from about 180° C. to about 400° C.

Preferably less than 10%, preferably less than 5%, more preferably less than 1% of said one or more perfume raw materials, based on total combined weight of said one or more perfume raw materials comprise an ionone moiety.

Preferably, said antiperspirant and/or deodorant composition is an antiperspirant composition that comprises a total of, based on total antiperspirant composition weight, from about 1% to about 25% of an aluminum salt antiperspirant active.

Preferably said antiperspirant and/or deodorant composition, is an anhydrous antiperspirant composition, said anhydrous antiperspirant composition comprising a total of, based on total anhydrous antiperspirant composition weight, from about 1% to about 25% of an antiperspirant actives selected from the group consisting of astringent metallic salts, preferably inorganic and organic salts of aluminum, zirconium and zinc, as well as mixtures thereof, more preferably aluminum halides, aluminum chlorohydrate, aluminum hydroxyhalides, zirconyl oxyhalides, zirconyl hydroxyhalides, and mixtures thereof.

Preferably said antiperspirant and/or deodorant composition comprises an adjunct ingredient selected from the group consisting of clay mineral powders, pearl pigments, organic powders, emulsifiers, distributing agents, pharmaceutical active, topical active, preservatives, surfactants and mixtures thereof.

A method of controlling malodors comprising: contacting a situs comprising a malodor and/or a situs that may become malodorous with an antiperspirant or deodorant composition selected from the group consisting of the antiperspirant and/or deodorant composition disclosed herein, is disclosed.

In one aspect of said method, said situs is an underarm and said contacting step comprises contacting said underarm with a sufficient amount of Applicants' antiperspirant and/or deodorant composition containing said sum of malodor reduction materials to provide said underarm with a level of malodor reduction materials of at least 0.0001 mg of malodor reduction material per underarm, preferably from about 0.0001 mg of malodor reduction material per underarm to about 10 mg of malodor reduction material per underarm, more preferably from about 0.001 mg of malodor reduction material per underarm about 5 mg of malodor reduction material per underarm, most preferably from about 0.01 of malodor reduction material per underarm to about 0.2 mg of malodor reduction material per underarm.

Antiperspirant Compositions

Antiperspirant compositions can be formulated in many forms. For example an antiperspirant composition can be, without limitation, a roll on product, a body spray, a stick including soft solid sticks and invisible solids, or an aerosol. Each of the antiperspirant compositions described below can include perfume materials as described herein.

A. Roll-on and Clear Gel

A roll-on antiperspirant composition can comprise, for example, water, emollient, solubilizer, deodorant actives, antioxidants, preservatives, or combinations thereof. A clear gel antiperspirant composition can comprise, for example, water, emollient, solubilizer, deodorant actives, antioxidants, preservatives, ethanol, or combinations thereof.

Water—The roll-on composition can include water. Water can be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the deodorant composition.

Emollients—Roll-on compositions can comprise an emollient system including at least one emollient, but it could also be a combination of emollients. Suitable emollients are often liquid under ambient conditions. Depending on the type of product form desired, concentrations of the emollient(s) in the deodorant compositions can range from about 1% to about 95%, from about 5% to about 95%, from about 15% to about 75%, from about 1% to about 10%, from about 15% to about 45%, or from about 1% to about 30%, by weight of the deodorant composition.

Emollients suitable for use in the roll-on compositions include, but are not limited to, propylene glycol, polypropylene glycol (like dipropylene glycol, tripropylene glycol, etc.), diethylene glycol, triethylene glycol, PEG-4, PEG-8, 1,2 pentanediol, 1,2 hexanediol, hexylene glycol, glycerin, C2 to C20 monohydric alcohols, C2 to C40 dihydric or polyhydric alcohols, alkyl ethers of polyhydric and monohydric alcohols, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Deodorant Actives—Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. The concentration of the optional deodorant active may range from about 0.001%, from about 0.01%, of from about 0.1%, by weight of the composition to about 20%, to about 10%, to about 5%, or to about 1%, by weight of the composition.

Odor Entrappers—The composition can include an odor entrapper. Suitable odor entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

Buffering Agent—The composition can include a buffering agent which may be alkaline, acidic or neutral. The buffer can be used in the composition for maintaining the desired pH. The composition may have a pH from about 3 to about 10, from about 4 to about 9, from about 5 to about 8, from about 6 to about 7, or it may have a pH of about 6.5. One unique feature of the polyvinyl amine malodor control polymers is its ability to maintain active nitrogen sites at high pH levels which can help enhance the antibacterial effect which comes, at least in part, from the nitrogen sites. Suitable buffering agents include, for example, hydrochloric acid, sodium hydroxide, potassium hydroxide, and combinations thereof.

The compositions can contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer—The composition can contain a solubilizer. A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof.

Suitable solubilizers include, for example, hydrogenated castor oil, polyoxyethylene 2 stearyl ether, polyoxyethylene 20 stearyl ether, and combinations thereof. One suitable hydrogenated castor oil that may be used in the present composition is polyoxyethylene hydrogenated castor oil.

When the solubilizing agent is present, it is typically present at a level of from about 0.01% to about 5%, alternatively from about 0.01% to about 3%, alternatively from about 0.05% to about 1%, alternatively from about 0.01% to about 0.05%, by weight of the composition.

Preservatives—The composition can include a preservative. The preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxymethyl) urea, commonly known as diazolidinyl urea, available under the trade name Germall® II from Sutton Laboratories, Inc.; N,N''-methylenebis{N'-[1-(hydroxymethyl)-2,5-dioxo-4-imidazolidinyl]-urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

B. Body Spray

A body spray can contain, for example, a carrier, perfume, a deodorant active, odor entrappers, propellant, or combinations thereof. The body spray compositions can be applied as a liquid.

Carrier—A carrier suitable for use in a body spray can include, water, alcohol, or combinations thereof. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. A suitable example of an alcohol can include ethanol.

Propellant—The compositions described herein can include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42%, or any combination thereof, by weight of the total fill of materials stored within the container.

C. Invisible Solid

Invisible solid antiperspirant compositions as described herein can contain a primary structurant, an antiperspirant active, a perfume, and additional chassis ingredient(s). The antiperspirant composition can further comprise other optional ingredient(s). The compositions can be in the form of a solid stick. The compositions can have a product hardness of about 600 gram force or more. The compositions may be free of dipropylene glycol, added water, castor wax, or any combination thereof. The antiperspirant composition may be anhydrous. The antiperspirant composition may be free of added water.

Hardness—The invisible solid can have a product hardness of least about 600 gram-force, more specifically from about 600 gram-force to about 5,000 gram-force, still more specifically from about 750 gram-force to about 2,000 gram-force, and yet more specifically from about 800 gram-force to about 1,400 gram-force.

The term "product hardness" or "hardness" as used herein is a reflection of how much force is required to move a penetration cone a specified distance and at a controlled rate into an antiperspirant composition under the test conditions described herein below. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Primary Structurants—The invisible solid can comprise a suitable concentration of a primary structurant to help provide the antiperspirant with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the antiperspirant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Other non-limiting examples of primary structurants suitable for use herein are described in U.S. Pat. Nos. 5,976,514 and 5,891,424, the descriptions of which are incorporated herein by reference.

Antiperspirant Active—The antiperspirant stick compositions can comprise a particulate antiperspirant active suitable for application to human skin. The concentration of antiperspirant active in the composition should be sufficient to provide the desired perspiration wetness and odor control from the antiperspirant stick formulation selected.

The antiperspirant stick compositions can comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about 10 microns.

The antiperspirant active for use in the anhydrous antiperspirant compositions of the present invention can include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_aCl_b \cdot xH_2O,$$

wherein a is from about 2 to about 5; the sum of a and b is about 6; x is from about 1 to about 6; and a, b, and x may have non-integer values. More specifically, aluminum chlorohydroxides referred to as "5/6 basic chlorohydroxide" can be used, wherein a=5, and "2/3 basic chlorohydroxide", wherein a=4. Processes for preparing aluminum salts are disclosed in U.S. Pat. Nos. 3,887,692; 3,904,741; 4,359,456; and British Patent Specification 2,048,229, the disclosures of which are incorporated herein by reference for the purpose of describing processes for preparing aluminum salts. Mixtures of aluminum salts are described in British Patent Specification 1,347,950, which description is also incorporated herein by reference.

Zirconium salts for use in the anhydrous antiperspirant stick compositions include those which conform to the formula:

$$ZrO(OH)_{2-a}Cl_a \cdot xH_2O,$$

wherein a is from about 1.5 to about 1.87; x is from about 1 to about 7; and a and x may both have non-integer values. These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068; Great Britain Patent Application 2,144,992; and U.S. Pat. No. 4,120,948, disclosures of which are incorporated herein by reference for the limited purpose of describing ZAG complexes.

Also suitable for use herein are enhanced efficacy aluminum-zirconium chlorohydrex-amino acid which typically has the empirical formula:

$$Al_n Zr(OH)_{[3n+4-m(n+1)]}(Cl)_{[m(n+1)]} \cdot AA_q$$

where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

Additional Chassis Ingredients

Additional Structurant—The antiperspirant composition can further comprise an additional structurant. The additional structurant may be present in an amount from 1% to about 10%, by weight of the composition.

The additional structurant(s) will likely be present at an amount less than the primary structurant. Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof. Other non-limiting examples of additional structurants suitable for use herein are described in U.S. Pat. Nos. 5,976,514 and 5,891,424.

Solvent—The antiperspirant composition can comprise a solvent at concentrations ranging from about 20% to about 80%, and more specifically from about 30% to about 70%, by weight of the composition. The solvent can be a volatile silicone which may be cyclic or linear. "Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference. The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C. The volatile silicone can also be linear, suitable volatile linear silicone materials for use in the antiperspirant compositions include those represented by the formula:

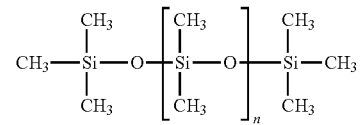

wherein n is from 1 to 7, and more specifically from 2 to 3. These linear silicone materials will generally have viscosities of less than about 5 centistokes at 25° C. Specific examples of volatile silicone solvents suitable for use in the antiperspirant compositions include, but are not limited to, Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids—Non-volatile organic fluids may be present, for example, in an amount of about 15% or less, by weight of the composition. Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Adjunct Ingredients—The anhydrous antiperspirant compositions can further comprise any optional material that is known for use in antiperspirant and deodorant compositions or other personal care products, or which is otherwise suitable for topical application to human skin. One example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof. Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition. Nonlimiting examples of other optional materials include emulsifiers, distributing agents, antimicrobials, pharmaceutical or other topical active, preservatives, surfactants, and so forth. Examples of such optional materials are described in U.S. Pat. Nos. 4,049,792; 5,019,375; and 5,429,816; which descriptions are incorporated herein by reference.

D. Soft Solid

Soft solid composition can comprise volatile silicone, antiperspirant active, gellant, residue masking material, or combinations thereof. In addition, soft solids generally have a hardness value after dispensing of about 500 gram force or less.

Volatile Silicone Solvent—The soft solid can comprises a volatile silicone solvent at concentrations ranging from about 20% to about 80%, preferably from about 30% to about 70%, more preferably from about 45% to about 70%, by weight of the composition. The volatile silicone of the solvent may be cyclic or linear.

"Volatile silicone" as used herein refers to those silicone materials which have measurable vapor pressure under ambient conditions. Nonlimiting examples of suitable volatile silicones are described in Todd et al., "Volatile Silicone Fluids for Cosmetics", Cosmetics and Toiletries, 91:27-32 (1976), which descriptions are incorporated herein by reference. Preferred volatile silicone materials are those having from about 3 to about 7, preferably from about 4 to about 5, silicon atoms. Cyclic volatile silicones are preferred for use in the antiperspirant compositions herein, and include those represented by the formula:

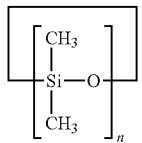

wherein n is from about 3 to about 7, preferably from about 4 to about 5, most preferably 5. These cyclic silicone materials will generally have viscosities of less than about 10 centistokes at 25° C. Linear volatile silicone materials suitable for use in the antiperspirant compositions include those represented by the formula:

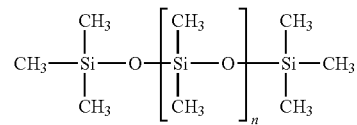

wherein n is from about 1 to about 7, preferably from about 2 to about 3. These linear silicone materials will generally have viscosities of less than about 5 centistokes at 25° C. Specific examples of volatile silicone solvents suitable for use in the antiperspirant compositions include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicones Corp.).

Gellant Material—The soft solid can include a gellant material comprising fatty alcohols having from about 20 to about 60 carbon atoms, or combinations thereof, at concentrations ranging from about 0.1% to about 8% by weight of the composition. The gellant material, when combined with the volatile silicone solvent described hereinbefore, provides the composition with a physically stable structure within which the particulate antiperspirant materials are dispersed, and maintained as such over an extended period of time. Specifically, the gellant material can comprise saturated or unsaturated, substituted or unsubstituted, fatty alcohols or mixtures of fatty alcohols having from about 20 to about 60 carbons atoms, preferably from about 20 to about 40 carbon atoms. Preferred are combinations of the fatty alcohols. The fatty alcohol gellants are preferably saturated, unsubstituted monohydric alcohols or combinations thereof, which have a melting point of at less than about 110° C., more preferably from about 60° to about 110° C., even more preferably between about 100° C. and 110° C.

It has been found that this fatty alcohol-based gellant material, when combined with volatile silicone solvents provides a stable structure for maintaining a dispersion of particulate antiperspirant material in a topical formulation without the necessity of using conventional particulate thickening agents. This gellant material is especially useful in maintaining the physical stability of particulate dispersions containing higher concentrations of volatile silicone solvents.

It was also found that penetration force values for the antiperspirant compositions can be controlled by adjusting total fatty alcohol concentrations. In controlling penetration force values in this manner, there is no longer a need to use organic solvents or thickening agents to control penetration force values, which solvents or thickening agents often add cost to the formulation, introduce additional compatibility issues, and often contribute undesirable cosmetics such as prolonged stickiness, difficulty in ease of spreading, increased dry-down times and reduced dry feel after application.

Specific concentrations of the gellant materials can be selected according to the desired penetration force value. For roll-on formulations having a penetration force value of from about 20 gram·force to about 100 gram·force, gellant material concentrations preferably range from about 0.1% to about 3%, preferably from about 1.5% to about 3%, by weight of the antiperspirant composition. For other cream formulations, including those formulations suitable for use in cream applicator devices, which have a penetration force value of from about 100 gram·force to about 500 gram·force, gellant material concentrations preferably range from about 3% to about 8%, preferably from about 3% to about 6%, by weight of the antiperspirant composition.

Specific examples of fatty alcohol gellants for use in the antiperspirant compositions that are commercially available include, but are not limited to, Unilin® 425, Unilin® 350, Unilin®550 and Unilin® 700 (supplied by Petrolite)

Residue Masking Material—The soft solid compositions can further comprise a nonvolatile emollient as a residue masking material. Such materials and their use in antiperspirant products are well known in the antiperspirant art, and any such material may be incorporated into the composition of the present invention, provided that such optional material is compatible with the essential elements of the composition, or does not unduly impair product performance or cosmetics. Concentrations of the optional residue masking material can range from about 0.1% to about 40%, preferably from about 1% to about 10%, by weight of the antiperspirant composition. These optional materials can be liquid at ambient temperatures, and can be nonvolatile. The term "nonvolatile" as used in this context refers to materials which have a boiling point under atmospheric pressure of at least about 200° C. Non-limiting examples of suitable residue masking materials for use in the antiperspirant products include butyl stearate, diisopropyl adipate, petrolatum, nonvolatile silicones, octyldodecanol, phenyl trimethicone, isopropyl myristate, C12-15 ethanol benzoates and PPG-14 Butyl Ether. Residue masking materials are described, for example, in U.S. Pat. No. 4,985,238, which description is incorporated herein by reference.

Other Materials—The soft solid compositions can further comprise one, or more, other materials which modify the physical characteristics of the compositions or serve as additional "active" components when deposited on the skin. Many such materials are known in the antiperspirant art and can be used in the antiperspirant compositions herein, provided that such optional materials are compatible with the essential materials described herein, or do not otherwise unduly impair product performance. Non limiting examples of materials can include active components such as bacteriostats and fungiostats, and "non-active" components such as colorants, perfumes, cosmetic powders, emulsifiers, chelants, distributing agents, preservatives, and wash-off aids. Examples of such optional materials are described in U.S. Pat. No. 4,049,792; Canadian Patent 1,164,347; U.S. Pat. Nos. 5,019,375; and 5,429,816; which descriptions are incorporated herein by reference.

E. Aerosol

An aerosol composition can comprise a concentrate, a propellant, or a combination thereof. Alcohol is a predominant component of the concentrates provided herein. Useful alcohols include $C_1$-$C_3$ alcohols, with the preferred alcohol being ethanol. In certain examples, the alcohol is employed at a concentration level of from at least about 40%, 50% or 55% to about 80%, by weight of the concentrate.

An antiperspirant active is dissolved in the alcohol, at a level of from about 1% to about 15%, by weight of the concentrate. Various antiperspirant actives can be employed, including, for example, aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY. In one example, aluminum chlorohydrex PG is the chosen antiperspirant active.

The antiperspirant concentrates can also include an oil or a mixture of two or more oils. Useful oils include, for example, volatile silicone oils and non-volatile organic oils. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone can be a cyclic silicone having from at least about 3 silicone atoms or from at least about 5 silicone atoms but no more than about 7 silicone atoms or no more than about 6 silicone atoms. For example, volatile silicones can be used which conform to the formula:

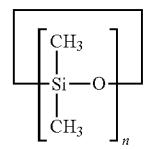

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); MASIL SF-V (available from Mazer) and combinations thereof. Suitable volatile silicone oils can also include linear silicone oils such as, for example, DC200 (1 cSt), DC200 (0.65 cSt), and DC2-1184, all of which are available from Dow Corning Corp. In certain examples, the volatile silicone oil can have a viscosity of less than 10 centistokes at 25° C.

Non-volatile organic, emollient oils can also be employed. A representative, non-limiting list of emollient oils includes CETIOL CC (dicaprylyl carbonate), CETIOL OE (dicaprylyl ether), CETIOL S (diethylhexylcyclohexane), and CETIOL B (dibutyl adipate), all of which are available from Cognis, and LEXFEEL 7 (neopentyl glycol diheptanoate) from Inolex. In certain examples, the organic emollient oils have a viscosity of less than 50 centistokes at 25° C. The term "organic emollient oil" as used herein means silicon-free emollient oils that are liquid at 25° C., and that are safe and light to skin and can be miscible with volatile silicone oils (as described above) and the antiperspirant active-alcohol solution in the concentration ranges described below. The oil or mixture of oils is generally included in the concentrate formulas at a level of from about 5% to about 45%, by weight of the concentrate. This viscosity ranges noted above in connection with the different classes of oil can facilitate desired spray rates and patterns, and can help minimize nozzle clogging. To provide desired skin feel, minimal nozzle clogging, and good concentrate stability, the ratio of alcohol to volatile silicone oil is preferably greater than 1.0, 1.35, or 1.5. And in examples having both a volatile silicone oil and an organic emollient oil, the ratio of alcohol to total oil is preferably greater than or equal to about 0.90. The oils in certain examples are miscible with the alcohol and antiperspirant active solution. Although various levels of miscibility are acceptable, the oils are preferably miscible enough with the alcohol and antiperspirant active solution to yield a concentrate having a clear appearance.

The antiperspirant compositions can also include residue-masking agents and propellants as discussed above.

Additional Consumer Product Ingredients/Adjunct Materials

While not essential for the purposes of the present invention, the non-limiting list of consumer product ingredients/adjuncts illustrated hereinafter are suitable for use in the instant compositions and may be desirably incorporated in certain aspects of the invention, for example to assist or enhance cleaning performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the fabric treatment operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents, pigments and/or fabric softener actives and clothes softening agents compatible with detergents, anti-bacterials, anti-microbials, and anti-fungals.

As stated, the adjunct ingredients are not essential to Applicants' compositions. Thus, certain aspects of Applicants' compositions do not contain one or more of the following adjuncts materials: surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems structure elasticizing agents, carriers, hydrotropes, processing aids, solvents, pigments and/or fabric softener actives, anti-bacterial/microbial. However, when one or more adjuncts are present, such one or more adjuncts may be present as detailed below.

Rheology Modifier—The liquid compositions of the present invention may comprise a rheology modifier. The rheology modifier may be selected from the group consisting of non-polymeric crystalline, hydroxy-functional materials, polymeric rheology modifiers which impart shear thinning characteristics to the aqueous liquid matrix of the composition. In one aspect, such rheology modifiers impart to the aqueous liquid composition a high shear viscosity, at 20 $sec^{-1}$ shear rate and at 21° C., of from 1 to 7000 cps and a viscosity at low shear (0.5 see shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 $sec^{-1}$ and at 21° C., of from 50 to 3000 cps and a viscosity at low shear (0.5 $sec^{-1}$ shear rate at 21° C.) of greater than 1000 cps, or even 1000 cps to 200,000 cps. Viscosity according to the present invention is measured using an AR 2000 rheometer from TA instruments using a plate steel spindle having a plate diameter of 40 mm and a gap size of 500 μm. The high shear viscosity at 20 $sec^{-1}$ and low shear viscosity at 0.5 $sec^{-1}$ can be obtained from a logarithmic shear rate sweep from 0.1 see to 25 see in 3 minutes time at 21° C. Crystalline hydroxyl functional materials are rheology modifiers which form thread-like structuring systems throughout the matrix of the composition upon in situ crystallization in the matrix. Polymeric rheology modifiers are preferably selected from polyacrylates, polymeric gums, other non-gum polysaccharides, and combinations of these polymeric materials. Generally the rheology modifier will comprise from 0.01% to 1% by weight, preferably from 0.05% to 0.75% by weight, more preferably from 0.1% to 0.5% by weight, of the compositions herein.

Structuring agents which are especially useful in the compositions of the present invention may comprise non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. In one aspect, rheology modifiers include crystalline, hydroxyl-containing rheology modifiers include castor oil and its derivatives. In one aspect, rheology modifiers include hydrogenated castor oil derivatives such as hydrogenated castor oil and hydrogenated castor wax. Commercially available, castor oil-based, crystalline, hydroxyl-containing rheology modifiers include THIXCIN™ from Rheox, Inc. (now Elementis).

Other types of rheology modifiers, besides the non-polymeric, crystalline, hydroxyl-containing rheology modifiers described heretofore, may be utilized in the liquid detergent compositions herein. Polymeric materials which provide shear-thinning characteristics to the aqueous liquid matrix may also be employed. Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum. If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by CP Kelco U.S., Inc. under the KELCOGEL tradename.

A further alternative and suitable rheology modifier include a combination of a solvent and a polycarboxylate polymer. More specifically the solvent may be an alkylene glycol. In one aspect, the solvent may comprise dipropylene glycol. In one aspect, the polycarboxylate polymer may comprise a polyacrylate, polymethacrylate or mixtures thereof. In one aspect, solvent may be present, based on total composition weight, at a level of from 0.5% to 15%, or from 2% to 9% of the composition. In one aspect, polycarboxylate polymer may be present, based on total composition weight, at a level of from 0.1% to 10%, or from 2% to 5%. In one aspect, the solvent component may comprise mixture of dipropylene glycol and 1,2-propanediol. In one aspect, the ratio of dipropylene glycol to 1,2-propanediol may be 3:1 to 1:3, or even 1:1. In one aspect, the polyacrylate may comprise a copolymer of unsaturated mono- or di-carbonic acid and $C_1$-$C_{30}$ alkyl ester of the (meth) acrylic acid. In another aspect, the rheology modifier may comprise a polyacrylate of unsaturated mono- or di-carbonic acid and $C_1$-$C_{30}$ alkyl ester of the (meth) acrylic acid. Such copolymers are available from Noveon Inc under the tradename Carbopol Aqua 30®.

In the absence of rheology modifier and in order to impart the desired shear thinning characteristics to the liquid composition, the liquid composition can be internally structured through surfactant phase chemistry or gel phases.

Hueing Dye—The liquid laundry detergent composition may comprise a hueing dye. The hueing dyes employed in the present laundry care compositions may comprise polymeric or non-polymeric dyes, organic or inorganic pigments, or mixtures thereof. Preferably the hueing dye comprises a polymeric dye, comprising a chromophore constituent and a polymeric constituent. The chromophore constituent is characterized in that it absorbs light in the wavelength range of blue, red, violet, purple, or combinations thereof upon exposure to light. In one aspect, the chromophore constituent exhibits an absorbance spectrum maximum from about 520 nanometers to about 640 nanometers in water and/or methanol, and in another aspect, from about 560 nanometers to about 610 nanometers in water and/or methanol.

Although any suitable chromophore may be used, the dye chromophore is preferably selected from benzodifuranes, methine, triphenylmethanes, napthalimides, pyrazole, naptho-quinone, anthraquinone, azo, oxazine, azine, xanthene, triphenodioxazine and phthalocyanine dye chromophores. Mono and di-azo dye chromophores are may be preferred.

The hueing dye may comprise a dye polymer comprising a chromophore covalently bound to one or more of at least three consecutive repeat units. It should be understood that the repeat units themselves do not need to comprise a chromophore. The dye polymer may comprise at least 5, or at least 10, or even at least 20 consecutive repeat units. The repeat unit can be derived from an organic ester such as phenyl dicarboxylate in combination with an oxyalkyleneoxy and a polyoxyalkyleneoxy. Repeat units can be derived from alkenes, epoxides, aziridine, carbohydrate including the units that comprise modified celluloses such as hydroxyalkylcellulose; hydroxypropyl cellulose; hydroxypropyl methylcellulose; hydroxybutyl cellulose; and, hydroxybutyl methylcellulose or mixtures thereof. The repeat units may be derived from alkenes, or epoxides or mixtures thereof. The repeat units may be $C_2$-$C_4$ alkyleneoxy groups, sometimes called alkoxy groups, preferably derived from $C_2$-$C_4$ alkylene oxide. The repeat units may be $C_2$-$C_4$ alkoxy groups, preferably ethoxy groups. For the purposes of the present invention, the at least three consecutive repeat units form a polymeric constituent. The polymeric constituent may be covalently bound to the chromophore group, directly or indirectly via a linking group. Examples of suitable polymeric constituents include polyoxyalkylene chains having multiple repeating units. In one aspect, the polymeric constituents include polyoxyalkylene chains having from 2 to about 30 repeating units, from 2 to about 20 repeating units, from 2 to about 10 repeating units or even from about 3 or 4 to about 6 repeating units. Non-limiting examples of polyoxyalkylene chains include ethylene oxide, propylene oxide, glycidol oxide, butylene oxide and mixtures thereof.

Surfactants—The compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. The surfactant is typically present at a level of from about 0.1% to about 60%, from about 1% to about 50% or even from about 5% to about 40% by weight of the subject composition.

Chelating Agents—The compositions herein may contain a chelating agent. Suitable chelating agents include copper, iron and/or manganese chelating agents and mixtures thereof. When a chelating agent is used, the composition may comprise from about 0.1% to about 15% or even from about 3.0% to about 10% chelating agent by weight of the subject composition.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Perfumes—The consumer product may comprise, either in neat form or via a delivery system, a perfume raw materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, α-damascone, β-damascone, γ-damascone, Δ-damascenone, 6,7-dihydro-1,1,2,3,3-pentamethyl-4 (5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and β-dihydro ionone, linalool, ethyllinalool, tetrahydrolinalool, and dihydromyrcenol.

Additional Perfume Delivery Technologies—The compositions of the present invention may comprise one or more perfume delivery technologies that stabilize and enhance the deposition and release of perfume ingredients from treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

In one aspect, the compositions of the present invention may comprise from about 0.001% to about 20%, preferably from about 0.01% to about 10%, more preferably from about 0.05% to about 5%, most preferably from about 0.1% to about 0.5% by weight of the perfume delivery technology. In one aspect, said perfume delivery technologies may be selected from the group consisting of: pro-perfumes, polymer particles, functionalized silicones, polymer assisted delivery, molecule assisted delivery, fiber assisted delivery, amine assisted delivery, cyclodextrins, starch encapsulated accord, zeolite and inorganic carrier, additional perfume microcapsules, and mixtures thereof:

In one aspect, said perfume delivery technology may comprise an additional encapsulated perfume such as additional perfume microcapsules formed by at least partially surrounding a benefit agent with a wall material. Said benefit agent may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, $\alpha$-damascone, $\beta$-damascone, damascone, $\gamma$-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and $\beta$-dihydro ionone, linalool, ethyllinalool, tetrahydrolinalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine cross-linked with formaldehyde, melamine-dimethoxyethanol crosslinked with formaldehyde, and mixtures thereof. In one aspect, said polystyrene wall material may comprise polyestyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, the microcapsule may be a perfume microcapsule. In one aspect, one or more types of microcapsules, for example two microcapsules types having different benefit agents may be used.

In one aspect, said perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product. Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Non-limiting examples of polymeric amines include polymers based on polyalkylimines, such as polyethyleneimine (PEI), or polyvinylamine (PVAm). Non-limiting examples of monomeric (non-polymeric) amities include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Suitable Fabric Softening Actives

The fluid fabric enhancer compositions disclosed herein comprise a fabric softening active ("FSA"). Suitable fabric softening actives, include, but are not limited to, materials selected from the group consisting of quaternary ammonium compounds, amines, fatty esters, sucrose esters, silicones, dispersible polyolefins, clays, polysaccharides, fatty acids, softening oils, polymer latexes and mixtures thereof.

Non-limiting examples of water insoluble fabric care benefit agents include dispersible polyethylene and polymer latexes. These agents can be in the form of emulsions, latexes, dispersions, suspensions, and the like. In one aspect, they are in the form of an emulsion or a latex. Dispersible polyethylenes and polymer latexes can have a wide range of particle size diameters ($\chi_{50}$) including but not limited to from about 1 nm to about 100 μm; alternatively from about 10 nm to about 10 μm. As such, the particle sizes of dispersible polyethylenes and polymer latexes are generally, but without limitation, smaller than silicones or other fatty oils.

Generally, any surfactant suitable for making polymer emulsions or emulsion polymerizations of polymer latexes can be used to make the water insoluble fabric care benefit agents of the present invention. Suitable surfactants consist of emulsifiers for polymer emulsions and latexes, dispersing agents for polymer dispersions and suspension agents for polymer suspensions. Suitable surfactants include anionic, cationic, and nonionic surfactants, or combinations thereof. In one aspect, such surfactants are nonionic and/or anionic surfactants. In one aspect, the ratio of surfactant to polymer in the water insoluble fabric care benefit agent is about 1:100 to about 1:2; alternatively from about 1:50 to about 1:5, respectively. Suitable water insoluble fabric care benefit agents include but are not limited to the examples described below.

Quats—Suitable quats include but are not limited to, materials selected from the group consisting of ester quats, amide quats, imidazoline quats, alkyl quats, amidoester quats and mixtures thereof. Suitable ester quats include but are not limited to, materials selected from the group consisting of monoester quats, diester quats, triester quats and mixtures thereof. In one aspect, a suitable ester quat is bis-(2-hydroxypropyl)-dimethylammonium methylsulfate fatty acid ester having a molar ratio of fatty acid moieties to amine moieties of from 1.85 to 1.99, an average chain length of the fatty acid moieties of from 16 to 18 carbon atoms and an iodine value of the fatty acid moieties, calculated for the free fatty acid, which has an Iodine Value of between 0-140, preferably 5-100, more preferably 10-80, even more preferably 15-70, even more preferably 18-55, most preferably 18-25. When a soft tallow quaternary ammonium compound softener is used, most preferably range is 25-60. In one aspect, the cis-trans-ratio of double bonds of unsaturated fatty acid moieties of the bis (2 hydroxypropyl)-dimethyl-ammonium methylsulfate fatty acid ester is from 55:45 to 75:25, respectively. Suitable amide quats include but are not limited to, materials selected from the group consisting of monoamide quats, diamide quats and mixtures thereof. Suitable alkyl quats include but are not limited to, materials selected from the group consisting of mono alkyl quats, dialkyl quats quats, trialkyl quats, tetraalkyl quats and mixtures thereof.

Amines—Suitable amines include but are not limited to, materials selected from the group consisting of amidoesteramines, amidoamines, imidazoline amines, alkyl amines, amidoester amines and mixtures thereof. Suitable ester amines include but are not limited to, materials selected from the group consisting of monoester amines, diester amines, triester amines and mixtures thereof. Suitable amido quats include but are not limited to, materials selected from the group consisting of monoamido amines, diamido amines and mixtures thereof. Suitable alkyl amines include but are not limited to, materials selected from the group consisting of mono alkylamines, dialkyl amines quats, trialkyl amines, and mixtures thereof.

Silicone—In one embodiment, the fabric softening composition comprises a silicone. Suitable levels of silicone may comprise from about 0.1% to about 70%, alternatively from about 0.3% to about 40%, alternatively from about 0.5% to about 30%, alternatively from about 1% to about 20% by weight of the composition. Useful silicones can be any silicone comprising compound. In one embodiment, the silicone polymer is selected from the group consisting of cyclic silicones, polydimethylsiloxanes, aminosilicones, cationic silicones, silicone polyethers, silicone resins, silicone urethanes, and mixtures thereof. In one embodiment, the silicone is a polydialkylsilicone, alternatively a polydimethyl silicone (polydimethyl siloxane or "PDMS"), or a derivative thereof. In another embodiment, the silicone is chosen from an aminofunctional silicone, amino-polyether silicone, alkyloxylated silicone, cationic silicone, ethoxylated silicone, propoxylated silicone, ethoxylated/propoxylated silicone, quaternary silicone, or combinations thereof.

In another embodiment, the silicone may be chosen from a random or blocky organosilicone polymer having the following formula:

$$[R_1R_2R_3SiO_{1/2}]_{(j+2)}[(R_4Si(X-Z)O_{2/2}]_k[R_4R_4SiO_{2/2}]_m[R_4SiO_{3/2}]_j$$

wherein:

j is an integer from 0 to about 98; in one aspect j is an integer from 0 to about 48; in one aspect, j is 0;

k is an integer from 0 to about 200, in one aspect k is an integer from 0 to about 50; when k=0, at least one of $R_1$, $R_2$ or $R_3$ is —X—Z;

m is an integer from 4 to about 5,000; in one aspect m is an integer from about 10 to about 4,000; in another aspect m is an integer from about 50 to about 2,000;

$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—Z;

each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, alkoxy and $C_1$-$C_{32}$ substituted alkoxy;

each X in said alkyl siloxane polymer comprises a substituted or unsubstituted divalent alkylene radical comprising 2-12 carbon atoms, in one aspect each divalent alkylene radical is independently selected from the group consisting of —(CH$_2$)$_s$— wherein s is an integer from about 2 to about 8, from about 2 to about 4; in one aspect, each X in said alkyl siloxane polymer comprises a substituted divalent alkylene radical selected from the group consisting of: —CH$_2$—CH(OH)—CH$_2$—; —CH$_2$—CH$_2$—CH(OH)—; and

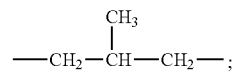

each Z is selected independently from the group consisting of

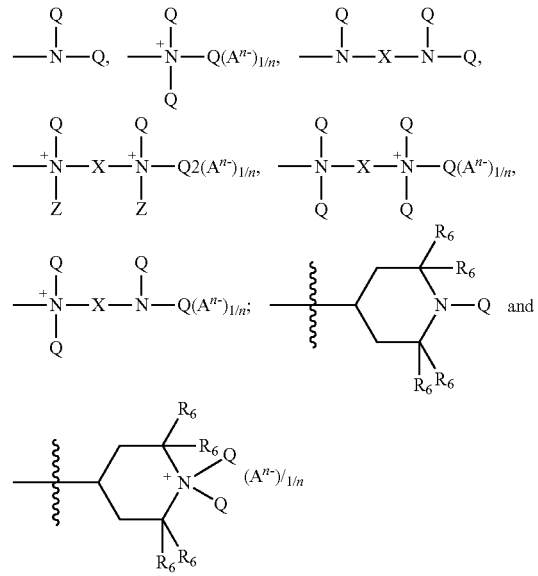

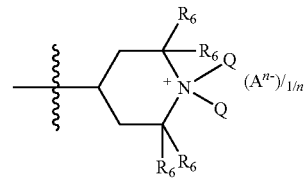

with the proviso that when Z is a quat, Q cannot be an amide, imine, or urea moiety and if Q is an amide, imine, or urea moiety, then any additional Q bonded to the same nitrogen as said amide, imine, or urea moiety must be H or a $C_1$-$C_6$ alkyl.

In one aspect, said additional Q is H. For Z, $A^{n-}$ is a suitable charge balancing anion. In one aspect $A^{n-}$ is selected from the group consisting of Cl$^-$, Br$^-$, I$^-$, methylsulfate, toluene sulfonate, carboxylate and phosphate; and at least one Q in said organosilicone is independently selected from —CH$_2$—CH(OH)—CH$_2$—R$_5$;

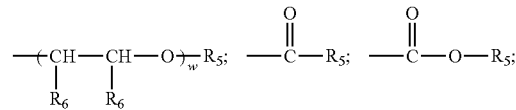

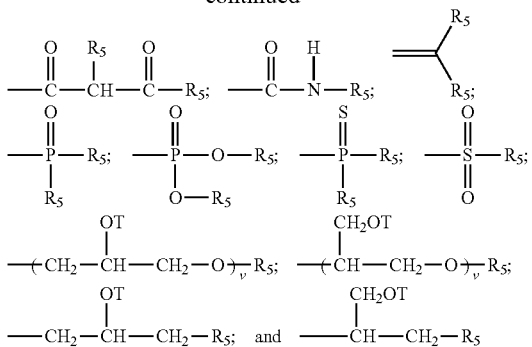

and each additional Q in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, —$CH_2$—$CH(OH)$—$CH_2$—$R_5$;

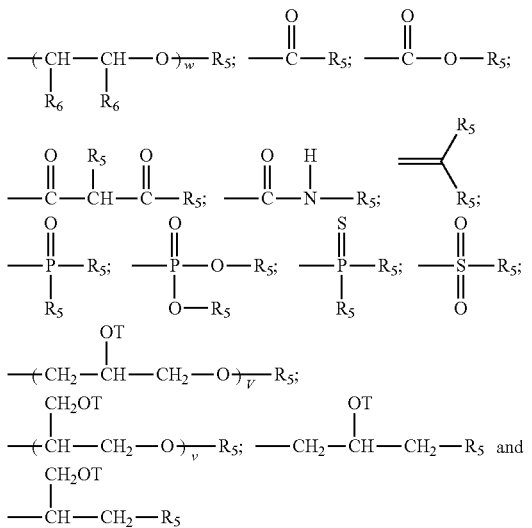

wherein each $R_5$ is independently selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, —($CHR_6$—$CHR_6$—O—)$_w$-L and a siloxyl residue;

each $R_6$ is independently selected from H, $C_1$-$C_{18}$ alkyl each L is independently selected from —C(O)—$R_7$ or $R_7$;

w is an integer from 0 to about 500, in one aspect w is an integer from about 1 to about 200; in one aspect w is an integer from about 1 to about 50;

each $R_7$ is selected independently from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl; $C_6$-$C_{32}$ substituted alkylaryl and a siloxyl residue;

each T is independently selected from H, and

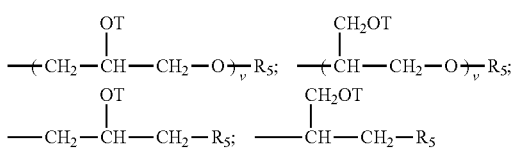

and wherein each v in said organosilicone is an integer from 1 to about 10, in one aspect, v is an integer from 1 to about 5 and the sum of all v indices in each Q in the said organosilicone is an integer from 1 to about 30 or from 1 to about 20 or even from 1 to about 10.

In another embodiment, the silicone may be chosen from a random or blocky organosilicone polymer having the following formula:

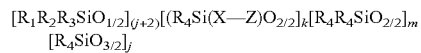

wherein j is an integer from 0 to about 98; in one aspect j is an integer from 0 to about 48; in one aspect, j is 0;

k is an integer from 0 to about 200; when k=0, at least one of $R_1$, $R_2$ or $R_3$=—X—Z, in one aspect, k is an integer from 0 to about 50 m is an integer from 4 to about 5,000; in one aspect m is an integer from about 10 to about 4,000; in another aspect m is an integer from about 50 to about 2,000;

$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—Z;

each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;

each X comprises of a substituted or unsubstituted divalent alkylene radical comprising 2-12 carbon atoms; in one aspect each X is independently selected from the group consisting of —$(CH_2)_s$—O—; —$CH_2$—$CH(OH)$—$CH_2$—O—;

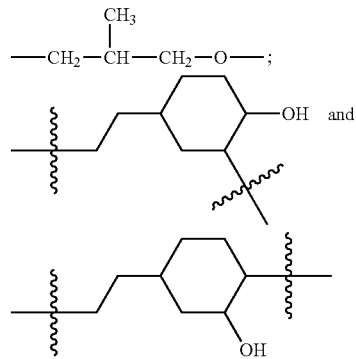

wherein each s independently is an integer from about 2 to about 8, in one aspect s is an integer from about 2 to about 4;

At least one Z in the said organosiloxane is selected from the group consisting of $R_5$;

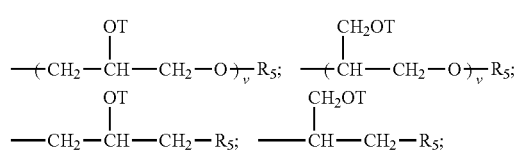

-continued

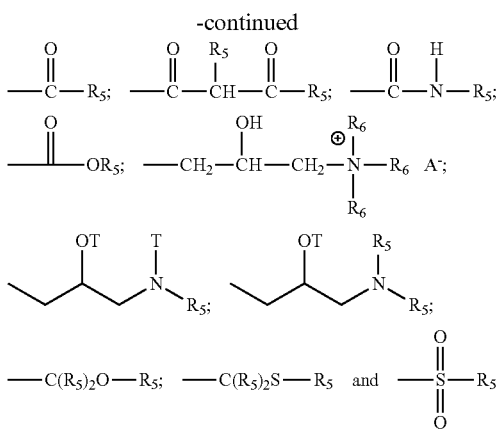

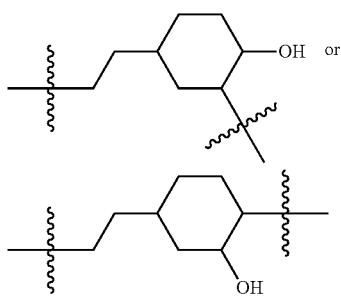

provided that when X is

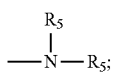

then Z=—OR₅ or $$-\underset{R_5}{\underset{|}{N}}-R_5;$$

wherein A⁻ is a suitable charge balancing anion. In one aspect A⁻ is selected from the group consisting of Cl⁻, Br⁻, I⁻, methylsulfate, toluene sulfonate, carboxylate and phosphate and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $R_5$,

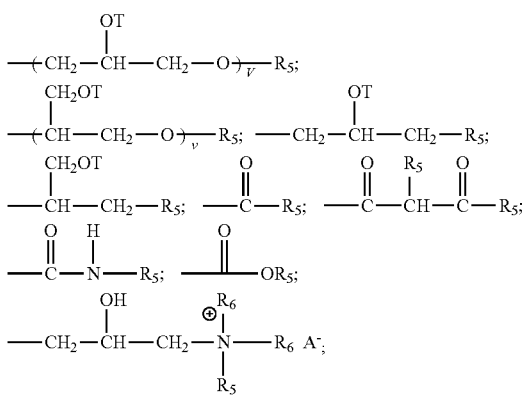

-continued

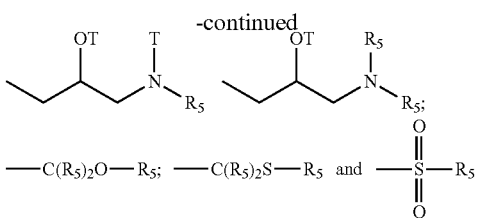

provided that when X is

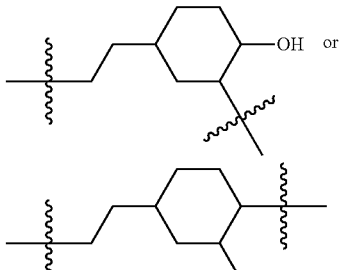

then Z=—OR₅ or

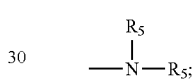

each $R_5$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl or $C_6$-$C_{32}$ alkylaryl, or $C_6$-$C_{32}$ substituted alkylaryl, —(CHR₆—CHR₆—O—)_w—CHR₆—CHR₆-L and siloxyl residue wherein each L is independently selected from —O—C(O)—R₇ or —O—R₇;

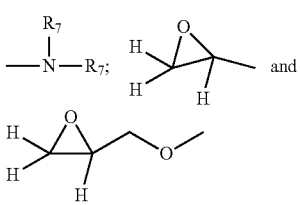

w is an integer from 0 to about 500, in one aspect w is an integer from 0 to about 200, one aspect w is an integer from 0 to about 50;

each $R_6$ is independently selected from H or $C_1$-$C_{18}$ alkyl;

each $R_7$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted aryl, and a siloxyl residue;

each T is independently selected from H;

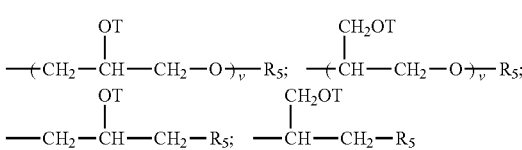

wherein each v in said organosilicone is an integer from 1 to about 10, in one aspect, v is an integer from 1 to about 5 and the sum of all v indices in each Z in the said organosilicone is an integer from 1 to about 30 or from 1 to about 20 or even from 1 to about 10.

In one embodiment, the silicone is one comprising a relatively high molecular weight. A suitable way to describe the molecular weight of a silicone includes describing its viscosity. A high molecular weight silicone is one having a viscosity of from about 10 cSt to about 3,000,000 cSt, or from about 100 cSt to about 1,000,000 cSt, or from about 1,000 cSt to about 600,000 cSt, or even from about 6,000 cSt to about 300,000 cSt.

In one embodiment, the silicone comprises a blocky cationic organopolysiloxane having the formula:

wherein:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, alkoxy, C$_1$-C$_{32}$ substituted alkoxy, C$_1$-C$_{32}$ alkylamino, and C$_1$-C$_{32}$ substituted alkylamino;
at least one of M, D, or T incorporates at least one moiety G$_1$, G$_2$ or G$_3$; and G$_1$, G$_2$, and G$_3$ are each independently selected from the formula:

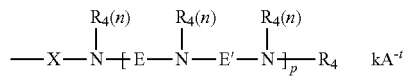

wherein:
X comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O;
each R$_4$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;
E comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;
E' comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;
p is an integer independently selected from 1 to 50;
n is an integer independently selected from 1 or 2;
when at least one of G$_1$, G$_2$, or G$_3$ is positively charged, A$^{-t}$ is a suitable charge balancing anion or anions such that the total charge, k, of the charge-balancing anion or anions is equal to and opposite from the net charge on the moiety G$_1$, G$_2$ or G$_3$; wherein t is an integer independently selected from 1, 2, or 3; and k≤(p*2/t)+1; such that the total number of cationic charges balances the total number of anionic charges in the organopolysiloxane molecule;
and wherein at least one E does not comprise an ethylene moiety.

Particularly Preferred Adjuncts for Freshening Compositions

Buffering agent—The freshening composition of the present invention may include a buffering agent which may be a carboxylic acid, or a dicarboxylic acid like maleic acid, or a polybasic acid such as citric acid or polyacrylic acid. The acid may be sterically stable, and used in this composition for maintaining the desired pH. The buffering agent may also comprise a base such as triethanolamine, or the salt of an organic acid such as sodium citrate. The freshening composition may have a pH from about 3 to about 8, alternatively from about 4 to about 7, alternatively from about 5 to about 8, alternatively from about 6 to about 8, alternatively about 6 to about 7, alternatively about 7, alternatively about 6.5. Carboxylic acids such as citric acid may act as metal ion chelants and can form metallic salts with low water solubility. As such, in some embodiments, the freshening composition is essentially free of citric acids. The buffer can be alkaline, acidic or neutral.

Other suitable buffering agents for freshening compositions of the present invention include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine. Other nitrogen-containing buffering agents are tri(hydroxymethyl) amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-di-amino-propanol N,N'-tetra-methyl-1,3-diamino-2-propanol, N,N-bis(2-hydroxyethyl)glycine (bicine) and N-tris (hydroxymethyl)methyl glycine (tricine). Mixtures of any of the above are also acceptable.

The freshening compositions may contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer—The freshening composition of the present invention may contain a solubilizing aid to solubilize any excess hydrophobic organic materials, particularly some malodor reduction materials of the current invention, perfume materials, and also optional ingredients (e.g., insect repelling agent, antioxidant, etc.) which can be added to the composition, that are not readily soluble in the composition, to form a clear translucent solution. A suitable solubilizing aid is a surfactant, such as a no-foaming or low-foaming surfactant. Suitable surfactants are nonionic surfactants, cationic surfactants, amphoteric surfactants, zwitterionic surfactants, and mixtures thereof.

In some embodiments, the freshening composition contains nonionic surfactants, cationic surfactants, and mixtures thereof. In one embodiment, the freshening composition contains ethoxylated hydrogenated castor oil. One type of suitable hydrogenated castor oil that may be used in the present composition is sold as Basophor™, available from BASF.

Freshening compositions containing anionic surfactants and/or detergent surfactants may make fabrics susceptible to soiling and/or leave unacceptable visible stains on fabrics as the solution evaporates off of the fabric. In some embodiments, the freshening composition is free of anionic surfactants and/or detergent surfactants.

When the solubilizing agent is present, it is typically present at a level of from about 0.01% to about 3%, alternatively from about 0.05% to about 1%, alternatively from about 0.01% to about 0.05%, by weight of the freshening composition.

Antimicrobial Compounds—The freshening composition of the present invention may include an effective amount of a compound for reducing microbes in the air or on inanimate surfaces. Antimicrobial compounds are effective on gram negative and gram positive bacteria and fungi typically found on indoor surfaces that have contacted human skin or pets such as couches, pillows, pet bedding, and carpets. Such microbial species include Klebsiella pneumoniae, Staphylococcus aureus, Aspergillus niger, Klebsiella pneumoniae, Streptococcus pyogenes, Salmonella choleraesuis, Escherichia coli, Trichophyton mentagrophytes, and Pseudomonas aeruginosa. In some embodiments, the antimicrobial compounds are also effective on viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the freshening composition of the present invention can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

In one embodiment, a quaternary compound is used. Examples of commercially available quaternary compounds suitable for use in the freshening composition are Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the freshening composition.

Preservatives—The freshening composition of the present invention may include a preservative. The preservative is included in the present invention in an amount sufficient to prevent spoilage or prevent growth of inadvertently added microorganisms for a specific period of time, but not sufficient enough to contribute to the odor neutralizing performance of the freshening composition. In other words, the preservative is not being used as the antimicrobial compound to kill microorganisms on the surface onto which the composition is deposited in order to eliminate odors produced by microorganisms. Instead, it is being used to prevent spoilage of the freshening composition in order to increase the shelf-life of the composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof. Non-limiting examples of commercially available water-soluble preservatives for use in the present invention include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative are from about 0.0001% to about 0.5%, alternatively from about 0.0002% to about 0.2%, alternatively from about 0.0003% to about 0.1%, by weight of the freshening composition.

Wetting Agents—The freshening composition may include a wetting agent that provides a low surface tension that permits the composition to spread readily and more uniformly on hydrophobic surfaces like polyester and nylon. It has been found that the aqueous solution, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated aqueous compositions.

Non-limiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C12-18 aliphatic alcohols, are not generally compatible with the cyclodextrin. Certain of the block polymer surfactant compounds designated Pluronic® and Tetronic® by the BASF-Wyandotte Corp., Wyandotte, Mich., are readily available. Nonlimiting examples of wetting agents of this type are described in U.S. Pat. No. 5,714,137 and include the Silwet® surfactants available from Momentive Performance Chemical, Albany, N.Y. Exemplary Silwet surfactants are as presented in Table 8 which may be used alone or in combinations of one another.

TABLE 8

| | | | Name | | | | |
|---|---|---|---|---|---|---|---|
| L-7608 | L-7607 | L-77 | L-7605 | L-7604 | L-7600 | L-7657 | L-7602 |

| Average MW | 600 | 1000 | 600 | 6000 | 4000 | 4000 | 5000 | 3000 |
|---|---|---|---|---|---|---|---|---|

In another aspect of the invention freshening fabric is a restoration of the fabric such as its surface appearance (reduction of wrinkling, improved color appearance, improved or restored fabric shape). Adjunct ingredients that help restore fabric appearance are selected from: water soluble or miscible quaternary ammonium surfactants and water insoluble oil components together with surfactants, emulsifiers, and solvents needed to form a composition that is stable and does not separate. Some non-limiting preferred emulsifiers are sorbitan esters and sorbitan esters modified with alkylene oxides, such as Tween® 20 (polyoxyethylene (20)sorbitan monolaurate, branched surfactants, like Guerbet alcohols or alkylene oxide modified Guerget alcohols such as Lutensol® XL 70 (Oxirane, 2-methyl-, polymer with oxirane, mono(2-propylheptyl) ether, BASF). It is optional but preferred to have a wetting agent in this aspect of the invention. Wetting agents aid in spreading components and in reducing foaming of the composition during spraying. Some preferred wetting agents include the class of wetting agents known in the art as superwetters. Not to be bound by theory, superwetters pack very efficiently at surfaces resulting in an extremely low equilibrium surface tension. Non-limiting examples of such surfactants include Surfynols® like Surfynol® 465 and Surfynol® 104PG 50 (Dow Chemicals).

Water soluble or miscible quaternary ammonium surfactant:

Typically, minimum levels of the water soluble quat included in the compositions of the present invention are at least about 0.01%, preferably at least about 0.05%, more preferably at least about 0.1% even more preferably at least about 0.2% by weight, based on the total weight of the composition. Typically maximum levels of water soluble quaternary agent included in the composition are up to about 20%, preferably less than about 10%, and more preferably less than about 3% based on the total weight of the composition. Typically, the agent is present in the composition in an amount of about 0.2% to about 1.0%.

Specifically, the preferred water soluble quaternary compounds are dialkly quaternary surfactant compounds. Suitable quaternary surfactants include, but are not limited to, quaternary ammonium surfactants having the formula:

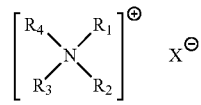

wherein $R_1$ and $R_2$ are individually selected from the group consisting of $C_1$-$C_4$ alkyl, $C_1$-$C_4$ hydroxy alkyl, benzyl, and —$(C_2H_4O)_xH$ where x has a value from about 2 to about 5; X is an anion; and (1) $R_3$ and $R_4$ are each a $C_6$-$C_{14}$ alkyl or (2) $R_3$ is a $C_6$-$C_{18}$ alkyl, and $R_4$ is selected from the group consisting of $C_1$-$C_{10}$ alkyl, $C_1$-$C_{10}$ hydroxy alkyl, benzyl, and —$(C_2H_4O)_xH$ where x has a value from 2 to 5. A preferred asymmetric quaternary compounds for this invention are compounds where R3 and R4 are not identical, and preferably one is branched and the other one is linear.

An example of a preferred asymmetric quaternary compound is ARQUAD HTL8-MS where X is a methyl sulfate ion, R1 and R2 are methyl groups, R3 is a hydrogenated tallow group with <5% mono unsaturation, and R4 is a 2-ethylhexyl group. ARQUAD HTL8-MS is available from Akzo Nobel Chemical of Arnhem, Netherlands.

An example of a suitable symmetric quaternary compound is UNIQUAT 22c50 where X is a carbonate and bicarbonate, R1 and R2 are methyl groups, R3 and R4 are C10 alkyl groups. UNIQUAT 22c50 is a registered trademark of Lonza and in North America is available thru Lonza Incorporated of Allendale, N.J.

Another example of a suitable water soluble quaternary compound is BARQUAT CME-35 which is N-Cetyl Ethyl Morpholinium Ethosulfate available from Lonza and having the following structure:

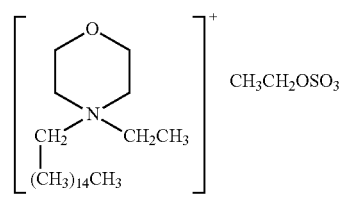

Oil Component—The oil component of the present invention represents a substantially water insoluble material that is incorporated into the composition by way of a microemulsion. The said oil component is a non-perfume raw material and a non-malodor reduction material. Typically the minimum levels of the oil component included in the composition are at least about 0.001%, preferably at least about 0.005%, more preferably at least about 0.01%, and typically maximum levels of oil components are up to about 5%, preferably less than about 3%, more preferably less than 1.5; with typical levels being in the range of about 0.05% to about 1%. The oil component can be a single component or a mixture and usually represents the incorporation of some benefit agent into the composition such as the nonlimiting example benefits softness or wrinkle reduction/release. Typically the oil component comprises substituted or unsubstituted hydrocarbon(s) and the like. For spray products it is preferred that the oil component or mix be a liquid at room temperature for ease of incorporation into the composition and less potential for nozzle clogging on drying.

The oil components of the present invention are substantially water insoluble and form a microemulsion. Substantially water insoluble means the log P of the ingredients are greater than about 1. A log P of about 1 indicates that the component would tend to partition into octanol about 10 times more than water. Some preferred, but non-limiting, components in the oil mixture are branched hydrocarbons and perfumes when perfumes are used.

Aqueous carrier—The freshening composition of the present invention may include an aqueous carrier. The aqueous carrier which is used may be distilled, deionized, or tap water. Water may be present in any amount for the composition to be an aqueous solution. In some embodiments, water may be present in an amount of about 85% to 99.5%, alternatively about 90% to about 99.5%, alternatively about 92% to about 99.5%, alternatively about 95%, by weight of said freshening composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, the level of monohydric alcohol may about 1% to about 5%, alternatively less than about 6%, alternatively less than about 3%, alternatively less than about 1%, by weight of the freshening composition.

Other ingredients—The freshening composition may include perfume raw materials that solely provide a hedonic benefit (i.e. that do not neutralize malodors yet provide a pleasant fragrance). Suitable perfumes are disclosed in U.S. Pat. No. 6,248,135, which is incorporated in its entirety by reference. For example, the freshening composition may include a mixture of volatile aldehydes for neutralizing a malodor and hedonic perfume aldehydes. Where perfumes, other than the volatile aldehydes in the malodor control component, are formulated into the freshening composition of the present invention, the total amount of perfumes and volatile aldehydes in the malodor control component may be from about 0.015% to about 1%, alternatively from about 0.01% to about 0.5%, alternatively from about 0.015% to about 0.3%, by weight of the freshening composition.

The freshening composition may also include diluents. Exemplary diluents include dipropylene glycol methyl ether, and 3-methoxy-3-methyl-1-butanol, and mixtures thereof.

Optionally, adjuvants can be added to the freshening composition herein for their known purposes. Such adjuvants include, but are not limited to, water soluble metallic salts, including zinc salts, copper salts, and mixtures thereof; antistatic agents; insect and moth repelling agents; colorants; antioxidants; aromatherapy agents and mixtures thereof.

The freshening composition may include other malodor reducing technologies in addition to the malodor reduction composition of the current invention. This may include, without limitation, amine functional polymers, metal ions, cyclodextrins, cyclodextrin derivatives, polyols, oxidizing agents, activated carbon, and combinations thereof.

Particularly Preferred Adjuncts for Personal Care Compositions

While not essential for the purposes of the present invention, the non-limiting list of adjuncts illustrated hereinafter are suitable for use in the instant compositions and may be desirably incorporated in certain aspects of the invention, for example to assist or enhance performance.

A variety of optional ingredients can also be added to personal care compositions. Optional ingredients can include, but are not limited to, structurants, humectants, fatty acids, inorganic salts, and other antimicrobial agents or actives.

A personal care composition can also include hydrophilic structurants such as carbohydrate structurants and gums. Some suitable carbohydrate structurants include raw starch (corn, rice, potato, wheat, and the like) and pregelatinized starch. Some suitable gums include carregeenan and xanthan gum. A personal care composition can include from about 0.1% to about 30%, from about 2% to about 25%, or from about 4% to about 20%, by weight of the personal care composition, of a carbohydrate structurant.

A personal care composition can also include one or more humectants. Examples of such humectants can include polyhydric alcohols. Further, humectants such as glycerin can be included the personal care composition as a result of production or as an additional ingredient. For example, glycerin can be a by-product after saponification of the personal care composition. Including additional humectant can result in a number of benefits such as improvement in hardness of the personal care composition, decreased water activity of the personal care composition, and reduction of a weight loss rate of the personal care composition over time due to water evaporation.

A personal care composition can include inorganic salts. Inorganic salts can help to maintain a particular water content or level of the personal care composition and improve hardness of the personal care composition. The inorganic salts can also help to bind the water in the personal care composition to prevent water loss by evaporation or other means. A personal care composition can optionally include from about 0.01% to about 15%, from about 1% to about 12%, or from about 2.5% to about 10.5%, by weight of the personal care composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

A personal care composition can include one or more additional antibacterial agents that can serve to further enhance antimicrobial effectiveness of the personal care composition. A personal care composition can include, for example, from about 0.001% to about 2%, from about 0.01% to about 1.5%, or from about 0.1% to about 1%, by weight of the personal care composition, of additional antibacterial agent(s). Examples of suitable antibacterial agents can include carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids. Other suitable antibacterial agents are described in U.S. Pat. No. 6,488,943.

Scalp Active Material—In an embodiment of the present invention, the personal care composition may comprise a scalp active material, which may be an anti-dandruff active. In an embodiment, the anti-dandruff active is selected from the group consisting of: pyridinethione salts; zinc carbonate; azoles, such as ketoconazole, econazole, and elubiol; selenium sulfide; particulate sulfur; keratolytic agents such as salicylic acid; and mixtures thereof. In a further embodiment, the anti-dandruff active may be an anti-dandruff particulate. In an embodiment, the anti-dandruff particulate is a pyridinethione salt. Such anti-dandruff particulate should be physically and chemically compatible with the components of the composition, and should not otherwise unduly impair product stability, aesthetics or performance.

Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulfide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulfide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition. Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+} A^{m-}_{x/m} \cdot nH_2O$ wherein some or all of the divalent ions ($M^{2+}$) are zinc ions. Yet another class of ZLMs can be prepared called hydroxy double salts In an embodiment, the ZLM is a hydroxy double salt conforming to the formula $[M^{2+}_{1-x}M^{2+}_{1+x}(OH)_{3(1-y)}]^+ A^{n-}_{(1-3y)/n} \cdot nH_2O$ where the two metal ions ($M^{2+}$) may be the same or different. If they are the same and represented by zinc, the formula simplifies to $[Zn_{1+x}(OH)_2]^{2x+} 2x\, A^- \cdot nH_2O$.

This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

Liquid Personal Care Compositions

Exemplary liquid rinse-off personal care compositions can include an aqueous carrier, which can be present at a level of from about 5% to about 95%, or from about 60% to about 85%. The aqueous carrier may comprise water, or a miscible mixture of water and organic solvent. Non-aqueous carrier materials can also be employed.

Such rinse-off personal care compositions can include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactants for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be sufficient to provide a desired cleaning and/or lather performance, and generally ranges from about 2% to about 50%.

Amphoteric detersive surfactants suitable for use in the rinse-off personal care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

The liquid rinse off personal care composition can comprise one or more phases. Such personal care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a personal care composition can include at least one surfactant. The cleansing phase can be an aqueous structured surfactant phase and constitute from about 5% to about 20%, by weight of the personal care composition. Such a structured surfactant phase can include sodium trideceth(n) sulfate, hereinafter STnS, wherein n can define average moles of ethoxylation. n can range, for example, from about 0 to about 3; from about 0.5 to about 2.7, from about 1.1 to about 2.5, from about 1.8 to about 2.2, or n can be about 2. When n can be less than 3, STnS can provide improved stability, improved compatibility of benefit agents within the personal care compositions, and increased mildness of the personal care compositions as disclosed in U.S. Pre-Grant Publication No. 2010/009285 A1.

The cleansing phase can also comprise at least one of an amphoteric surfactant and a zwitterionic surfactant. Suitable amphoteric or zwitterionic surfactants (in addition to those cited herein) can include, for example, those described in U.S. Pat. Nos. 5,104,646 and 5,106,609.

A cleansing phase can comprise a structuring system. A structuring system can comprise, optionally, a non-ionic emulsifier, optionally, from about 0.05% to about 5%, by weight of the personal care composition, of an associative polymer; and an electrolyte.

The personal care composition can optionally be free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. Pre-Grant Publication No. 2010/0322878 A1.

Rinse-off personal care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50% benefit agent by weight of the personal care composition. The benefit phase can alternatively comprise less benefit agent, for example, from about 0.5% to about 20% benefit agent, by weight of the personal care composition. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. Pre-Grant Publication No. 2012/0009285 A1.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

The rinse-off personal care composition can be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device can help delivery of the particulate antimicrobial agent to target regions, such as, for example, hair follicles and undulations that can exist in the underarm. The rinse-off care product can be sold together with such an implement or device. Alternatively, an implement or device can be sold separately but contain indicium to indicate usage with a rinse-off care product. Implements and delivery devices can employ replaceable portions (e.g., the skin interaction portions), which can be sold separately or sold together with the rinse-off care product in a kit.

Solid Personal Care Compositions

As noted herein, personal care compositions can take on numerous forms. One suitable form is that of a solid personal care composition. Solid compositions can take many forms like powder, pellets, bars, etc. These forms will generally be described herein as bar soap, but it should be understood that the solid composition could be in another form or shape. One example of a bar soap personal care composition can include from about 0.1% to about 35%, by weight of the personal care composition, of water, from about 45% to about 99%, by weight of the personal care composition, of soap, and from about 0.01% to about 5%, by weight of the personal care composition, of a particulate antimicrobial agent. Another suitable antimicrobial bar soap can include, for example, from about 0.1% to about 30%, by weight of the personal care composition, of water, from about 40% to about 99%, by weight of the personal care composition, of soap, and from about 0.25% to about 3%, by weight of the personal care composition, of a particulate antimicrobial agent.

Bar soap compositions can be referred to as conventional solid (i.e. non-flowing) bar soap compositions. Some bar soap composition can comprise convention soap, while others can contain synthetic surfactants, and still others can contain a mix of soap and synthetic surfactant. Bar compositions can include, for example, from about 0% to about 45% of a synthetic anionic surfactant. An example of a suitable conventional soap can include milled toilet bars that are unbuilt (i.e. include about 5% or less of a water-soluble surfactancy builder).

A personal care bar composition can include soap. By weight, the soap can be, for example, from about 45% to about 99%, or from about 50% to about 75%, by weight of the personal care composition. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a personal care composition. The soap included in a personal care composition can include sodium soaps or a combination of sodium soaps with from about 1% to about 25% ammonium, potassium, magnesium, calcium, or a mixture of these soaps. Additionally, the soap can be well-known alkali metal salts of alkanoic or alkenoic acids having from about 12 to about 22 carbon atoms or from about 12 to about 18 carbon atoms. Another suitable soap can be alkali metal carboxylates of alkyl or alkene hydrocarbons having from about 12 to about 22 carbon atoms. Additional suitable soap compositions are described in U.S. Pre-Grant Publication No. 2012/0219610 A1.

A personal care composition can also include soaps having a fatty acid. For example, one bar soap composition could contain from about 40% to about 95% of a soluble alkali metal soap of $C_8$-$C_{24}$ or $C_{10}$-$C_{20}$ fatty acids. The fatty acid can, for example, have a distribution of coconut oil that can provide a lower end of a broad molecular weight range or can have a fatty acid distribution of peanut or rapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{18}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof, since such oils can be among more readily available fats. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principle chain lengths can be $C_{16}$ and higher. The soap included in a personal care composition can be, for example, a sodium soap having a mixture of about 67-68% tallow, about 16-17% coconut oil, about 2% glycerin, and about 14% water.

Soap included in a personal care composition can also be unsaturated in accordance with commercially acceptable standards. For example, a soap included in a personal care composition can include from about 37% to about 45% unsaturated saponified material.

Soaps included in a personal care composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a personal care composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a personal care composition.

Test Methods for the Commercial Products/Formulations
Viscosity Test Method

Viscosity is measured using an AR 550 rheometer/viscometer from TA instruments (New Castle, Del., USA), using parallel steel plates of 40 mm diameter and a gap size of 500 µm. The high shear viscosity at 20 is obtained from a logarithmic shear rate sweep from $0.1\ s^{-1}$ to $25\ s^{-1}$ in 3 minutes time at 21° C.

Test Method for Determining the Logarithm of the Octanol/Water Partition Coefficient (log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Cleaning and/or Treatment Composition Examples

A series of cleaning and/or treatment compositions are prepared and evaluated as follows: the examples being designated with the letters CL followed by the sequence to distinguish from the microcapsule examples, noted above. In each example and table below, the amounts of each ingredient is presented as a wt %.

Example CL1—Light Cleaning/Additive Composition

A liquid composition for very light cleaning or additive to the laundry process is prepared with microcapsules of the present invention by combining the microcapsules with the additional ingredients presented in Table 9.

TABLE 9

| Ingredients | Amount |
| --- | --- |
| Nonionic Surfactant (1) | 0-10 |
| Emulsifier (2) | 0-10 |
| Cationic surfactant | 0-10 |
| Anti-bac | 0-5 |
| Free (Neat) Perfume | 0-10 |
| Microcapsules (3) | 0-10 |
| Structurant | 0-0.3 |
| Aesthetics Dye | 0.015 |
| Water | Balance |

(1) Alkyl ethoxylate with alkyl chain length between C8 and C18, preferably C12 to C16 and mixtures thereof with 3 to 12 ethoxylate groups, preferably 5 to 9.

(2) Emulsifier description, including Cremophor, Basophor, Spans and Tweens, etc.

(3) Microcapsules made in accordance with the examples of the present specification Example CL 2—Liquid Detergent Compositions A HDL-Heavy Duty Liquid composition is prepared with microcapsules of the present invention by combining the microcapsules with the additional ingredients presented in Table 10. The exemplified space is meant to represent dilute to concentrated detergent products. The resulting detergent liquid product when used to wash articles of clothing is effective at freshening washed clothing.

TABLE 10

| Ingredient | % wt Active |
| --- | --- |
| Alkyl (ethoxy) sulfate (1) | 0-30 |
| Linear alkyl benzene sulfonic acid (2) | 0-30 |
| HSAS (3) | 0-30 |
| Nonionic Surfactant (4) | 0-15 |
| Amine Oxide | 0-8 |
| Citric Acid | 0-10 |
| Lactic Acid | 0-10 |
| $C_{12}$-$C_{18}$ Fatty Acid | 0-5 |
| Protease (55.3 mg/g) | 0-3 |
| Amylase (25.4 mg/g) | 0-2 |
| Borax | 0-5 |
| Calcium Formate | 0-0.5 |
| Polyethyleneimine 600, EO20 (5) | 0-5 |
| Polyethyleneimine 600, EO24, PO16 (6) | 0-5 |
| DTPA (7) | 0-5 |
| Optical Brightener (8) | 0-1 |
| NaOH | As needed |
| Na Cumene Sulfonate | 0-5 |
| Na Formate | 0-1 |
| MEA hydrogenated castor oil | 0-0.5 |
| Aesthetics Dye | 0-1.0 |

TABLE 10-continued

| Ingredient | % wt Active |
|---|---|
| Free (Neat) Perfume | 0-3.0 |
| Microcapsules (9) | 0-5 |
| Water and Solvent | To 100 |
| pH | 3.5-8.5 |

(1) Typically the alkyl group has about 12 to about 18 carbons and with 0 to about 3 ethoxylate groups.
(2) Typically the alkyl group has about 10 to about 16 carbons.
(3) HSAS is secondary alkyl sulfate, acid form
(4) Alkyl ethoxylate with about 12 to about 18 carbons and about 5 to about 9 moles ethoxylation.
(5) Polyethyleneimine at about 600 molecular weight reacted with about 20 moles of ethylene oxide.
(6) Polyethyleneimine at about 600 molecular weight reacted with about 24 moles of ethylene oxide and about 16 moles of propylene oxide.
(7) Select optical brighteners from one or more of the following, Brightener 14, Brightener 36, Brightener 49.
(8) Select chelant from one or a combination of the following non-limiting list DTPA is diethylene triamine pentaacetic acid, Tiron ® is 4,5-Dihydroxy-1,3-benzenedisulfonic acid disodium salt monohydrate, EDTA ethylene diamine tetra acetate, HEDP 1-Hydroxyethylidene-1,1-diphosphonic Acid, Octapirox 1-Hydroxy-4- methyl-6-(2,4,4-trimethylpentyl)-2(1H)-pyridone Ethanolamine, EDDS Ethylenediamine-N,N'-disuccinic acid.
(9) Microcapsules made in accordance with the examples of the present specification

Example CL3—Liquid Fabric Enhancer Composition

Examples of liquid fabric enhancer compositions are prepared with microcapsules of the present invention by combining the microcapsules of the present invention with the additional ingredients as presented in Table 11.

TABLE 11

| Ingredient | A | B | C | D |
|---|---|---|---|---|
| FSA[1] | 12 | 21 | 18 | 14 |
| Low MW alcohol | 1.95 | 3.0 | 3.0 | 2.28 |
| Structurant | 1.25[2] | NIL | 0.2[3] | NIL |
| Free (Neat) Perfume | 1.50 | 1.8 | 2.0 | 1.50 |
| Microcapsules[4] | 4.0 | 1.85 | 1.85 | 3.7 |
| Calcium Chloride | 0.10 | 0.12 | 0.1 | 0.45 |
| DTPA[6] | 0.005 | 0.005 | 0.005 | 0.005 |
| Preservative (ppm)[7] | 5 | 5 | 5 | 5 |
| Antifoam[8] | 0.015 | 0.15 | 0.11 | 0.011 |
| Polyethylene imines[9] | 0.15 | 0.05 | NIL | 0.1 |
| PDMS emulsion[10] | NIL | 0.5 | 1 | 2.0 |
| Dispersant[11] | NIL | NIL | 0.5 | 0.2 |
| Organosiloxane[12] | 5 | NIL | NIL | NIL |
| Front-end Stability Aid | 0.06[13] | 0.63[14] | 0.36[13] | 0.14[14] |
| Dye (parts per million ppm) | 40 | 11 | 30 | 40 |
| Ammonium Chloride | 0-0.1 | 0-0.1 | 0-0.1 | 0.10 |
| Hydrochloric Acid | 0.010 | 0.01 | 0.10 | 0.010 |
| Water | Balance | Balance | Balance | Balance |

[1]N,N-di(tallowoyloxyethyl)-N,N-dimethylammonium chloride.
[2]Cationic high amylose maize starch-available from National Starch under the trade name HYLON VII ®.
[3]Cationic polymer available from BASF ® under the name Rheovis ® CDE.
[4]Microcapsules made in accordance with the examples of the present specification
[5]Diethylene triamine pentaacetic acid
[6]19% active aqueous solution of 1,2 Benzisothiazolin-3-one (BIT) in dipropylene glycol and water available from Dow Chemical under the trade name Koralone B-119
[7]Silicone antifoam agent available from Dow Corning ® under the trade name DC2310.
[8]Polyethylene imines available from BASF under the trade name Lupasol ®.
[9]Polydimethylsiloxane emulsion from Dow Corning ® under the trade name DC346.
[10]Non-ionic such as TWEEN 20 ™ or cationic surfactant as Berol 648 and Ethoquad ® C 25 from Akzo Nobel.
[11]Organosiloxane polymer condensate made by reacting hexamethylenediisocyanate (HDI), and a, w silicone diol and 1,3-propanediamine, N'-(3-(dimethylamino)propyl)-N, N-dimethyl-Jeffcat Z130) or N-(3- dimethylaminopropyl)-N,Ndiisopropanolamine (Jeffcat ZR50) commercially available from Wacker Silicones, Munich, Germany.
[12]Fineoxocol ® 180 from Nissan Chemical Co.
[13]Isofol ® 16 from Sasol.
**For example PGE Liquid fabric enhancer compositions in EXAMPLE CL3 are made by combining the molten fabric softener active with the front-end stability agent to form a first mixture. This first mixture is combined with water and hydrochloric acid using a high shear mixing device to form a second mixture. The adjunct ingredients are combined with the second mixture using low shear mixing to form the fabric enhancing formula.

Liquid fabric enhancer compositions in EXAMPLE CL3 are used by dosing 10 to 60 g of the formula into the rinse liquor for example via dispensing into a clothes washing machine. Clothes are dried on a line or in an automated clothes dryer. The fabrics treated with these formulas have improved feel and scent.

Example CL4—Liquid Fabric Enhancer Composition

Examples of liquid fabric enhancer compositions are prepared with microcapsules of the present invention by combining the microcapsules with the additional ingredients as presented in Table 12.

TABLE 12

| Ingredients | A | B | C | D | E | F | G | H | I |
|---|---|---|---|---|---|---|---|---|---|
| DEEDMAC[1] | 16 | 9 | 9 | 12 | 4 | NIL | NIL | NIL | NIL |
| Dialkyl esterdimethyl ammonium methyl sulfate[2] | NIL | NIL | NIL | NIL | NIL | 7 | 2.5 | 9 | 11 |
| HCl | 0.02 | 0.01 | 0.01 | 0.01 | NIL | 0.01 | NIL | 0.01 | 0.01 |
| Fromic Acid | 0.05 | 0.05 | 0.05 | 0.05 | 0.05 | 0.05 | 0.025 | 0.05 | 0.05 |
| Proxel ®[3] | 0.02 | 0.02 | 0.02 | 0.02 | 0.02 | 0.02 | 0.02 | 0.02 | 0.02 |
| CaCl2 | 1 | 0.3 | 0.3 | 0.4 | NIL | 0.3 | NIL | 0.1 | 0.1 |
| Antifoam MP10[4] | 0.2 | 0.1 | 0.1 | 0.1 | 0.1 | 0.1 | 0.1 | 0.1 | 0.1 |
| Rheovis CDE ®[5] | 0.1 | NIL | NIL | 0.4 | 0.1 | 0.2 | NIL | 0.2 | |
| Flosoft ®[6] | NIL | 0.1 | 0.1 | 0.05 | NIL | NIL | NIL | 0.3 | NIL |
| Bardac 2250 ®[7] | NIL | NIL | 0.5 | NIL | NIL | NIL | NIL | NIL | 0.5 |
| NaHEDP[8] | 0.03 | 0.03 | 0.03 | 0.03 | 0.03 | 0.03 | 0.03 | 0.03 | 0.03 |
| Genapol T680 ®[9] | NIL | NIL | NIL | NIL | NIL | NIL | NIL | 0.6 | 0.8 |
| CAE10[10] | NIL | 0.6 | NIL | NIL | NIL | NIL | NIL | NIL | NIL |
| Glycerol | NIL | 10 | NIL | NIL | NIL | NIL | NIL | NIL | 5 |

TABLE 12-continued

| Ingredients | A | B | C | D | E | F | G | H | I |
|---|---|---|---|---|---|---|---|---|---|
| Perfume | 0-2 | 0-1 | 0-1.5 | 0-3 | 0-2.3 | 0-1.5 | 0-3 | 0-0.8 | 0-0.5 |
| Encapsulated perfume | 0-0.25 | 0-0.5 | 0-1 | 0-0.6 | 0-1.5 | 0-3 | 0-0.5 | 0-1 | 0-5 |
| Water | To 100 | To 100 | To 100 | To 100 | To 100 | To 100 | To 100 | To 100 | To 100 |

[1] 91% activity, 9% isopropanol, supplied by Evonik
[2] Reaction product of triethanolamine and alkyl and/or fatty acids followed by methylation.
[3] Proxel GXL, 20% activity, supplied by Lonza
[4] MP10, 8% activity, supplied by Dow Corning
[5] Rheovis CDE, supplied by BASF
[6] Flosoft 222, supplied by SNF
[7] Bardac 2250, 50% activity, supplied by Lonza
[8] 20% activity
[9] Genapol T680, supplied by Clariant
[10] C12-14 ALCOHOL ETHOXYLATE AE 10 (24E10)

Example CL5—Soluble Uni-Dose Heavy Duty Liquid Composition

Examples of Soluble Uni-dose heavy duty liquid composition are prepared with microcapsules of the present invention by combining the microcapsules with the additional ingredients as presented in Table 13. The resulting Unidose pouch product when used to wash articles of clothing is effective at freshening garments.

TABLE 13

| | A | B | C | D | E | F 3 compartments pouched product | | |
|---|---|---|---|---|---|---|---|---|
| Form | liquid | liquid | liquid | liquid | gel | liq | liq | liq |
| Compartment # | 1 | 1 | 1 | 1 | 1 | 1 | 2 | 3 |
| Dosage (g) | 36.0 | 38.0 | 32.0 | 36.0 | 40.0 | 34.0 | 25 | 35 |
| Alkylbenzene sulfonic acid | 14.5 | 13.8 | 16.0 | 14.5 | 13.5 | 14.5 | 20.0 | NIL |
| $C_{12-14}$ alkyl ethoxy 3 sulfate | 8.5 | 16.4 | 10.0 | 8.5 | 15.0 | 8.5 | NIL | NIL |
| $C_{12-13}$ alkyl 3-ethoxylate | NIL | NIL | NIL | 13.0 | NIL | NIL | NIL | NIL |
| $C_{12-14}$ alkyl 7-ethoxylate | 12.5 | 9.0 | 14.0 | NIL | 4.0 | 12.5 | 17.0 | NIL |
| C12-18 Fatty acid | 14.5 | 8.5 | 16.0 | 15.0 | 7.2 | 14.5 | 13.0 | NIL |
| Citric acid | NIL | NIL | NIL | 2.0 | 4.1 | NIL | NIL | NIL |
| Enzymes | 0-3 | 0-3 | 0-3 | NIL | 0-3 | 0-3 | 0-3 | NIL |
| PAP granule[1] | NIL | NIL | NIL | NIL | NIL | NIL | NIL | 50.0 |
| Ethoxysulfated Hexamethylene Diamine Dimethyl Quat | NIL | 3.0 | NIL | NIL | NIL | NIL | 2.2 | NIL |
| Ethoxylated Polyethylenimine | 4.0 | 1.0 | NIL | 4.0 | 3.0 | 2.0 | NIL | NIL |
| Hydroxyethane diphosphonic acid | 1.0 | 1.0 | NIL | NIL | 1.6 | 0.6 | 0.6 | NIL |
| Ethylene diamine tetra(methylene phosphonic) acid | NIL | NIL | NIL | 1.0 | NIL | NIL | NIL | NIL |
| Brightener | 0.2 | 0.2 | 0.3 | 0.3 | 0.2 | 0.2 | 0.2 | NIL |
| Polydimethyl Siloxane | NIL | NIL | 3.0 | NIL | NIL | NIL | NIL | NIL |
| Hueing dye[2] | NIL | NIL | NIL | NIL | NIL | NIL | 0.05 | NIL |
| Perfume | 0-3.0 | 0-3.0 | 0-3.0 | 0-3.0 | 0-3.0 | 0-3.0 | NIL | NIL |
| Microcapsules of the present invention | 0-5 | 0-5 | 0-5 | 0-5 | 0-5 | 0-5 | NIL | NIL |
| Water and minors | | | | To 100% | | | | |
| Buffers (sodium carbonate, monoethanolamine) | | | | To pH 8.0 | | | | |
| Solvents (1,2 propanediol, ethanol), Sulfate | | | | To 100% | | | | |

[1] ε-Phthalimido-peroxy-hexanoic acid particles made by Solvay Chemicals International, Brussels, Belgium.

Example CL 6—Dish Cleaning Composition

Examples of Dish cleaning compositions are prepared with microcapsules of the present invention by combining the microcapsules with the additional ingredients presented in Table 14.

TABLE 14

|  | EXAMPLES | | | | | | |
| --- | --- | --- | --- | --- | --- | --- | --- |
|  | A | B | C | D | E | F | G |
| Alkyl $C_{10-14}$ Ethoxy Sulphate (AE0.6S) | 26.9 | NIL | NIL | 25.7 | NIL | 11.1 | 21.0 |
| Alkyl $C_{10-14}$ Ethoxy Sulphate (AE2S) | NIL | 18.7 | 26.9 | NIL | 18.7 | NIL | NIL |
| Sodium alkyl benzene sulfonate | NIL | 8.0 | NIL | NIL | NIL | NIL | NIL |
| Sodium paraffin sulfonate | NIL | NIL | NIL | NIL | 8.0 | NIL | NIL |
| C12-14 dimethyl amine oxide | 6.1 | NIL | NIL | 4.1 | NIL | 3.7 | 10.0 |
| Cocamido propyl betaine | NIL | 4.5 | 6.8 | 3.2 | 6.0 | NIL | NIL |
| C12-13 EO7 nonionic | NIL | NIL | NIL | NIL | NIL | 1.0 | 2.0 |
| Branched Nonionic: 3-propyl heptanol EO8 | 1.0 | 0.8 | NIL | NIL | NIL | NIL | 1.0 |
| PEI600-EO10-PO7 block polymer | NIL | NIL | 0.8 | NIL | NIL | 0.4 | 0.8 |
| Perfume | 0-2 | 0-2 | 0-2 | 0-2 | 0-2 | 0-2 | 0-2 |
| Perfume microcapsule of the present invention | 0-1 | 0-0.5 | 0-0.5 | 0-1.5 | 0-0.5 | 0-0.8 | 0-2 |
| Ethanol | 4.0 | 5.0 | 3.0 | 3.0 | 2.0 | NIL | 3.0 |
| Polypropylene glycol MW2000 | 1.1 | 0.8 | 1.1 | 1.1 | 1.1 | 0.5 | 1.1 |
| Sodium Chloride | 1.3 | 0.8 | 1.3 | 0.5 | 0.8 | 1.3 | 1.3 |
| Minors* and water | | | to balance up to 100% | | | | |

Example CL7—Compositions for Use in Cleaning in an Automatic Dishwashing Machine Automatic dish washing compositions are prepared with microcapsules of the present invention by combining the microcapsules with the additional ingredients presented in Table 15. Some aspects of the present invention have at least one water soluble compartment, preferably composed of Monosol 660 mm M8630K Water Soluble Film. In other aspects of the present invention the unit dose composition has more than one compartment and at least one of the compartments comprises powder as in EXAMPLE CL7 A.

TABLE 15

|  | % wt Active | | |
| --- | --- | --- | --- |
| Ingredients | A POWDER | B LIQUID | C LIQUID |
| Sodium sulfate | 0-15 | 2-7 | NIL |
| Soda ash | 20-50 | NIL | NIL |
| Zinc carbonate | NIL | 0.1-0.2 | NIL |
| Zinc sulfate | NIL | NIL | 0.3-0.7 |
| Sodium silicate | 0-2 | 3-15 | 1-2 |
| Sodium bicarbonate | NIL | NIL | 15-25 |
| Glutamic acid-N,N-diacetic acid, tetra sodium salt. | NIL | NIL | 3-7 |
| Citric acid | NIL | NIL | 1-2 |
| NaOH (preferably low iron) | NIL | 0-1.5 | |
| Carboxylate polymer, GT101 | 2.5-7 | NIL | 1.25 |
| Plurafac SLF 180 | 0.2-1.5 | NIL | 0.25-0.6 |
| MDGA | 5-15 | NIL | NIL |
| Polyacrylate thickener Polygel DKP | NIL | 0.7-2.3 | NIL |
| Acrylic/sulfonic dispersant Acusol 588 | 2-10 | NIL | NIL |
| Acrylic acid polymer Acusol 425 N | NIL | 1-3 | NIL |
| Sodium hypochlorite bleach | 0-30 | 0.3-1.5 | NIL |
| Ultimase | 0-2 | NIL | NIL |
| Stainzyme | 0-1 | NIL | NIL |
| Savinase Ultra 16XL | NIL | NIL | 0.2-0.5 |
| Termamyl Ultra 300 L | NIL | NIL | 0.1-0.15 |
| Calcium Chloride | NIL | NIL | 0.3-0.4 |
| Dipropylene Glycol | NIL | NIL | NIL |
| Nonionic Surfactant | NIL | 9-50 | NIL |
| Plurafac SLF 180 | NIL | 25-60 | NIL |
| Glycerine | NIL | 0-1 | NIL |
| Dye | NIL | 0-0.1 | NIL |
| Nitric acid | NIL | 0.005-0.05 | NIL |
| Preservative sodium benzoate | NIL | 0.25-0.8 | 0.2-0.8 |
| Perfume | 0-1 | 0-1 | 0-1 |
| Microcapsules of the present invention | 0-2 | 0-2 | 0-2 |
| Balance Water | To 100 | To 100 | To 100 |

Fatty acid has C12 to C14 alkyl groups and mixtures thereof

Rheovis ® AT 120 is a methacrylate/acrylic acid copolymer.

Example CL8—Spray for Cleaning Hard Surfaces

A spray for cleaning hard surfaces is prepared with microcapsules of the present invention by combining the microcapsules with the additional ingredients presented in Table 16.

TABLE 16

| Ingredients | % wt Active |
|---|---|
| C$_{13-15}$ alkyl ethoxylate (30) | 0-0.5 |
| C$_{9-11}$ alkyl ethoxylate (8) | 0-0.5 |
| C$_{12/14}$ Amine-oxide | 0-3 |
| Barquat 4280-Z | 0-3 |
| Ethylene glycol monohexyl ether | 0-1 |
| Phenoxyethanol | 0-1 |
| Dense Soda ash | 0-0.3 |
| Pentasodum diethylene triamine (DTPA) | 0-0.4 |
| Tartaric acid | 0-0.1 |
| Dye | 0-1.2 |
| 1,2-Benzisothioazolin-3-one | 0-0.1 |
| Perfume | 0-1 |
| Microcapsules of the present invention | 0-0.5 |
| Balance Water | To 100 |

Solid Consumer Products Examples

Example CL9—Free Flowing Particles

Free flowing particles are prepared with microcapsules of the present invention by combining the microcapsules with the additional ingredients presented in Table 17.

TABLE 17

| | % wt Active | | | |
|---|---|---|---|---|
| Ingredients | A | B | C | D |
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |
| Urea | 0-29 | 0-29 | 0-99 | 0-40 |
| Polysaccharide | 0-29 | 0-29 | 0-29 | 0-5 |
| Zeolite | 0-29 | 0-29 | 0-29 | 0-5 |
| Plasticizers/ Solvents | | | | |
| Starch/Zeolite | 0-29 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Water | 0-2 | 0-2 | 0-5 | 0-5 |
| Perfume | 0-5 | 0-5 | 0-5 | 0-5 |
| Microcapsules made in accordance with the examples of the present specification | 0-10 | 0-4.5 | 0-3 | 0-7.5 |

Example CL10—Spray-Dried Laundry Detergent Powder Composition

Spray-Dried Laundry Detergent Powder compositions are prepared with microcapsules of the present invention by combining the microcapsules with the additional ingredients as presented in Table 18

TABLE 18

| | wt % Active Slurry | | | |
|---|---|---|---|---|
| Ingredients | A | B | C | D |
| Linear alkyl benzene sulfonate | 10.6 | 15.8 | 21.3 | 35.7 |
| Acrylate/maleate copolymer | 4.6 | 6.8 | 9.4 | 14.2 |
| Ethylenediame disuccinic acid and/or Hydroxyethane dimethylene phosphonic acid | 1.4 | 2.1 | 1.7 | 2.9 |
| Sodium carbonate | 19.4 | 26.5 | 18.8 | 29.9 |
| Sodium sulfate | 28.6 | 42.4 | — | — |
| Carboxy methyl cellulose polymer | — | — | 4.3 | 7.1 |
| Carboxy methyl cellulose polymer | — | — | 4.3 | 7.1 |
| Miscellaneous, such as magnesium sulfate, brightener and one or more stabilizers | 1.4 | 2.2 | 2.5 | 4.2 |
| Perfume | 0-3 | 0-2 | 0-2 | 0-3 |
| Microcapsules made in accordance with the examples of the present specification | 0-5 | 0-5 | 0-5 | 0-5 |
| Water | Balance | Balance | Balance | Balance |

A first spray-dried laundry detergent powder is formed from an aqueous slurry, slurry A from Table 18, which is prepared having a moisture content of 34.0%. Any ingredient added above in liquid form is heated to 70° C., such that the aqueous slurry is never at a temperature below 70° C. At the end of preparation, the aqueous slurry is heated to 80° C. and pumped under pressure ($5 \times 10^6$ Nm$^{-2}$) into a counter current spray-drying tower with an air inlet temperature of from 290° C. The aqueous slurry is atomized and the atomized slurry is dried to produce a solid mixture, which is then cooled and sieved to remove oversize material (>1.8 mm) to form a spray-dried powder, which is free-flowing. Fine material (<0.15 mm) is elutriated with the exhaust the exhaust air in the spray-drying tower and collected in a post tower containment system. The spray-dried powder has a moisture content of 2.0 wt %, a bulk density of 310 g/l and a particle size distribution such that greater than 90 wt % of the spray-dried powder has a particle size of from 150 to 710 micrometers. The composition of the spray-dried powder A is listed in the Table 18. Perfume and microcapsules are sprayed onto the composition following the spray dry procedure.

A second spray-dried laundry detergent powder is formed from an aqueous slurry, slurry B from Table 18, having a moisture content of 42.0%. Any ingredient added above in liquid form is heated to 70° C., such that the aqueous slurry is never at a temperature below 70° C. At the end of preparation, the aqueous slurry is heated to 85° C. and pumped under pressure (from 6.5×10⁶ Nm⁻²), into a counter current spray-drying tower with an air inlet temperature of from 275° C. The aqueous slurry is atomized and the atomized slurry is dried to produce a solid mixture, which is then cooled and sieved to remove oversize material (>1.8 mm) to form a spray-dried powder B, which is free-flowing. Fine material (<0.15 mm) is elutriated with the exhaust the exhaust air in the spray-drying tower and collected in a post tower containment system. The spray-dried powder has a moisture content of 3.0 wt %, a bulk density of 250 g/l and a particle size distribution such that greater than 90 wt % of the spray-dried powder has a particle size of from 150 to 710 micrometers. The composition of the spray-dried powder is given in Table 18. Perfume and microcapsules are sprayed onto the composition after the spray dry process.

Example CL11—Freshening Composition

Liquid fabric spray fabric freshening compositions are prepared with microcapsules of the present invention by combining the microcapsules with the additional ingredients as presented in Table 19. The resulting fabric refreshing spray product when used to treat fabric surfaces is effective at freshening a treated fabric.

TABLE 19

| | wt % Active | | | | |
|---|---|---|---|---|---|
| Ingredient | A | B | C | D | E |
| Deionized Water | Balance | Balance | Balance | Balance | Balance |
| Ethanol | 3.0 | 3.0 | 3.0 | 3.0 | 3.0 |
| Lupasol HF[1] | NIL | NIL | NIL | NIL | NIL |
| Hydroxypropyl b-CD | NIL | NIL | NIL | NIL | NIL |
| Diethylene Glycol | NIL | NIL | NIL | NIL | NIL |
| Silwet L-7600 | 0.1 | 0.1 | 0.1 | 0.100 | 0.100 |
| Basophor EL60[2] | NIL | 0.05 | 0.05 | 0.05 | 0.05 |
| Maleic Acid and/or Citric Acid[3] | As needed | As needed | As needed | As needed | As needed |
| Koralone B-119 | 0.015 | 0.015 | 0.015 | 0.015 | 0.015 |
| Hydroxypropyl β-cyclodextrin | NIL | NIL | NIL | NIL | NIL |
| Sodium Hydroxide[3] | As needed | As needed | As needed | As needed | As needed |
| Microcapsules made in accordance with the examples of the present specification | 1 | 2 | 0.1 | 5 | 0.05 |
| Fragrance | 0 | 0 | 0 | 0 | 0 |
| Target pH | 6.8 | 6.8 | 6.8 | 6.8 | 6.8 |
| Total | 100 | 100 | 100 | 100 | 100 |

Example CL12—Dryer Added Fabric Softener Sheet Composition

A series of dryer added fabric softener sheet compositions are prepared with microcapsules of the present invention by combining the microcapsules with the additional ingredients as presented in Table 20. The compositions A-D of this example are mixed homogeneously and impregnated onto a non-woven polyester sheet having dimensions of about 6¾ in×12" (about 17.1 cm×30.5 cm) and weighing about 1 gram. The resulting dryer added fabric softener sheet product when added to an automatic dryer is effective at softening, freshening and reducing the static on clothing that contact the sheet.

TABLE 20

| Ingredient | A Wt % Active | B Wt % Active | C Wt % Active | D Wt % Active |
|---|---|---|---|---|
| DEQA[1] | 0-50 | 50 | — | — |
| DEQA[2] | 0-50 | — | — | 30 |
| DTDMAMS[3] | 0-50 | — | 50 | — |
| 7018FA[4] | 0-50 | — | 50 | — |
| TS-20[5] | 0-15 | — | — | 15 |
| SMS[6] | 0-15 | — | — | 15 |
| SDASA[7] | 0-19 | 25 | — | 19 |
| TPED[8] | — | 3 | — | — |
| Complex[9] | 0-16.5 | 16.5 | — | 8.0 |
| Clay[10] | Balance | Balance | Balance | Balance |
| Free (Neat) Perfume | 0-4 | 0-1.5 | 0-3 | 0-1.5 |
| Microcapsules[11] | 0-4 | 0-4 | 0-2 | 0-2 |
| Active Weight (g/sheet) | 2.4 | 2.4 | 1.9 | 2.4 |

[1]DEQA[1]: Di(soft tallowoyloxyethyl)dimethylammonium methyl sulfate with 25%>7018 FA, as described below, as solvent
[2]DEQA[2]: Di(soft tallowoyloxyethyl)hydroxyethylmethylammoniun methyl sulfate with 18%, partially hydrogenated tallow fatty acid solvent
[3]DTDMAMS: Di(hydrogenated tallowalkyl)dimethylammonium methyl sulfate
[4]7018FA: 70:30 Stearic Acid:Palmitic Acid (IV = 0) Industrene 7018 sold by Witco
[5]TS-20: Polyoxyethylene-20 Sorbitan Tristearate (Glycosperse TS-20, sold by Lonza
[6]SMS: Sorbitan Mono Stearate
[7]SDASA: 1:2 ratio of stearyl dimethyl amine:triple pressed stearic acid
[8]TPED: N,N,N',N'-Tetrakis(2-hydroxypropyl)ethylenediamine (Quadrol, sold by BASF)
[9]Complex: Beta-Cyclodextrin/Perfume Complex
[10]Clay: Calcium Bentonite Clay (Bentonite L sold by Southern Clay Products Free (Neat) Perfume
[11]Microcapsules made in accordance with the examples of the present specification Examples CL13-CL15—Absorbent Articles Example CL13—Pads for Menstrual Odor Control The microcapsules of the present invention are added into the core of an Always Ultra Thin Unscented menstrual pad. Optionally, a neat fragrance is preferably added beneath the core of the article.

Example CL14—Heavy AI Pants for Urine Odor Control

The microcapsules of the present invention are added into the core of an Always Discreet Adult Incontinence Under-wear, moderate absorbency. Optionally, a neat fragrance is preferably added beneath the core of the article.

Example CL15—Diapers for Odor Control

The microcapsules of the present invention are added into the core of an Pampers Cruisers Baby Diaper. Optionally, a neat fragrance is preferably added beneath the core of the article.

Examples CL16-CL17—Personal Care Compositions

Example CL16—Body Wash

Body Wash compositions are prepared with microcapsules of the present invention by combining the microcapsules with the additional ingredients as presented in Table 21.

TABLE 21

| Body Wash | A | B | C |
|---|---|---|---|
| Sodium Laureth-3 Sulfate (as 28% active) | 27.85% | 27.85% | 27.85% |
| Water | Q.S. | Q.S. | Q.S. |
| Sodium Lauryl Sulfate (as 29% active) | 10.34 | 10.34 | 10.34 |
| Cocamidopropyl Betaine B (30% active) | 4.01 | 4.01 | 4.01 |
| Citric Acid | 0.18 | 0.18 | 0.18 |
| Sodium Benzoate | 0.3 | 0.3 | 0.3 |
| Disodium EDTA | 0.12 | 0.12 | 0.12 |
| Methylchloroisothiazolinone/Methylisothiazolinone | 0.04 | 0.04 | 0.04 |
| Sodium Chloride | 2.35 | 1.7 | 1.6 |
| Neat Perfume | 1.25 | 1 | 2 |
| Microcapsules made in accordance with the examples of the present specification | 0.25 | 0.175 | 0.25 |

QS - indicates that this material is used to bring the total to 100%

Example CL17—Shampoos

Shampoo compositions are prepared with microcapsules of the present invention by combining the microcapsules with the additional ingredients as presented in Table 22.

TABLE 22

| Ingredient | A | B | C | D | E | F |
|---|---|---|---|---|---|---|
| | | Wt % | | | | |
| Ammonium Laureth Sulfate[1] | 14.1 | 14.1 | 14.1 | 14.1 | 14.1 | 14.1 |
| Ammonium Lauryl Sulfate[2] | 3.1 | 3.1 | 3.1 | 3.1 | 3.1 | 3.1 |
| Ammonium Xylenesulfonate[3] | 0.45 | 0.45 | 0.45 | 0.45 | 0.45 | 0.45 |
| TWEEN 60[4] | 3.0 | 3.0 | 3.0 | 3.0 | 3.0 | 3.0 |
| Polyquaternium-10[5] | 0.35 | 0.35 | 0.35 | 0.35 | 0.35 | 0.35 |
| Cetrimonium Chloride[6] | 0.5 | 0.5 | 0.5 | 0.5 | 0.5 | 0.5 |
| Selenium Sulfide[7] | 1.0 | 1.0 | 1.0 | 1.0 | 0.2 | 0.2 |
| Dimethicone[8] | 0.60 | 0.60 | 0.60 | 0.60 | 0.60 | 0.60 |
| Ethylene Glycol Distearate[9] | 3.0 | 3.0 | 3.0 | 3.0 | 3.0 | 3.0 |
| Cocamide MEA[10] | 3.0 | 3.0 | 3.0 | 3.0 | 3.0 | 3.0 |
| Zinc Pyrithione[11] | — | 0.2 | 0.2 | — | 1.0 | 1.0 |
| Zinc Carbonate[12] | — | — | 1.61 | — | — | 1.61 |
| Neat Fragrance | 1.1 | 0.75 | 0.75 | 0.65 | 0.85 | 1.0 |
| Microcapsules made in accordance with the examples of the present specification | 0.25 | 0.25 | 0.175 | 0.175 | 0.175 | 0.175 |
| Cetyl Alcohol[13] | 0.42 | 0.42 | 0.42 | 0.42 | 0.42 | 0.42 |
| DMDM Hydantoin | 0.40 | 0.40 | 0.40 | 0.40 | 0.40 | 0.40 |
| Sodium Chloride | 0.30 | 0.30 | 0.30 | 0.30 | 0.30 | 0.30 |
| Stearyl Alcohol[14] | 0.20 | 0.20 | 0.20 | 0.20 | 0.20 | 0.20 |
| Hydroxypropyl Methylcellulose[15] | 0.02 | 0.02 | 0.02 | 0.02 | 0.02 | 0.02 |
| Water | Q.S. | Q.S. | Q.S. | Q.S. | Q.S. | Q.S. |

[1] Ammonium Laureth Sulfate at 25% active, supplier: P&G
[2] Ammonium Lauryl Sulfate at 25% active, supplier: P&G
[3] Ammonium Xylene Sulfonate 40% active, supplier: Stepan
[4] Polysorbate 60, upplier: Croda
[5] UCARE Polymer LR400, supplier - Dow Chemical
[6] cetrimonium chloride, supplier - Croda
[7] Selenium disulfide, supplier Eskay
[8] Viscasil 330M from Momentive Performance Materials with a viscosity of 330,000 cSt (centistokes).
[9] Ethylene Glycol Disterate, supplier: Stepan
[10] Ninol COMF from the Stepan Company
[11] Zinc Pyrithione, supplier Lonza
[12] Zinc Carbonate Basic, supplier Pan Continental Chemical
[13] Cetyl Alcohol, supplier P&G
[14] Stearyl Alcohol, supplier P&G
[15] Methocel, supplier Dow Chemical Examples CL18-CL20—Antipespirant and/or Deodorant Compositions

Example CL18—Deodorants

Deodorants are prepared with microcapsules of the present invention by combining the microcapsules with the additional ingredients as presented in Table 23.

TABLE 23

| Ingredient | A | B | C | D | E |
|---|---|---|---|---|---|
| Product Form | Solid Deodorant | Solid Deodorant | Solid Deodorant | Solid Deodorant | Aerosol Deodorant or Body Spray |
| dipropylene glycol | 48 | 48 | 20 | 30 | 20 |
| propylene glycol | 19.3 | 19.3 | 22 | — | — |
| tripopylene glycol | — | — | 25 | — | — |
| Glycerine | — | — | — | 10 | — |
| PEG-8 | — | — | — | 20 | — |
| Propylene Glycol 3 Myristyl Ether | 1.4 | 1.4 | — | — | — |
| ethanol | — | — | — | — | QS |
| Water | QS | QS | QS | QS | — |
| sodium stearate | 5.4 | 5.4 | 5.5 | 5.5 | — |
| tetra sodium EDTA | 0.5 | 0.5 | 0.05 | 0.05 | — |
| sodium hydroxide | — | — | 0.04 | 0.04 | — |
| triclosan | — | — | 0.3 | 0.3 | — |
| Neat Perfume | 2.8 | 2.8 | 2 | 1.5 | 1.5 |
| Microcapsules made in accordance with the examples of the present specification | 3 | 0.7 | 1.0 | 0.5 | 0.35 |
| Blue 1 | 0.0009 | 0.0009 | — | — | — |
| Propellant (1,1 difluoroethane) | — | — | — | — | 40 |

QS - Indicates that this material is used to bring the total to 100%.

Example CL19—Antiperspirants

Antiperspirant compositions are prepared with microcapsules of the present invention by combining the microcapsules with the additional ingredients as presented in Table 24.

TABLE 24

| | Form | | | | | |
|---|---|---|---|---|---|---|
| Ingredient | Invisible Solid A | Invisible Solid B | Invisible Solid C | Soft Solid D | Soft Solid E | Soft Solid F |
| Aluminum Zirconium Trichlorohydrex Glycine Powder | 24 | 24 | 24 | 26.5 | 26.5 | 26.5 |
| Cyclopentasiloxane | Q.S | Q.S. | Q.S. | Q.S. | Q.S. | Q.S. |
| Dimethicone | — | — | — | 5 | 5 | 5 |
| CO-1897 Stearyl Alcohol NF | 14 | 14 | 14 | — | — | — |
| Hydrogenated Castor Oil MP80 Deodorized | 3.85 | 3.85 | 3.85 | — | — | — |
| Behenyl Alcohol | 0.2 | 0.2 | 0.2 | — | — | — |
| Tribehenin | — | — | — | 4.5 | 4.5 | 4.5 |
| C 18-36 acid triglyceride | — | — | — | 1.125 | 1.125 | 1.125 |
| C12-15 Alkyl Benzoate | 9.5 | 9.5 | 5 | — | — | — |
| PPG-14 Butyl Ether | 6.5 | 6.5 | — | 0.5 | 0.5 | 0.5 |
| Phenyl Trimethicone | 3 | — | 3 | — | — | — |
| White Petrolatum | 3 | — | — | 3 | 3 | 3 |
| Mineral Oil | 1.0 | 1.0 | 1.0 | — | — | — |
| Free (Neat) Perfume | 1.0 | 0.75 | 2.0 | 0.75 | 1.0 | 1.25 |
| Microcapsules made in accordance with the examples of the present specification | 0.25 | 3 | 0.35 | 0.175 | 0.25 | 0.1 |

TABLE 24-continued

| Ingredient | Invisible Solid A | Invisible Solid B | Invisible Solid C | Soft Solid D | Soft Solid E | Soft Solid F |
|---|---|---|---|---|---|---|
| Beta-Cyclodextrin complexed with Malodor reducing composition | — | 3.0 | — | — | — | 3.0 |
| Talc Imperial 250 USP | 3.0 | 3.0 | 3.0 | — | — | — |

QS - indicates that this material is used to bring the total to 100%.

Example CL20—Clear Gel Antiperspirant

Clear gel antiperspirants are prepared with microcapsules of the present invention by combining the microcapsules with the additional ingredients as presented in Table 25.

TABLE 25

| | 3.1 Clear Gel Antiperspirant | 3.2 Clear Gel Antiperspirant | 3.3 Clear Gel Antiperspirant | 3.4 Clear Gel Antiperspirant | 3.5 Clear Gel Antiperspirant |
|---|---|---|---|---|---|
| Aluminum Zirconium Octachlorohydrex Gly | 20 | 18.5 | 20 | 18 | 10 |
| Water | Q.S | Q.S. | Q.S. | Q.S. | Q.S. |
| Ethanol | 5.5 | 8 | 6 | 6.5 | 5 |
| Propylene Glycol | 5.3 | 5 | 7 | 5.5 | 8 |
| DC 5225c-Cyclopentasiloxane & PEG/PPG-18/18 Dimethicone | 7.8 | 9 | 6.5 | 7 | 8 |
| Dimethicone | 5.6 | 4.5 | 5.8 | 5 | 4.1 |
| Cyclopentasiloxane | 2.6 | 3 | 1 | 3 | 2.5 |
| Free (Neat) Perfume | 1.0 | 0.75 | 2.0 | 0.75 | 1.0 |
| Microcapsules made in accordance with the examples of the present specification | 0.25 | — | 0.35 | 0.175 | 0.25 |

QS - indicates that this material is used to bring the total to 100%.

For avoidance of doubt and to preclude any unintentional omission of an embodiment, it is to be appreciated that the present teaching also pertains to and by this reference incorporates any and all consumer products and methods of making consumer products containing or made using, respectively, the microcapsules embraced by the appended claims as well as the microcapsules resulting from the methods of the appended claims in combination with at least one consumer product ingredient. In general, these compositions and methods will contain or employ, as appropriate, a sufficient amount of said microcapsules to provide, based on the total consumer product weight, said consumer product with from 0.001% about to about 25%, preferably from about 0.01% to about 10%, more preferably from about 0.05% to about 5%, most preferably from about 0.1% to about 0.5% of said microcapsules.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

Although the process and prepared microcapsules of the present specification as well as various commercial and consumer products containing/comprising the same have been described with respect to specific embodiments and examples, it should be appreciated that the present teachings are not limited thereto and other embodiments utilizing the concepts expressed herein are intended and contemplated without departing from the scope of the present teaching as intended in the true spirit and scope of the invention. It is therefore intended any and all modifications, variations, or equivalents that fall within the spirit and scope of the underlying principles are within the scope of this invention and are covered by the appended claims.

We claim:

1. A method of making microcapsules whose shell wall comprises on one surface a melamine resin and on its other surface a (meth)acrylate polymer, said melamine resin derived from an aqueous phase composition and said (meth)acrylic polymer comprising the reaction product of either (A) a combination of (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer or (B) a combination of (a) at least one oil soluble or dispersible acidic (meth)acrylate, (b) at least one oil soluble or dispersible simple base, and (c) at least one oil soluble or dispersible multifunctional (meth)acrylate monomer or oligomer derived from an oil phase composition, and an intermediate region comprising an interpenetrating network and/or copolymer of melamine resin and (meth)acrylate polymer, said method comprising:
  (i) forming an oil-in-water or a water-in-oil emulsion of the melamine based aqueous phase and the (meth) acrylate ester oil phase,
  (ii) subjecting the emulsion to conditions for concurrently, at last in part, polymerizing the wall forming materials of each of the oil phase and water phase, and
  (iii) allowing the reaction to continue until the microcapsules of desired wall thickness are attained.

2. The method of claim 1 wherein the method further comprises the step of oligomerizing and/or prepolymerizing some or all of the (meth)acrylate polymer wall forming components of the oil phase composition subsequent to forming the emulsion but prior to initiating wall formation.

3. The method of claim 1 wherein the oil phase composition, prior to forming the emulsion, comprises oligomers and/or prepolymers of some or all of the (meth)acrylate polymer wall forming components of the oil phase composition.

4. The method of claim 1 wherein the (meth)acrylate polymer is derived from (A) (a) at least one oil soluble or dispersible amine (meth)acrylate, (b) at least one oil soluble or dispersible acidic (meth)acrylate, and (c) at least one oil soluble or dispersible multifunctional (meth)acrylate monomer or oligomer.

5. The method of claim 1 wherein the (meth)acrylate polymer is derived form (A) (a) at least one oil soluble or dispersible amine (meth)acrylate, (b) at least one oil soluble or dispersible simple acid, and (c) at least one oil soluble or dispersible multifunctional (meth)acrylate monomer or oligomer.

6. The method of claim 1 wherein the (meth)acrylate polymer is derived from (A) (a) at least one oil soluble or dispersible amine (meth)acrylate, (b) the combination of at least one oil soluble or dispersible acidic (meth)acrylate and at least one oil soluble or dispersible simple acid, and (c) at least one oil soluble or dispersible multifunctional (meth) acrylate monomer or oligomer.

7. The method of claim 1 wherein the (meth)acrylate polymer is derived from (B) (a) at least one oil soluble or dispersible acidic (meth)acrylate, (b) at least one oil soluble or dispersible simple base, and (c) at least one oil soluble or dispersible multifunctional (meth)acrylate monomer or oligomer.

8. The method of claim 1 wherein the aqueous phase composition comprises monomers, oligomers and/or prepolymers of the precursors or building blocks for a melamine-based polyurea, a melamine-formaldehyde resin, a melamine-aldehyde resin, dimethylol melamine urea, methylated dimethylol melamine urea, methylated melamine formaldehyde, methylated methylol melamine, end mixtures of melamine formaldehyde with urea formaldehyde.

9. The method of claim 8 wherein the method further comprises the step of oligomerizing and/or prepolymerizing the monomeric and/or oligomeric precursor components for the melamine resin.

10. The method of claim 9 wherein the water phase further comprises a polymeric emulsifier.

11. The method of claim 10 wherein the polymeric emulsifier is one which comes out of solution during the wall forming process and is incorporated into the shell wall.

12. The method of claim 1 wherein the wall formation is a two-step reaction process where the first reaction step comprises subjecting the emulsion to such conditions as will form prepolymers and polymers of the wall forming materials and the second reaction step comprises subjecting the emulsion to second set of conditions which effectuates the formation of the shell wall.

13. The method of claim 1 wherein the wall formation is a three-step reaction process where the first step comprising subjecting the emulsion to such conditions as will form prepolymers and polymers of the wall forming materials, the second step comprises subjecting the emulsion to a second set of conditions which effectuates building of the shell wall and the third step comprises subjecting the emulsion to a third set of conditions, which may be merely an extension or continuation of the second set of conditions, to cross-link the polymer(s) of the shell wall.

14. The method of claim 13 wherein the third step effects the cross-linking of the (meth)acrylate polymer.

15. The method of claim 1 wherein initiation of wall formation from the oil phase and the aqueous phase is concurrent.

16. The method of claim 1 wherein initiation of the wall formation from one of the oil phase and the aqueous phase is staggered relative to the other.

17. The method of claim 16 wherein wall formation of the second wall forming composition is initiated after the shell wall is partially formed from the first wall forming material but before the shell wall is impermeable to the wall forming material of the second wall forming composition.

18. The method of claim 16 wherein wall formation of the second wall forming composition is initiated after a seed capsule is formed of the first wall forming material.

* * * * *